United States Patent
Zhao et al.

(10) Patent No.: US 12,410,192 B2
(45) Date of Patent: Sep. 9, 2025

(54) COMPOUND FOR INHIBITING AND INDUCING DEGRADATION OF EGFR KINASE

(71) Applicant: BEIJING TIDE PHARMACEUTICAL CO., LTD., Beijing (CN)

(72) Inventors: Yanping Zhao, Beijing (CN); Hongjun Wang, Beijing (CN); Yeming Wang, Beijing (CN); Yuanyuan Jiang, Beijing (CN); Futian Fan, Beijing (CN); Huining Liang, Beijing (CN); Xiaoqian Wang, Beijing (CN); Yong Xie, Beijing (CN); Yanhao Zhang, Beijing (CN); Xuelian Liu, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 703 days.

(21) Appl. No.: 17/785,608

(22) PCT Filed: Dec. 16, 2020

(86) PCT No.: PCT/CN2020/136773
§ 371 (c)(1),
(2) Date: Jun. 15, 2022

(87) PCT Pub. No.: WO2021/121261
PCT Pub. Date: Jun. 24, 2021

(65) Prior Publication Data
US 2023/0159559 A1    May 25, 2023

(30) Foreign Application Priority Data
Dec. 16, 2019   (CN) .......................... 201911291237.9

(51) Int. Cl.
   *C07D 498/22*   (2006.01)
   *A61P 35/00*    (2006.01)
(52) U.S. Cl.
   CPC ............ *C07D 498/22* (2013.01); *A61P 35/00* (2018.01)

(58) Field of Classification Search
None
See application file for complete search history.

(56) References Cited

FOREIGN PATENT DOCUMENTS

| CN | 106458993 A | 2/2017 |
|---|---|---|
| CN | 109475528 A | 3/2019 |
| WO | 2018119441 A1 | 6/2018 |
| WO | 2019162323 A1 | 8/2019 |
| WO | 2020260252 A1 | 12/2020 |

OTHER PUBLICATIONS

Engelhardt, Harald et al., "Start selective and rigidify: The discovery path towards a next generation of EGFR tyrosine kinase inhibitors", Journal of Medicinal Chemistry, Retrieved: 2019.

*Primary Examiner* — Kortney L. Klinkel
*Assistant Examiner* — Donna M Nestor
(74) *Attorney, Agent, or Firm* — Lando & Anastasi, LLP

(57) ABSTRACT

Provided is an EGFR kinase inhibitor according to general formula (I) and a pharmaceutical composition containing the inhibitor. The invention can be used to treat diseases related to EGFR kinase, such as cancer. Also provided is a preparation and use of the above inhibitor.

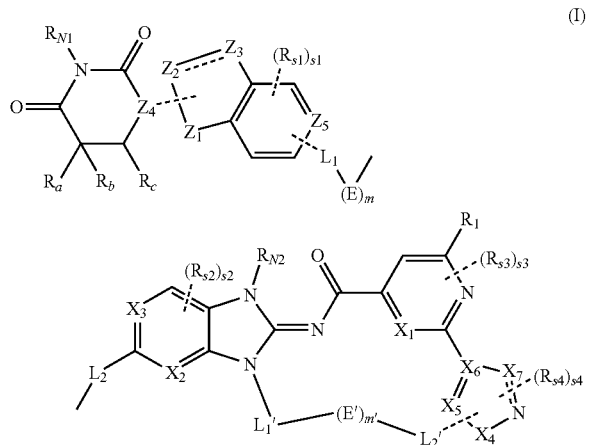

20 Claims, 1 Drawing Sheet

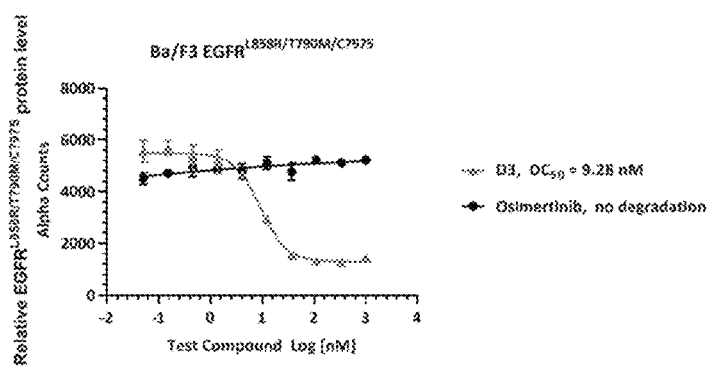

COMPOUND FOR INHIBITING AND INDUCING DEGRADATION OF EGFR KINASE

CROSS-REFERENCE TO RELATED APPLICATIONS

This application is a U.S. national phase application and claims the benefit of priority under 35 U.S.C. § 371, of International (PCT) Patent Application Serial No. PCT/CN2020/136773, filed on Dec. 16, 2020, which claims priority to Chinese Patent Application No. 201911291237.9, filed on Dec. 16, 2019, each of which is incorporated herein by reference in its entirety for all purposes.

FIELD OF THE INVENTION

The present disclosure relates to a field of medicine. Specifically, the present disclosure provides compounds capable of inhibiting EGFR kinase or inducing degradation of EGFR, and preparation and use thereof.

BACKGROUND OF THE INVENTION

Lung cancer is one of the most common malignant tumors. In 2018, there were 2.1 million new cases of lung cancer worldwide, accounting for 11.6% of all new tumor cases; 1.8 million deaths occurred, accounting for 18.4% of all tumor deaths. Among them, non-small cell lung cancer (NSCLC) accounts for about 80%-85% of all lung cancers. Epithelial Growth Factor Receptor (EGFR) is the most common non-small cell lung cancer driver gene, and about 50% of non-small cell lung cancer patients in China and 11-16% of non-small cell lung cancer patients in Western countries have EGFR gene mutation, in which the most common types of mutations are exon 19 deletion mutation (del E746-A750) and exon 21 L858R point mutation, accounting for about 90% of all EGFR mutations in populations.

EGFR small molecule inhibitors are the standard first-line treatment for non-small cell lung cancer with EGFR gene mutation and have been widely used in the field of lung cancer treatment. They competitively bind to EGFR with endogenous ligands, and inhibit the activation of tyrosine kinases, thereby blocking the EGFR signaling pathway, inhibiting tumor cell proliferation and metastasis, and promoting a series of biological effects such as tumor cell apoptosis.

The first-generation EGFR small-molecule inhibitors Gefitinib and Erlotinib have been used to treat advanced non-small cell lung cancer with activating EGFR mutations (L858R, del E746-A750). However, patients develop resistance after 10-12 months of administration of Gefitinib and Erlotinib, wherein more than 50% of drug-resistant patients are due to the secondary mutation of T790M in EGFR. Afatinib, the second-generation irreversible EGFR inhibitor, is effective for advanced non-small cell lung cancer patients with activating EGFR mutations (L858R, del E746-A750), but cannot resolve the clinical drug resistance caused by EGFR T790M mutation. Moreover, Afatinib lacks selectivity to wild-type EGFR and has great toxicity. Osimertinib, the third-generation irreversible inhibitor, overcomes the drug resistance caused by EGFR T790M and can effectively treat advanced non-small cell lung cancer patients with drug resistance caused by EGFR T790M mutation. Although Osimertinib has achieved great success in the clinical treatment of non-small cell lung cancer with EGFR T790M mutant, some patients who benefits from the treatment develops drug resistance after 9-14 months of treatment (Nature Medicine, 2015, 21 (6), 560-562). Studies have shown that up to 22% of patients with drug resistance of Osimertinib are due to EGFR C797S mutation (JAMA Oncol. 2018; 4 (11): 1527-1534). EGFR C797S mutation causes cysteine at position 797 to be mutated into serine, and Osimertinib cannot covalently bind to EGFR, resulting in drug resistance. At present, there is no effective single EGFR inhibitor for EGFR C797S in clinical practice. Therefore, the development of a new generation of EGFR inhibitors to meet the needs of clinical treatment is an urgent problem to be solved.

Ubiquitin-proteasome system (UPS) is a multi-component system of intracellular protein degradation, which is involved in important physiological and biochemical processes such as cell growth and differentiation, DNA replication and repair, cell metabolism, immune response and so on. Protein degradation mediated by the ubiquitin-proteasome pathway is an important mechanism of the body for regulating intracellular protein level and function, and plays an important role in maintaining protein homeostasis in vivo. Inducing the degradation of EGFR through the intracellular ubiquitin-proteasome pathway provides a new idea for the treatment of non-small cell lung cancer.

The present disclosure provides compounds capable of inhibiting EGFR kinase or inducing degradation of EGFR, and preparation methods and uses thereof.

SUMMARY OF THE INVENTION

The present disclosure provides compounds of general formula (I), which are useful in the treatment of EGFR kinase-mediated diseases, such as cancer.

In one aspect, the present disclosure provides a compound of general formula (I) below, or a pharmaceutically acceptable salt, enantiomer, diastereomer, racemate, solvate, hydrate, polymorph, prodrug, or isotopic variant thereof, or a mixture thereof,

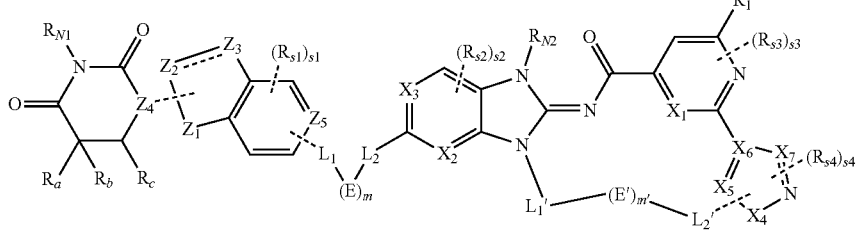

(I)

wherein

═ represents single bond or double bond;

----- represents that the point of attachment to the rest of the molecule can be located at an available point of a ring;

$Z_1$ is O, S, N or C atom, which is optionally substituted with one or two $R_{Z1}$; or $Z_1$ is absent, and thus $Z_4$ is connected to $Z_2$, $Z_3$ or the C atom connected to $Z_1$ on the aromatic ring, and the $Z_2$ and the C atom on the aromatic ring that are connected to $Z_1$ are connected to R respectively; or $Z_1$, $Z_2$ and $Z_3$ are all absent, and thus $Z_4$ is connected to one of the C atoms connected to $Z_1$ or $Z_3$ on the aromatic ring, and the other C atom on the aromatic ring is connected to R;

$Z_2$ is O, S, N or C atom, which is optionally substituted with one or two $R_{Z2}$;

$Z_3$ is O, S, N or C atom, which is optionally substituted with one or two $R_{Z3}$; with the proviso that when ═ represents double bond, $Z_2$ is N or C atom, and $Z_3$ is N or C atom;

$Z_4$ is N or $CR_{Z4}$;

$Z_5$ is N or $CR_{Z5}$;

$R_a$, $R_b$ and $R_c$ are independently H, halogen, OR', NR'R", $C_{1-6}$ alkyl or $C_{1-6}$ haloalkyl; or $R_a$ and $R_b$ are taken together with the carbon atom to which they are attached to form C═O, $C_{3-7}$ cycloalkyl or 4- to 8-membered heterocyclyl; or $R_a$ and $R_c$ are taken together with the carbon atoms to which they are attached to form $C_{3-7}$ cycloalkyl or 4- to 8-membered heterocyclyl; or $R_a$ and $R_c$ are taken together to form bond;

$R_{N1}$ is H, $C_{1-6}$ alkyl or $C_{1-6}$ haloalkyl;

$R_{Z1}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z1}$ are taken together with $Z_1$ to form C═O, $C_{3-7}$ cycloalkyl or 4- to 8-membered heterocyclyl;

$R_{Z2}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z2}$ are taken together with $Z_2$ to form C═O, $C_{3-7}$ cycloalkyl or 4- to 8-membered heterocyclyl;

$R_{Z3}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z3}$ are taken together with $Z_3$ to form C═O, $C_{3-7}$ cycloalkyl or 4- to 8-membered heterocyclyl;

$R_{Z4}$ is H, CN, halogen, —$(CH_2)_{0-5}$—OR', —$(CH_2)_{0-5}$—NR'R", $C_{1-6}$ alkyl or $C_{1-6}$ haloalkyl;

$R_{Z5}$ is H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl;

or the ring where $Z_4$ is located is absent;

wherein R is H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl, —$(CH_2)_{0-5}$-4- to 8-membered heterocyclyl, $C_{2-6}$ alkenyl, $C_{2-6}$ alkynyl, —$(CH_2)_{0-5}$—$C_{3-10}$ halocycloalkyl, —$(CH_2)_{0-5}$—$C_{6-10}$ aryl or —$(CH_2)_{0-5}$-5- to 14-membered heteroaryl;

R' is H, $C_{1-6}$ alkyl, $C_{1-6}$ haloalkyl or —$(CH_2)_{0-5}$—$C_{3-7}$ cycloalkyl;

R" is H, $C_{1-6}$ alkyl or $C_{1-6}$ haloalkyl;

$L_1$ is selected from bond, —O—, —$S(O)_p$—, —$S(O)(═NR^*)$—, —$NR^\#$—, —$CR^\#R^{\#'}$—, —$C_aR^\#R^{\#'}$—$C_bR^\#R^{\#'}$—, —N═S(O)(R*)— or —S(O)(R*)═N—;

$L_2$ is selected from bond, —O—, —$S(O)_p$—, —$S(O)(═NR^*)$—, —$NR^\#$—, —$CR^\#R^{\#'}$—, —$C_aR^\#R^{\#'}$—$C_bR^\#R^{\#'}$—, —N═S(O)(R*)— or —S(O)(R*)═N—;

wherein one of $C_aR^\#R^{\#'}$ and $C_bR^\#R^{\#'}$ can be replaced by O, $S(O)_p$, $S(O)(═NR^*)$ or $NR^\#$, and when one of $C_aR^\#R^{\#'}$ and $C_bR^\#R^{\#'}$ is replaced by O, S or $NR^\#$, the other of $C_aR^\#R^{\#'}$ and $C_bR^\#R^{\#'}$ can further be replaced by $S(O)_q$;

E is independently selected from: bond, —$C_cR^\#R^{\#'}$—$C_dR^\#R^{\#'}$—$C_eR^\#R^{\#'}$,

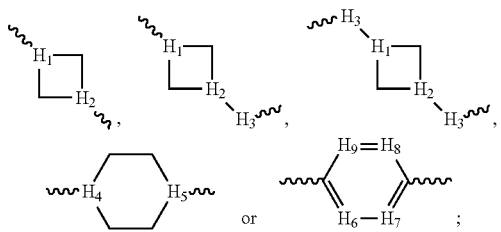

wherein one of $C_cR^\#R^{\#'}$, $C_dR^\#R^{\#'}$ or $C_eR^\#R^{\#'}$, or both of $C_cR^\#R^{\#'}$ and $C_eR^\#R^{\#'}$ can be replaced by O, $S(O)_p$, $S(O)(═NR^*)$ or $NR^\#$, and when one of $C_cR^\#R^{\#'}$, $C_dR^\#R^{\#'}$ or $C_eR^\#R^{\#'}$ is replaced by O, S or $NR^\#$, the other one or two of $C_cR^\#R^{\#'}$, $C_dR^\#R^{\#'}$ or $C_eR^\#R^{\#'}$ adjacent to it can further be replaced by $S(O)_q$;

or two E moieties can be taken together to form —$CH_2CH_2OCH_2CH_2$—, —$OCH_2CH_2CH_2CH_2$—, —$CH_2CH_2CH_2CH_2O$—,

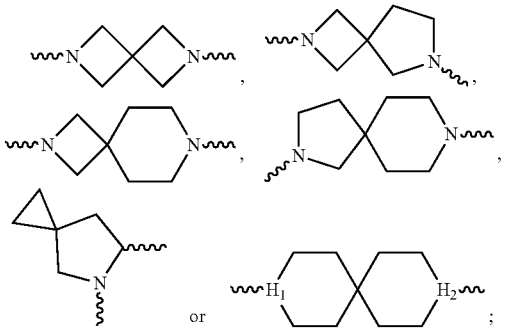

wherein ⁓ represents the point of attachment to $L_1$ or $L_2$;

$H_1$ and $H_2$ are N or C atom, $H_3$ is O, S, N or C atom, and $H_1$ and $H_3$, and $H_2$ and $H_3$ are not heteroatoms at the same time;

$H_4$ and $H_5$ are N or C atom;

$H_6$, $H_7$, $H_8$ and $H_9$ are C or N atom;

p is 0, 1 or 2;

q is 1 or 2;

R* is H, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ halocycloalkyl, 3- to 10-membered heterocyclyl, $C_{6-10}$ aryl or 5- to 14-membered heteroaryl;

$R^\#$ is H, halogen, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ halocycloalkyl, 3- to 10-membered heterocyclyl, $C_{6-10}$ aryl or 5- to 14-membered heteroaryl;

$R^{\#'}$ is H, halogen, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ halocycloalkyl, 3- to 10-membered heterocyclyl, $C_{6-10}$ aryl or 5- to 14-membered heteroaryl;

or, $R^{\#}$ and $R^{\#}$ on adjacent atoms can be taken together to form bond, and $R^{\#'}$ and $R^{\#'}$ on adjacent atoms can be taken together to form bond;

or, $R^{\#}$ and $R^{\#'}$ on the same or different atoms can be taken together to form —O, or $C_{3-7}$ cycloalkyl, 4- to 8-membered heterocyclyl, $C_{6-10}$ aryl or 5- to 6-membered heteroaryl, wherein the $C_{3-7}$ cycloalkyl, 4- to 8-membered heterocyclyl, $C_{6-10}$ aryl or 5- to 6-membered heteroaryl is optionally substituted with Rx, and the Rx is H, CN, halogen, $C_{1-6}$ alkyl or $C_{1-6}$ haloalkyl;

m is 0, 1, 2, 3, 4, 5, 6, 7, 8, 9 or 10;

$X_1$ is C or N atom;

$X_2$ is C or N atom;

$X_3$ is C or N atom;

$X_4$ is O, S, C or N atom, which is optionally substituted with one or two $R_2$;

$X_5$ is O, S, C or N atom;

$X_6$ is C or N atom;

$X_7$ is O, S, C or N atom;

$R_1$ is H, CN, halogen, —$(CH_2)_{0-5}$—OR', —$(CH_2)_{0-5}$—NR'R'', $C_{1-6}$ alkyl, $C_{1-6}$ haloalkyl, $C_{2-6}$ alkenyl, $C_{2-6}$ alkynyl, —$(CH_2)_{0-5}$—$C_{3-7}$ cycloalkyl, —$(CH_2)_{0-5}$—$C_{3-10}$ halocycloalkyl, —$(CH_2)_{0-5}$-4- to 8-membered heterocyclyl, —$(CH_2)_{0-5}$—$C_{6-10}$ aryl, —$(CH_2)_{0-5}$-5- to 14-membered heteroaryl, —C(O)R, —S(O)R or —S(O)$_2$R;

$R_2$ is H, CN, halogen, —$(CH_2)_{0-5}$—OR', —$(CH_2)_{0-5}$—NR'R'', $C_{1-6}$ alkyl, $C_{1-6}$ haloalkyl, $C_{2-6}$ alkenyl, $C_{2-6}$ alkynyl, —$(CH_2)_{0-5}$—$C_{3-7}$ cycloalkyl, —$(CH_2)_{0-5}$—$C_{3-10}$ halocycloalkyl, —$(CH_2)_{0-5}$-4- to 8-membered heterocyclyl, —$(CH_2)_{0-5}$—$C_{6-10}$ aryl, —$(CH_2)_{0-5}$-5- to 14-membered heteroaryl, —C(O)R, —S(O)R or —S(O)$_2$R;

$R_{N2}$ is H, $C_{1-6}$ alkyl or $C_{1-6}$ haloalkyl;

the definition of $L_1'$ is the same as that of $L_1$;

the definition of $L_2'$ is the same as that of $L_2$;

the definition of E' is the same as that of E;

the definition of m' is the same as that of m;

$R_{s1}$ is selected from H, CN, halogen, —$(CH_2)_{0-5}$—OR', —$(CH_2)_{0-5}$—NR'R'', $C_{1-6}$ alkyl, $C_{1-6}$ haloalkyl, —$(CH_2)_{0-5}$-4- to 8-membered heterocyclyl, $C_{2-6}$ alkenyl, $C_{2-6}$ alkynyl, —$(CH_2)_{0-5}$—$C_{3-7}$ cycloalkyl, —$(CH_2)_{0-5}$—$C_{3-10}$ halocycloalkyl, —$(CH_2)_{0-5}$—$C_{6-10}$ aryl, —$(CH_2)_{0-5}$-5- to 14-membered heteroaryl, —C(O)R, —S(O)R or —S(O)$_2$R;

$R_{s2}$ is selected from H, CN, halogen, $C_{1-6}$ alkyl, $C_{1-6}$ haloalkyl, $C_{2-6}$ alkenyl, $C_{2-6}$ alkynyl, —$(CH_2)_{0-5}$—OR', —$(CH_2)_{0-5}$—NR'R'', —$(CH_2)_{0-5}$—$C_{3-7}$ cycloalkyl, —$(CH_2)_{0-5}$—$C_{3-10}$ halocycloalkyl, —$(CH_2)_{0-5}$-4- to 8-membered heterocyclyl, —$(CH_2)_{0-5}$—$C_{6-10}$ aryl, —$(CH_2)_{0-5}$-5- to 14-membered heteroaryl, —C(O)R, —S(O)R or —S(O)$_2$R;

$R_{s3}$ is selected from H, CN, halogen, —$(CH_2)_{0-5}$—OR', —$(CH_2)_{0-5}$—NR'R'', $C_{1-6}$ alkyl, $C_{1-6}$ haloalkyl, —$(CH_2)_{0-5}$—$C_{3-7}$ cycloalkyl, —$(CH_2)_{0-5}$-4- to 8-membered heterocyclyl, $C_{2-6}$ alkenyl, $C_{2-6}$ alkynyl, —$(CH_2)_{0-5}$—$C_{3-10}$ halocycloalkyl, —$(CH_2)_{0-5}$—$C_{6-10}$ aryl, —$(CH_2)_{0-5}$-5- to 14-membered heteroaryl, —C(O)R, —S(O)R or —S(O)$_2$R;

$R_{s4}$ is selected from H, CN, halogen, $C_{1-6}$ alkyl, $C_{1-6}$ haloalkyl, $C_{2-6}$ alkenyl, $C_{2-6}$ alkynyl, —$(CH_2)_{0-5}$—OR', —$(CH_2)_{0-5}$—NR'R'', —$(CH_2)_{0-5}$—$C_{3-7}$ cycloalkyl, —$(CH_2)_{0-5}$-4- to 8-membered heterocyclyl, —$(CH_2)_{0-5}$—$C_{3-10}$ halocycloalkyl, —$(CH_2)_{0-5}$—$C_{6-10}$ aryl, —$(CH_2)_{0-5}$-5- to 14-membered heteroaryl, —C(O)R, —S(O)R or —S(O)$_2$R;

s1 is 0, 1, 2 or 3;

s2 is 0, 1, 2 or 3;

s3 is 0, 1 or 2;

s4 is 0, 1, 2, 3, 4 or 5;

the groups containing OH, NH, $NH_2$, CH, $CH_2$, or $CH_3$ in $L_1$, E, $L_2$, $L_1'$, E', $L_2'$, or the above alkyl, alkylene, haloalkyl, alkenyl, alkynyl, cycloalkyl, halocycloalkyl, heterocyclyl, aryl, and heteroaryl are each optionally substituted with 1, 2, 3 or more $R^s$ at each occurrence, wherein the $R^s$ is independently selected from the following groups at each occurrence: halogen, hydroxyl, amino, cyano, nitro, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ halocycloalkyl, 3- to 10-membered heterocyclyl, $C_{6-10}$ aryl, 5- to 14-membered heteroaryl, $C_{6-12}$ aralkyl, —$OR^{a'}$, —$OC(O)R^{a'}$, —$C(O)R^{a'}$, —$C(O)OR^{a'}$, —$C(O)NR^{a'}R^{b'}$, —$S(O)_nR^{a'}$, —$S(O)_nOR^{a'}$, —$S(O)_nNR^{a'}R^{b'}$, —$NR^{a'}R^{b'}$, —$NR^{a'}C(O)R^{b'}$, —$NR^{a'}$—$C(O)OR^{b'}$, —$NR^{a'}$—$S(O)$ n-$R^{b'}$, —$NR^{a'}C(O)NR^{a'}R^{b'}$, —$C_{1-6}$ alkylene-$R^{a'}$, —$C_{1-6}$ alkylene-$OR^{a'}$, —$C_{1-6}$ alkylene-$OC(O)R^{a'}$, —$C_{1-6}$ alkylene-$C(O)OR^{a'}$, —$C_{1-6}$ alkylene-$S(O)_nR^{a'}$, —$C_{1-6}$ alkylene-$S(O)_nOR^{a'}$, —$C_{1-6}$ alkylene-$OC(O)NR^{a'}R^{b'}$, —$C_{1-6}$ alkylene-$C(O)NR^{a'}R^{b'}$, —$C_{1-6}$ alkylene-$NR^{a'}$—$C(O)NR^{a'}R^{b'}$, —$C_{1-6}$ alkylene-$OS(O)_nR^{a'}$, —$C_{1-6}$ alkylene-$S(O)_nNR^{a'}R^{b'}$, —$C_{1-6}$ alkylene-$NR^{a'}$—$S(O)_nNR^{a'}R^{b'}$, —$C_{1-6}$ alkylene-$NR^{a'}R^{b'}$ and —O—$C_{1-6}$ alkylene-$NR^{a'}R^{b'}$, and wherein the hydroxyl, amino, alkyl, alkylene, cycloalkyl, heterocyclyl, aryl, heteroaryl and aralkyl described with respect to the substituent $R^s$ are further optionally substituted with 1, 2, 3 or more substituents independently selected from: halogen, OH, amino, cyano, nitro, $C_{1-6}$ alkyl, $C_{1-6}$ haloalkyl, $C_{1-6}$ alkyl hydroxyl, $C_{3-6}$ cycloalkyl, 3- to 10-membered heterocyclyl, $C_{6-10}$ aryl, 5- to 14-membered heteroaryl and $C_{6-12}$ aralkyl;

n is independently 1 or 2 at each occurrence;

$R^{a'}$ and $R^{b'}$ are each independently selected from H, $C_{1-6}$ alkyl, $C_{2-6}$ alkenyl, $C_{2-6}$ alkynyl, $C_{1-6}$ alkyl-O—, $C_{1-6}$ alkyl-S—, $C_{3-10}$ cycloalkyl, 3- to 10-membered heterocyclyl, $C_{6-10}$ aryl, 5- to 14-membered heteroaryl and $C_{6-12}$ aralkyl at each occurrence.

In another aspect, the present disclosure provides a pharmaceutical composition comprising a compound disclosed herein, and optionally a pharmaceutically acceptable excipient.

In another aspect, the present disclosure provides a pharmaceutical composition comprising a compound disclosed herein and a pharmaceutically acceptable excipient, which further comprises other therapeutic agent(s).

In another aspect, the present disclosure provides a kit comprising a compound disclosed herein, other therapeutic agent(s), and a pharmaceutically acceptable carrier, adjuvant or vehicle.

In another aspect, the present disclosure provides a use of a compound disclosed herein in the manufacture of a medicament for treating and/or preventing a disease mediated by EGFR kinase.

In another aspect, the present disclosure provides a method of treating and/or preventing a disease mediated by EGFR kinase in a subject, comprising administering to the subject a compound disclosed herein or a composition disclosed herein.

In another aspect, the present disclosure provides a compound disclosed herein or a composition disclosed herein, for use in treating and/or preventing a disease mediated by EGFR kinase.

In a specific embodiment, the diseases treated by the present disclosure include cancer, such as ovarian cancer, cervical cancer, colorectal cancer, breast cancer, pancreatic cancer, glioma, glioblastoma, melanoma, prostate cancer, leukemia, lymphoma, non-Hodgkin's lymphoma, gastric cancer, lung cancer, hepatocellular cancer, stomach cancer, gastrointestinal stromal tumor (GIST), thyroid cancer, cancer of bile duct, endometrial cancer, kidney cancer, anaplastic large cell lymphoma, acute myeloid leukemia (AML), multiple myeloma, melanoma, and mesothelioma.

Other objects and advantages of the present disclosure will be apparent to those skilled in the art from specific embodiments, examples and claims below.

BRIEF DESCRIPTION OF THE DRAWINGS

FIG. 1 shows the effect of compound D3 disclosed herein on the protein level of mutant EGFR$^{L858R/T790M/C797S}$.

DEFINITION

Chemical Definitions

Definitions of specific functional groups and chemical terms are described in more detail below.

When a range of values is listed, it is intended to encompass each value and sub-range within the range. For example, "$C_{1-6}$ alkyl" is intended to include $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

"$C_{1-6}$ alkyl" refers to a radical of a straight or branched, saturated hydrocarbon group having 1 to 6 carbon atoms. In some embodiments, $C_{1-4}$ alkyl is alternative. Examples of $C_{1-6}$ alkyl include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentyl ($C_5$), pentyl ($C_5$), neopentyl ($C_5$), 3-methyl-2-butyl ($C_5$), tert-pentyl ($C_5$) and n-hexyl ($C_6$). The term "$C_{1-6}$ alkyl" also includes heteroalkyl, wherein one or more (e.g., 1, 2, 3 or 4) carbon atoms are substituted with heteroatoms (e.g., oxygen, sulfur, nitrogen, boron, silicon, phosphorus). Alkyl groups can be optionally substituted with one or more substituents, for example, with 1 to 5 substituents, 1 to 3 substituents or 1 substituent. Conventional abbreviations of alkyl include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$) or i-Bu (—$CH_2CH(CH_3)_2$).

"$C_{2-6}$ alkenyl" refers to a radical of a straight or branched hydrocarbon group having 2 to 6 carbon atoms and at least one carbon-carbon double bond. In some embodiments, $C_{2-4}$ alkenyl is alternative. Examples of $C_{2-6}$ alkenyl include vinyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), etc. The term "$C_{2-6}$ alkenyl" also includes heteroalkenyl, wherein one or more (e.g., 1, 2, 3 or 4) carbon atoms are replaced by heteroatoms (e.g., oxygen, sulfur, nitrogen, boron, silicon, phosphorus). The alkenyl groups can be optionally substituted with one or more substituents, for example, with 1 to 5 substituents, 1 to 3 substituents or 1 substituent.

"$C_{2-6}$ alkynyl" refers to a radical of a straight or branched hydrocarbon group having 2 to 6 carbon atoms, at least one carbon-carbon triple bond and optionally one or more carbon-carbon double bonds. In some embodiments, $C_{2-4}$ alkynyl is alternative. Examples of $C_{2-6}$ alkynyl include, but are not limited to, ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$), etc. The term "$C_{2-6}$ alkynyl" also includes heteroalkynyl, wherein one or more (e.g., 1, 2, 3 or 4) carbon atoms are replaced by heteroatoms (e.g., oxygen, sulfur, nitrogen, boron, silicon, phosphorus). The alkynyl groups can be substituted with one or more substituents, for example, with 1 to 5 substituents, 1 to 3 substituents or 1 substituent.

"Halo" or "halogen" refers to fluorine (F), chlorine (Cl), bromine (Br) and iodine (I).

Thus, "$C_{1-6}$ haloalkyl" refers to the above "$C_{1-6}$ alkyl", which is substituted with one or more halogen. In some embodiments, $C_{1-4}$ haloalkyl is yet alternative, and still alternatively $C_{1-2}$ haloalkyl. Exemplary haloalkyl groups include, but are not limited to, —$CF_3$, —$CH_2F$, —$CHF_2$, —$CHFCH_2F$, —$CH_2CHF_2$, —$CF_2CF_3$, —$CCl_3$, —$CH_2Cl$, —$CHCl_2$, 2,2,2-trifluoro-1,1-dimethyl-ethyl, and the like. The haloalkyl can be substituted at any available point of attachment, for example, with 1 to 5 substituents, 1 to 3 substituents or 1 substituent.

"$C_{3-10}$ cycloalkyl" refers to a radical of a non-aromatic cyclic hydrocarbon group having from 3 to 10 ring carbon atoms and zero heteroatoms. In some embodiments, $C_{3-7}$ cycloalkyl and $C_{3-6}$ cycloalkyl are yet alternative, and still alternatively $C_{5-6}$ cycloalkyl. The cycloalkyl also includes a ring system in which the cycloalkyl described herein is fused with one or more aryl or heteroaryl groups, wherein the point of attachment is on the cycloalkyl ring, and in such case, the number of carbon atoms continues to represent the number of carbon atoms in the cycloalkyl system. Exemplary cycloalkyl groups include, but are not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), etc. The cycloalkyl can be substituted with one or more substituents, for example, with 1 to 5 substituents, 1 to 3 substituents or 1 substituent.

"$C_{3-10}$ halocycloalkyl" refers to the above "$C_{3-10}$ cycloalkyl", which is substituted with one or more halogen.

"3- to 12-membered heterocyclyl" refers to a radical of 3- to 12-membered non-aromatic ring system having ring carbon atoms and 1 to 5 ring heteroatoms, wherein each of the heteroatoms is independently selected from nitrogen, oxygen, sulfur, boron, phosphorus and silicon. In the heterocyclyl containing one or more nitrogen atoms, the point of attachment can be a carbon or nitrogen atom as long as the valence permits. In some embodiments, 4- to 12-membered heterocyclyl is alternative, which is a radical of 4- to 12-membered non-aromatic ring system having ring carbon atoms and 1 to 5 ring heteroatoms. In some embodiments, 3- to 10-membered heterocyclyl is alternative, which is a radical of 3- to 10-membered non-aromatic ring system having ring carbon atoms and 1 to 5 ring heteroatoms. In some embodiments, 3- to 8-membered heterocyclyl is alternative, which is a radical of 3- to 8-membered non-aromatic ring system having ring carbon atoms and 1 to 4 ring heteroatoms. 3- to 6-membered heterocyclyl is alternative, which is a radical of 3- to 6-membered non-aromatic ring system having ring carbon atoms and 1 to 3 ring heteroatoms. 4- to 8-membered heterocyclyl is alternative, which is a radical of 4- to 8-membered non-aromatic ring system having ring carbon atoms and 1 to 3 ring heteroatoms. 5- to 6-membered heterocyclyl is more alternative, which is a radical of 5- to 6-membered non-aromatic ring system having ring carbon atoms and 1 to 3 ring heteroatoms. The heterocyclyl also includes a ring system wherein the heterocyclyl described above is fused with one or more cycloalkyl groups, wherein the point of attachment is on the cycloalkyl ring, or the heterocyclyl described above is fused with one or more aryl or heteroaryl groups, wherein the point of attachment is on the heterocyclyl ring; and in such cases, the number of ring members continues to represent the number of ring members in the heterocyclyl ring system. Exemplary 3-membered heterocyclyl groups containing one heteroatom include, but are not limited to, aziridinyl, oxiranyl and thiorenyl. Exemplary 4-membered heterocyclyl groups containing one heteroatom include, but are not limited to, azetidinyl, oxetanyl and thietanyl. Exemplary 5-membered heterocyclyl groups containing one heteroatom include, but are not limited to, tetrahydrofuranyl, dihydrofuranyl, tetrahydrothiophenyl, dihydrothienyl, pyrrolidinyl, dihydropyrrolyl and pyrrolyl-2,5-dione. Exemplary 5-membered heterocyclyl groups containing two heteroatoms include, but are not limited to, dioxolanyl, oxasulfuranyl, disulfuranyl, and oxazolidin-2-one. Exemplary 5-membered heterocyclyl groups containing three heteroatoms include, but are not limited to, triazolinyl, oxadiazolinyl, and thiadiazolinyl. Exemplary 6-membered heterocyclyl groups containing one heteroatom include, but are not limited to, piperidyl, tetrahydropyranyl, dihydropyridyl and thianyl. Exemplary 6-membered heterocyclyl groups containing two heteroatoms include, but are not limited to, piperazinyl, morpholinyl, dithianyl and dioxanyl. Exemplary 6-membered heterocyclyl groups containing three heteroatoms include, but are not limited to, triazinanyl. Exemplary 7-membered heterocycly groups containing one heteroatom include, but are not limited to, azepanyl, oxepanyl and thiepanyl. Exemplary 5-membered heterocyclyl groups fused with a $C_6$ aryl (also referred as 5,6-bicyclic heterocyclyl herein) include, but are not limited to, indolinyl, isoindolinyl, dihydrobenzofuranyl, dihydrobenzothiophenyl, benzoxazolinonyl, etc. Exemplary 6-membered heterocyclyl groups fused with a $C_6$ aryl (also referred as 6,6-bicyclic heterocyclyl herein) include, but are not limited to, tetrahydroquinolinyl, tetrahydroisoquinolinyl, etc. The heterocyclyl can be substituted with one or more substituents, for example, with 1 to 5 substituents, 1 to 3 substituents or 1 substituent.

"4- to 12-membered heterocyclylene" and "5- to 6-membered heterocyclylene" refer to the above "4- to 12-membered heterocyclyl" and "5- to 6-membered heterocyclyl", respectively, wherein another hydrogen is removed and formed divalent groups, and can be substituted or unsubstituted.

"$C_{6-10}$ aryl" refers to a radical of monocyclic or polycyclic (e.g., bicyclic) 4n+2 aromatic ring system having 6-10 ring carbon atoms and zero heteroatoms (e.g., having 6 or 10 shared π electrons in a cyclic array). In some embodiments, the aryl group has six ring carbon atoms ("$C_6$ aryl"; for example, phenyl). In some embodiments, the aryl group has ten ring carbon atoms ("$C_{10}$ aryl"; for example, naphthyl, e.g., 1-naphthyl and 2-naphthyl). The aryl group also includes a ring system in which the aryl ring described above is fused with one or more cycloalkyl or heterocyclyl groups, and the point of attachment is on the aryl ring, in which case the number of carbon atoms continues to represent the number of carbon atoms in the aryl ring system. The aryl can be substituted with one or more substituents, for example, with 1 to 5 substituents, 1 to 3 substituents or 1 substituent.

"$C_{6-12}$ aralkyl" refers to the group —R—R', wherein R is alkyl, R' is aryl, and alkyl and aryl have a total of 6-12 carbon atoms.

"5- to 14-membered heteroaryl" refers to a radical of 5- to 14-membered monocyclic or bicyclic 4n+2 aromatic ring system (e.g., having 6, 10 or 14 shared π electrons in a cyclic array) having ring carbon atoms and 1-4 ring heteroatoms, wherein each heteroatom is independently selected from nitrogen, oxygen and sulfur. In the heteroaryl group containing one or more nitrogen atoms, the point of attachment can be a carbon or nitrogen atom as long as the valence permits. Heteroaryl bicyclic systems may include one or more heteroatoms in one or two rings. Heteroaryl also includes ring systems wherein the heteroaryl ring described above is fused with one or more cycloalkyl or heterocyclyl groups, and the point of attachment is on the heteroaryl ring. In such case, the number the carbon atoms continues to represent the number of carbon atoms in the heteroaryl ring system. In some embodiments, 5- to 10-membered heteroaryl groups are alternative, which are radicals of 5- to 10-membered monocyclic or bicyclic 4n+2 aromatic ring systems having ring carbon atoms and 1-4 ring heteroatoms. In other embodiments, 5- to 6-membered heteroaryl groups are yet alternative, which are radicals of 5- to 6-membered monocyclic or bicyclic 4n+2 aromatic ring systems having ring carbon atoms and 1-4 ring heteroatoms. Exemplary 5-membered heteroaryl groups containing one heteroatom include, but are not limited to, pyrrolyl, furyl and thienyl. Exemplary 5-membered heteroaryl groups containing two heteroatoms include, but are not limited to, imidazolyl, pyrazolyl, oxazolyl, isoxazolyl, thiazolyl, and isothiazolyl. Exemplary 5-membered heteroaryl groups containing three heteroatoms include, but are not limited to, triazolyl, oxadiazolyl (such as, 1,2,4-oxadiazoly), and thiadiazolyl. Exemplary 5-membered heteroaryl groups containing four heteroatoms include, but are not limited to, tetrazolyl. Exemplary 6-membered heteroaryl groups containing one heteroatom include, but are not limited to, pyridyl. Exemplary 6-membered heteroaryl groups containing two heteroatoms include, but are not limited to, pyridazinyl, pyrimidinyl, and pyrazinyl. Exemplary 6-membered heteroaryl groups containing three or four heteroatoms include, but are not limited to, triazinyl and tetrazinyl, respectively. Exemplary 7-membered heteroaryl groups containing one heteroatom include, but are not limited to, azepinyl, oxepinyl, and thiepinyl. Exemplary 5,6-bicyclic heteroaryl groups include, but are not limited to, indolyl, isoindolyl, indazolyl, benzotriazolyl, benzothiophenyl, isobenzothiophenyl, benzofuranyl, benzoisofuranyl, benzimidazolyl, benzoxazolyl, benzoisoxazolyl, benzoxadiazolyl, benzothiazolyl, benzoisothiazolyl, benzothiadiazolyl, indolizinyl and purinyl. Exemplary 6,6-bicyclic heteroaryl groups include, but are not limited to, naphthyridinyl, pteridinyl, quinolyl, isoquinolyl, cinnolinyl, quinoxalinyl, phthalazinyl and quinazolinyl. The heteroaryl can be substituted with one or more substituents, for example, with 1 to 5 substituents, 1 to 3 substituents or 1 substituent.

"Oxo" represents =O.

Alkyl, alkenyl, alkynyl, cycloalkyl, heterocyclyl, aryl and heteroaryl as defined herein are optionally substituted groups.

Exemplary substituents on carbon atoms include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR)R$^{bb}$, —SH, —SR$^{aa}$, —SSR$^{cc}$, —C(=O)R$^{aa}$, —CO$_2$H, —CHO, —C(OR)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O) SR$^{aa}$, —C(=S)SR$^{aa}$, —SC(=S)SR$^{aa}$, —SC(=O) SR$^{aa}$, —OC(=O) SR$^{aa}$, —SC(=O) OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR")$_2$, —P(=O)$_2$N(R$_b$)$_2$, —OP(=O)$_2$N(R$_b$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), alkyl, haloalkyl, alkenyl, alkynyl, cycloalkyl, heterocyclyl, aryl and heteroaryl, wherein each of the alkyl, alkenyl, alkynyl, cycloalkyl, heterocyclyl, aryl and heteroaryl is independently substituted with 0, 1, 2, 3, 4 or 5 R$^{dd}$ groups;

or two geminal hydrogen on a carbon atom are replaced with =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, —NR$^{bb}$ or =NOR groups;

each of the R$^{aa}$ is independently selected from alkyl, haloalkyl, alkenyl, alkynyl, cycloalkyl, heterocyclyl, aryl and heteroaryl, or two of the R$^{aa}$ groups are combined to form a heterocyclyl or heteroaryl ring, wherein each of the alkyl, alkenyl, alkynyl, cycloalkyl, heterocyclyl, aryl and heteroaryl is independently substituted with 0, 1, 2, 3, 4 or 5 R$^{dd}$ groups;

each of the R$^{bb}$ is independently selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, haloalkyl, alkenyl, alkynyl, cycloalkyl, heterocyclyl, aryl and heteroaryl, or two R$^{bb}$ groups are combined to form a heterocyclyl or a heteroaryl ring, wherein each of the alkyl, alkenyl, alkynyl, cycloalkyl, heterocyclyl, aryl and heteroaryl is independently substituted with 0, 1, 2, 3, 4 or 5 R$^{dd}$ groups;

each of the Roc is independently selected from hydrogen, alkyl, haloalkyl, alkenyl, alkynyl, cycloalkyl, heterocyclyl, aryl and heteroaryl, or two R$^{cc}$ groups are combined to form a heterocyclyl or a heteroaryl ring, wherein each of the alkyl, alkenyl, alkynyl, cycloalkyl, heterocyclyl, aryl and heteroaryl is independently substituted with 0, 1, 2, 3, 4 or 5 R$^{dd}$ groups;

each of the R$^{dd}$ is independently selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, alkyl, haloalkyl, alkenyl, alkynyl, cycloalkyl, heterocyclyl, aryl, heteroaryl, wherein each of the alkyl, alkenyl, alkynyl, cycloalkyl, heterocyclyl, aryl and heteroaryl is independently substituted with 0, 1, 2, 3, 4 or 5 R$^{gg}$ groups, or two geminal R$^{dd}$ substituents can be combined to form —O or =S;

each of the R$^{ee}$ is independently selected from alkyl, haloalkyl, alkenyl, alkynyl, cycloalkyl, aryl, heterocyclyl, and heteroaryl, wherein each of the alkyl, alkenyl, alkynyl, cycloalkyl, heterocyclyl, aryl and heteroaryl is independently substituted with 0, 1, 2, 3, 4 or 5 R$^{gg}$ groups;

each of the R$^{ff}$ is independently selected from hydrogen, alkyl, haloalkyl, alkenyl, alkynyl, cycloalkyl, heterocyclyl, aryl and heteroaryl, or two R$^{ff}$ groups are combined to form a heterocyclyl or a heteroaryl ring, wherein each of the alkyl, alkenyl, alkynyl, cycloalkyl, heterocyclyl, aryl and heteroaryl is independently substituted with 0, 1, 2, 3, 4 or 5 R$^{gg}$ groups;

each of the R$^{gg}$ is independently selected from halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl) C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ haloalkyl, C$_2$-C$_6$ alkenyl, C$_2$-C$_6$ alkynyl, C$_3$-C$_7$ cycloalkyl, C$_6$-C$_{10}$ aryl, C$_3$-C$_7$ heterocyclyl, C$_5$-C$_{10}$ heteroaryl; or two geminal R$^{gg}$ substituents may combine to form =O or =S; wherein X$^-$ is a counterion.

Exemplary substituents on nitrogen atoms include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, haloalkyl, alkenyl, alkynyl, cycloalkyl, heterocyclyl, aryl and heteroaryl, or two Rec groups attached to a nitrogen atom combine to form a heterocyclyl or a heteroaryl ring, wherein each of the alkyl, alkenyl, alkynyl, cycloalkyl, heterocyclyl, aryl and heteroaryl is independently substituted with 0, 1, 2, 3, 4 or 5 R$^{dd}$ groups, and wherein R$^{aa}$, R$^{bb}$, Roc and R$^{dd}$ are as described herein.

Other Definitions

The term "cancer" includes, but is not limited to, the following cancers: breast, ovary, cervix, prostate, testis, esophagus, stomach, skin, lung, bone, colon, pancreas, thyroid, biliary tract, buccal cavity and pharynx (mouth), lips, tongue, oral cavity, pharynx, small intestine, colorectal, large intestine, rectum, cancer of brain and central nervous system, glioblastoma, neuroblastoma, keratoacanthoma, epidermoid carcinoma, large cell carcinoma, adenocarcinoma, adenoma, follicular carcinoma, undifferentiated carcinoma, papillary carcinoma, seminoma, melanoma, sarcoma, bladder cancer, liver cancer, kidney cancer, bone marrow disorder, lymphatic disorder, Hodgkin's disease, hairy cell carcinoma and leukemia.

The term "treating" as used herein relates to reversing, alleviating or inhibiting the progression or prevention of the disorders or conditions to which the term applies, or of one or more symptoms of such disorders or conditions. The noun "treatment" as used herein relates to the action of treating, which is a verb, and the latter is as just defined.

The term "pharmaceutically acceptable salt" as used herein refers to those carboxylate and amino acid addition salts of the compounds of the present disclosure, which are suitable for the contact with patients' tissues within a reliable medical judgment, and do not produce inappropriate toxicity, irritation, allergy, etc. They are commensurate with a reasonable benefit/risk ratio, and are effective for their intended use. The term includes, if possible, the zwitterionic form of the compounds of the disclosure.

The pharmaceutically acceptable base addition salts are formed with metals or amines, such as alkali metal and alkaline earth metal hydroxides or organic amines. Examples of the metals used as cations include sodium, potassium, magnesium, calcium, etc. Examples of suitable amines are N,N'-dibenzylethylenediamine, chloroprocaine, choline, diethanolamine, ethylenediamine, N-methylglucamine and procaine.

The base addition salt of the acidic compound can be prepared by contacting the free acid form with a sufficient amount of the required base to form a salt in a conventional manner. The free acid can be regenerated by contacting the salt form with an acid in a conventional manner and then isolating the free acid. The free acid forms are somewhat different from their respective salt forms in their physical properties, such as solubility in polar solvents. But for the purposes of the present disclosure, the salts are still equivalent to their respective free acids.

The salts can be prepared from the inorganic acids, which include sulfates, pyrosulfates, bisulfates, sulfites, bisulfites, nitrates, phosphates, monohydrogen phosphates, dihydrogen phosphates, metaphosphates, pyrophosphates, chlorides, bromides and iodides. Examples of the acids include hydrochloric acid, nitric acid, sulfuric acid, hydrobromic acid, hydroiodic acid, phosphoric acid, etc. The representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthalate, methanesulfonate, glucoheptanate, lactobionate, lauryl sulfonate, isethionate, etc. The salts can also be prepared from the organic acids, which include aliphatic monocarboxylic and dicarboxylic acids, phenyl-substituted alkanoic acids, hydroxyalkanoic acids, alkanedioic acid, aromatic acids, aliphatic and aromatic sulfonic acids, etc. The representative salts include acetate, propionate, octanoate, isobutyrate, oxalate, malonate, succinate, suberate, sebacate, fumarate, maleate, mandelate, benzoate, chlorobenzoate, methyl benzoate, dinitrobenzoate, naphthoate, besylate, tosylate, phenylacetate, citrate, lactate, maleate, tartrate, methanesulfonate, etc. The pharmaceutically acceptable salts can include cations based on alkali metals and alkaline earth metals, such as sodium, lithium, potassium, calcium, magnesium, etc., as well as non-toxic ammonium, quaternary ammonium, and amine cations including, but not limited to, ammonium, tetramethylammonium, tetraethylammonium, methylamine, dimethylamine, trimethylamine, triethylamine, ethylamine, etc. Salts of amino acids are also included, such as arginine salts, gluconates, galacturonates, etc. (for example, see Berge S. M. et al., "Pharmaceutical Salts," J. Pharm. Sci., 1977; 66:1-19 for reference).

"Subjects" to which administration is contemplated include, but are not limited to, humans (e.g., males or females of any age group, e.g., paediatric subjects (e.g., infants, children, adolescents) or adult subjects (e.g., young adults, middle-aged adults or older adults) and/or non-human animals, such as mammals, e.g., primates (e.g., cynomolgus monkeys, rhesus monkeys), cattle, pigs, horses, sheep, goats, rodents, cats and/or dogs. In some embodiments, the subject is a human. In some embodiments, the subject is a non-human animal. The terms "human", "patient" and "subject" can be used interchangeably herein.

"Disease," "disorder," and "condition" can be used interchangeably herein.

Unless indicated, otherwise the term "treatment" as used herein includes the effect on a subject who is suffering from a particular disease, disorder, or condition, which reduces the severity of the disease, disorder, or condition, or delays or slows the progression of the disease, disorder or condition ("therapeutic treatment"). The term also includes the effect that occurs before the subject begins to suffer from a specific disease, disorder or condition ("prophylactic treatment").

Generally, the "effective amount" of a compound refers to an amount sufficient to elicit a target biological response. As understood by those skilled in the art, the effective amount of the compound of the disclosure can vary depending on the following factors, such as the desired biological endpoint, the pharmacokinetics of the compound, the diseases being treated, the mode of administration, and the age, health status and symptoms of the subjects. The effective amount includes therapeutically effective amount and prophylactically effective amount.

Unless indicated, otherwise the "therapeutically effective amount" of the compound as used herein is an amount sufficient to provide therapeutic benefits in the course of treating a disease, disorder or condition, or to delay or minimize one or more symptoms associated with the disease, disorder or condition. The therapeutically effective amount of a compound refers to the amount of the therapeutic agent that, when used alone or in combination with other therapies, provides a therapeutic benefit in the treatment of a disease, disorder or condition. The term "therapeutically effective amount" can include an amount that improves the overall treatment, reduces or avoids the symptoms or causes of the disease or condition, or enhances the therapeutic effect of other therapeutic agents.

Unless indicated, otherwise the "prophylactically effective amount" of the compound as used herein is an amount sufficient to prevent a disease, disorder or condition, or an amount sufficient to prevent one or more symptoms associated with a disease, disorder or condition, or an amount sufficient to prevent the recurrence of a disease, disorder or condition. The prophylactically effective amount of a compound refers to the amount of a therapeutic agent that, when used alone or in combination with other agents, provides a prophylactic benefit in the prevention of a disease, disorder or condition. The term "prophylactically effective amount" can include an amount that improves the overall prevention, or an amount that enhances the prophylactic effect of other preventive agents.

"Combination" and related terms refer to the simultaneous or sequential administration of the compounds of the present disclosure and other therapeutic agents. For example, the compounds of the present disclosure can be administered simultaneously or sequentially in separate unit dosage with other therapeutic agents, or simultaneously in a single unit dosage with other therapeutic agents.

DETAILED DESCRIPTION OF THE INVENTION

As used herein, the term "compound disclosed herein" refers to the following compounds of formula (I)(including sub general formulas, such as formula (II') etc), or a pharmaceutically acceptable salt, enantiomer, diastereomer, racemate, solvate, hydrate, polymorph, prodrug, or isotopic variant thereof, or a mixture thereof.

In the present disclosure, compounds are named using standard nomenclature. For compounds having an asymmetric center, it should be understood, unless otherwise stated, that all optical isomers and mixtures thereof are included. Furthermore, unless otherwise specified, all isomer compounds and carbon-carbon double bonds included in the present disclosure may occur in the form of Z and E.

Compounds which exist in different tautomeric forms, one of which is not limited to any particular tautomer, but is intended to cover all tautomeric forms.

In one embodiment, the present disclosure relates to a compound of general formula (I), or a pharmaceutically acceptable salt, enantiomer, diastereomer, racemate, solvate, hydrate, polymorph, prodrug, or isotopic variant thereof, or a mixture thereof:

together with the carbon atom to which they are attached to form C—O, $C_{3-7}$ cycloalkyl or 4- to 8-membered heterocyclyl; or, $R_a$ and $R_c$ are taken together with the carbon atoms to which they are attached to form $C_{3-7}$ cycloalkyl or 4- to 8-membered heterocyclyl; or $R_a$ and $R_c$ are taken together to form bond;

$R_{N1}$ is H, $C_{1-6}$ alkyl or $C_{1-6}$ haloalkyl;

$R_{Z1}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z1}$ are taken together with $Z_1$ to form C=O, $C_{3-7}$ cycloalkyl or 4- to 8-membered heterocyclyl;

$R_{Z2}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z2}$ are taken together with $Z_2$ to form C=O, $C_{3-7}$ cycloalkyl or 4- to 8-membered heterocyclyl;

$R_{Z3}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z3}$ are taken together with $Z_3$ to form C=O, $C_{3-7}$ cycloalkyl or 4- to 8-membered heterocyclyl;

$R_{Z4}$ is H, CN, halogen, —$(CH_2)_{0-5}$—OR', —$(CH_2)_{0-5}$—NR'R", $C_{1-6}$ alkyl or $C_{1-6}$ haloalkyl;

$R_{Z5}$ is H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl;

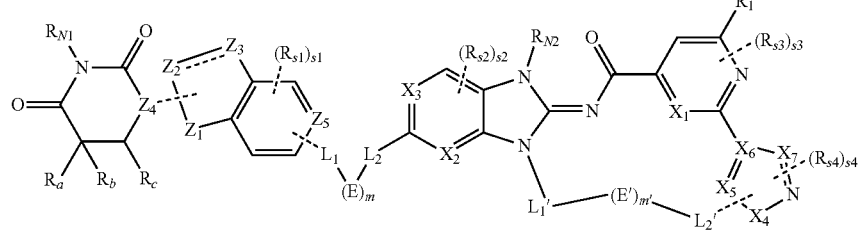

(I)

wherein
═ represents single bond or double bond;
----- represents that the point of attachment to the rest of the molecule can be located at an available point of a ring;
$Z_1$ is O, S, N or C atom, which is optionally substituted with one or two $R_{Z1}$; or $Z_1$ is absent, and thus $Z_4$ is connected to $Z_2$, $Z_3$ or the C atom connected to $Z_1$ on the aromatic ring, and the $Z_2$ and the C atom on the aromatic ring that are connected to $Z_1$ are connected to R respectively; or $Z_1$, $Z_2$ and $Z_3$ are all absent, and thus $Z_4$ is connected to one of the C atoms connected to $Z_1$ or $Z_3$ on the aromatic ring, and the other C atom on the aromatic ring is connected to R;
$Z_2$ is O, S, N or C atom, which is optionally substituted with one or two $R_{Z2}$;
$Z_3$ is O, S, N or C atom, which is optionally substituted with one or two $R_{Z3}$; with the proviso that when ═ represents double bond, $Z_2$ is N or C atom, and $Z_3$ is N or C atom;
$Z_4$ is N or $CR_{Z4}$;
$Z_5$ is N or $CR_{Z5}$;
$R_a$, $R_b$ and $R_c$ are independently H, halogen, OR', NR'R", $C_{1-6}$ alkyl or $C_{1-6}$ haloalkyl; or $R_a$ and $R_b$ are taken or the ring where $Z_4$ is located is absent;
wherein R is H, CN, halogen, —$(CH_2)_{0-5}$—OR', —$(CH_2)_{0-5}$—NR'R", —$C_{1-6}$ alkyl, $C_{1-6}$ haloalkyl, —$(CH_2)_{0-5}$—$C_{3-7}$ cycloalkyl, —$(CH_2)_{0-5}$-4- to 8-membered heterocyclyl, $C_{2-6}$ alkenyl, $C_{2-6}$ alkynyl, —$(CH_2)_{0-5}$—$C_{3-10}$ halocycloalkyl, —$(CH_2)_{0-5}$—$C_{6-10}$ aryl or —$(CH_2)_{0-5}$-5- to 14-membered heteroaryl;
R' is H, $C_{1-6}$ alkyl, $C_{1-6}$ haloalkyl or —$(CH_2)_{0-5}$—$C_{3-7}$ cycloalkyl;
R" is H, $C_{1-6}$ alkyl or $C_{1-6}$ haloalkyl;
$L_1$ is selected from bond, —O—, —$S(O)_p$—, —S(O)(=NR*)—, —$NR^{\#}$—, —$CR^{\#}R^{\#'}$—, —$C_aR^{\#}R^{\#'}$—$C_bR^{\#}R^{\#'}$—, —N=S(O)(R*)— or —S(O)(R*)=N—;
$L_2$ is selected from bond, —O—, —$S(O)_p$—, —S(O)(=NR*)—, —$NR^{\#}$—, —$CR^{\#}R^{\#'}$—, —$C_aR^{\#}R^{\#'}$—$C_bR^{\#}R^{\#'}$—, —N=S(O)(R*)— or —S(O)(R*)=N—;
wherein one of $C_aR^{\#}R^{\#'}$ and $C_bR^{\#}R^{\#'}$ can be replaced by O, $S(O)_p$, S(O)(=NR*) or $NR^{\#}$, and when one of $C_aR^{\#}R^{\#'}$ and $C_bR^{\#}R^{\#'}$ is replaced by O, S or $NR^{\#}$, the other of $C_aR^{\#}R^{\#'}$ and $C_bR^{\#}R^{\#'}$ can further be replaced by $S(O)_q$;
E is independently selected from: bond, —$C_cR^{\#}R^{\#'}$—$C_dR^{\#}R^{\#'}$—$C_eR^{\#}R^{\#'}$,

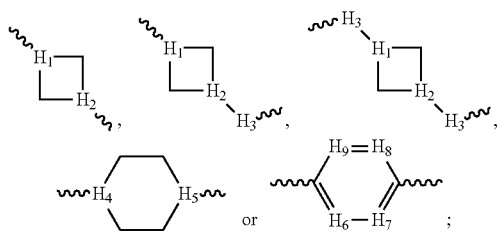

wherein one of $C_cR^\#R^{\#'}$, $C_dR^\#R^{\#'}$ or $C_eR^\#R^{\#'}$, or both of $C_cR^\#R^{\#'}$ and $C_eR^\#R^{\#'}$ can be replaced by O, $S(O)_p$, $S(O)(=NR^*)$ or $NR^\#$, and when one of $C_cR^\#R^{\#'}$, $C_dR^\#R^{\#'}$ or $C_eR^\#R^{\#'}$ is replaced by O, S or $NR^\#$, the other one or two of $C_cR^\#R^{\#'}$, $C_dR^\#R^{\#'}$ or $C_eR^\#R^{\#'}$ adjacent to it can further be replaced by $S(O)_q$;

or two E moieties can be taken together to form —CH$_2$CH$_2$OCH$_2$CH$_2$—, —OCH$_2$CH$_2$CH$_2$CH$_2$—, —CH$_2$CH$_2$CH$_2$CH$_2$O—,

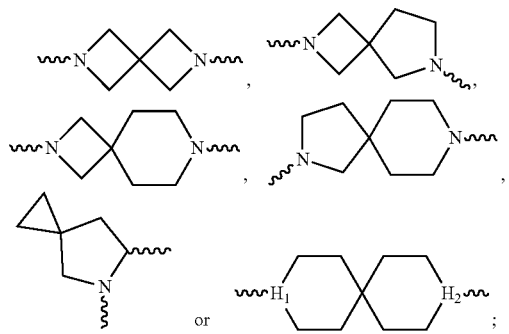

wherein ⁓ represents the point of attachment to $L_1$ or $L_2$;

$H_1$ and $H_2$ are N or C atom, $H_3$ is O, S, N or C atom, and $H_1$ and $H_3$, $H_2$ and $H_3$ are not heteroatoms at the same time;

$H_4$ and $H_5$ are N or C atom;

$H_6$, $H_7$, $H_8$ and $H_9$ are C or N atom;

p is 0, 1 or 2;

q is 1 or 2;

$R^*$ is H, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ halocycloalkyl, 3- to 10-membered heterocyclyl, $C_{6-10}$ aryl or 5- to 14-membered heteroaryl;

$R^\#$ is H, halogen, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ halocycloalkyl, 3- to 10-membered heterocyclyl, $C_{6-10}$ aryl or 5- to 14-membered heteroaryl;

$R^{\#'}$ is H, halogen, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ halocycloalkyl, 3- to 10-membered heterocyclyl, $C_{6-10}$ aryl or 5- to 14-membered heteroaryl;

or, $R^\#$ and $R^\#$ on adjacent atoms can be taken together to form bond, and $R^{\#'}$ and $R^{\#'}$ on adjacent atoms can be taken together to form bond;

or, $R^\#$ and $R^{\#'}$ on the same or different atoms can be taken together to form =O, or $C_{3-7}$ cycloalkyl, 4- to 8-membered heterocyclyl, $C_{6-10}$ aryl or 5- to 6-membered heteroaryl, wherein the $C_{3-7}$ cycloalkyl, 4- to 8-membered heterocyclyl, $C_{6-10}$ aryl or 5- to 6-membered heteroaryl is optionally substituted with Rx, and the Rx is H, CN, halogen, $C_{1-6}$ alkyl or $C_{1-6}$ haloalkyl;

m is 0, 1, 2, 3, 4, 5, 6, 7, 8, 9 or 10;

$X_1$ is C or N atom;

$X_2$ is C or N atom;

$X_3$ is C or N atom;

$X_4$ is O, S, C or N atom, which is optionally substituted with one or two $R_2$;

$X_5$ is O, S, C or N atom;

$X_6$ is C or N atom;

$X_7$ is O, S, C or N atom;

$R_1$ is H, CN, halogen, —(CH$_2$)$_{0-5}$—OR', —(CH$_2$)$_{0-5}$—NR'R", $C_{1-6}$ alkyl, $C_{1-6}$ haloalkyl, $C_{2-6}$ alkenyl, $C_{2-6}$ alkynyl, —(CH$_2$)$_{0-5}$—$C_{3-7}$ cycloalkyl, —(CH$_2$)$_{0-5}$—$C_{3-10}$ halocycloalkyl, —(CH$_2$)$_{0-5}$-4- to 8-membered heterocyclyl, —(CH$_2$)$_{0-5}$—$C_{6-10}$ aryl, —(CH$_2$)$_{0-5}$-5- to 14-membered heteroaryl, —C(O)R, —S(O)R or —S(O)$_2$R;

$R_2$ is H, CN, halogen, —(CH$_2$)$_{0-5}$—OR', —(CH$_2$)$_{0-5}$—NR'R", $C_{1-6}$ alkyl, $C_{1-6}$ haloalkyl, $C_{2-6}$ alkenyl, $C_{2-6}$ alkynyl, —(CH$_2$)$_{0-5}$—$C_{3-7}$ cycloalkyl, —(CH$_2$)$_{0-5}$—$C_{3-10}$ halocycloalkyl, —(CH$_2$)$_{0-5}$-4- to 8-membered heterocyclyl, —(CH$_2$)$_{0-5}$—$C_{6-10}$ aryl, —(CH$_2$)$_{0-5}$-5- to 14-membered heteroaryl, —C(O)R, —S(O)R or —S(O)$_2$R;

$R_{N2}$ is H, $C_{1-6}$ alkyl or $C_{1-6}$ haloalkyl;

the definition of $L_1'$ is the same as that of $L_1$;

the definition of $L_2'$ is the same as that of $L_2$;

the definition of E' is the same as that of E;

the definition of m' is the same as that of m;

$R_{s1}$ is selected from H, CN, halogen, —(CH$_2$)$_{0-5}$—OR', —(CH$_2$)$_{0-5}$—NR'R", $C_{1-6}$ alkyl, $C_{1-6}$ haloalkyl, —(CH$_2$)$_{0-5}$-4- to 8-membered heterocyclyl, $C_{2-6}$ alkenyl, $C_{2-6}$ alkynyl, —(CH$_2$)$_{0-5}$—$C_{3-7}$ cycloalkyl, —(CH$_2$)$_{0-5}$—$C_{3-10}$ halocycloalkyl, —(CH$_2$)$_{0-5}$—$C_{6-10}$ aryl, —(CH$_2$)$_{0-5}$-5- to 14-membered heteroaryl, —C(O)R, —S(O)R or —S(O)$_2$R;

$R_{s2}$ is selected from H, CN, halogen, $C_{1-6}$ alkyl, $C_{1-6}$ haloalkyl, $C_{2-6}$ alkenyl, $C_{2-6}$ alkynyl, —(CH$_2$)$_{0-5}$—OR', —(CH$_2$)$_{0-5}$—NR'R", —(CH$_2$)$_{0-5}$—$C_{3-7}$ cycloalkyl, —(CH$_2$)$_{0-5}$—$C_{3-10}$ halocycloalkyl, —(CH$_2$)$_{0-5}$-4- to 8-membered heterocyclyl, —(CH$_2$)$_{0-5}$—$C_{6-10}$ aryl, —(CH$_2$)$_{0-5}$-5- to 14-membered heteroaryl, —C(O)R, —S(O)R or —S(O)$_2$R;

$R_{s3}$ is selected from H, CN, halogen, —(CH$_2$)$_{0-5}$—OR', —(CH$_2$)$_{0-5}$—NR'R", $C_{1-6}$ alkyl, $C_{1-6}$ haloalkyl, —(CH$_2$)$_{0-5}$—$C_{3-7}$ cycloalkyl, —(CH$_2$)$_{0-5}$-4- to 8-membered heterocyclyl, $C_{2-6}$ alkenyl, $C_{2-6}$ alkynyl, —(CH$_2$)$_{0-5}$—$C_{3-10}$ halocycloalkyl, —(CH$_2$)$_{0-5}$—$C_{6-10}$ aryl, —(CH$_2$)$_{0-5}$-5- to 14-membered heteroaryl, —C(O)R, —S(O)R or —S(O)$_2$R;

$R_{s4}$ is selected from H, CN, halogen, $C_{1-6}$ alkyl, $C_{1-6}$ haloalkyl, $C_{2-6}$ alkenyl, $C_{2-6}$ alkynyl, —(CH$_2$)$_{0-5}$—OR', —(CH$_2$)$_{0-5}$—NR'R", —(CH$_2$)$_{0-5}$—$C_{3-7}$ cycloalkyl, —(CH$_2$)$_{0-5}$-4- to 8-membered heterocyclyl, (CH$_2$)$_{0-5}$—$C_{3-10}$ halocycloalkyl, —(CH$_2$)$_{0-5}$—$C_{6-10}$ aryl, —(CH$_2$)$_{0-5}$-5- to 14-membered heteroaryl, —C(O)R, —S(O)R or —S(O)$_2$R;

s1 is 0, 1, 2 or 3;

s2 is 0, 1, 2 or 3;

s3 is 0, 1 or 2;

s4 is 0, 1, 2, 3, 4 or 5;

the groups containing OH, NH, NH$_2$, CH, CH$_2$, or CH$_3$ in $L_1$, E, $L_2$, $L_1'$, E', $L_2'$, or the above alkyl, alkylene, haloalkyl, alkenyl, alkynyl, cycloalkyl, halocycloalkyl, heterocyclyl, aryl, and heteroaryl are each optionally substituted with 1, 2, 3 or more $R^s$ at each occurrence, wherein the $R^s$ is independently selected from the following groups at each occurrence: halogen, hydroxyl, amino, cyano, nitro, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ halocycloalkyl, 3- to 10-membered heterocyclyl, $C_{6-10}$ aryl, 5- to 14-membered heteroaryl, $C_{6-12}$ aralkyl, —$OR^{a'}$, —$OC(O)R^{a'}$, —$C(O)R^{a'}$, —$C(O)OR^{a'}$, —$C(O)NR^{a'}R^{b'}$, —$S(O)_n R^{a'}$, —$S(O)_n OR^{a'}$, —$S(O)_n NR^{a'}R^{b'}$, —$NR^{a'}R^{b'}$, —$NR^{a'}C(O)R^{b'}$, —$NR^{a'}$—$C(O)OR^{b'}$, —$NR^{a'}$—$S(O)$ n-$R^{b'}$, —$NR^{a'}C(O)NR^{a'}R^{b'}$, —$C_{1-6}$ alkylene-$R^{a'}$, —$C_{1-6}$ alkylene-$OR^{a'}$, —$C_{1-6}$ alkylene-$OC(O)R^{a'}$, —$C_{1-6}$ alkylene-$C(O)R^{a'}$, —$C_{1-6}$ alkylene-$S(O)_n R^{a'}$, —$C_{1-6}$ alkylene-$S(O)_n OR^{a'}$, —$C_{1-6}$ alkylene-$OC(O)NR^{a'}R^{b'}$, —$C_{1-6}$ alkylene-$C(O)NR^{a'}R^{b'}$, —$C_{1-6}$ alkylene-$NR^{a'}$—$C(O)NR^{a'}R^{b'}$, —$C_{1-6}$ alkylene-$OS(O)_n R^{a'}$, —$C_{1-6}$ alkylene-$S(O)_n NR^{a'}R^{b'}$, —$C_{1-6}$ alkylene-$NR^{a'}$—$S(O)_n NR^{a'}R^{b'}$, —$C_{1-6}$ alkylene-$NR^{a'}R^{b'}$ and —$O$—$C_{1-6}$ alkylene-$NR^{a'}R^{b'}$, and wherein the hydroxyl, amino, alkyl, alkylene, cycloalkyl, heterocyclyl, aryl, heteroaryl and aralkyl described with respect to the substituent $R^s$ are further optionally substituted with 1, 2, 3 or more substituents independently selected from: halogen, OH, amino, cyano, nitro, $C_{1-6}$ alkyl, $C_{1-6}$ haloalkyl, $C_{1-6}$ alkyl hydroxyl, $C_{3-6}$ cycloalkyl, 3- to 10-membered heterocyclyl, $C_{6-10}$ aryl, 5- to 14-membered heteroaryl and $C_{6-12}$ aralkyl;

n is independently 1 or 2 at each occurrence;

each of $R^{a'}$ and $R^{b'}$ is independently selected from H, $C_{1-6}$ alkyl, $C_{2-6}$ alkenyl, $C_{2-6}$ alkynyl, $C_{1-6}$ alkyl-O—, $C_{1-6}$ alkyl-S—, $C_{3-10}$ cycloalkyl, 3- to 10-membered heterocyclyl, $C_{6-10}$ aryl, 5- to 14-membered heteroaryl and $C_{6-12}$ aralkyl at each occurrence.

In a specific embodiment, ═══ represents single bond; in another specific embodiment, ═══ represents double bond.

$Z_1$

In a specific embodiment, $Z_1$ is O atom; in another specific embodiment, $Z_1$ is S atom; in another specific embodiment, $Z_1$ is N atom; in another specific embodiment, $Z_1$ is C atom; in another specific embodiment, $Z_1$ is substituted with one $R_{Z1}$; in another specific embodiment, $Z_1$ is substituted with two $R_{Z1}$; in another specific embodiment, $Z_1$ is absent.

$Z_2$

In a specific embodiment, $Z_2$ is O atom; in another specific embodiment, $Z_2$ is S atom; in another specific embodiment, $Z_2$ is N atom; in another specific embodiment, $Z_2$ is C atom; in another specific embodiment, $Z_2$ is substituted with one $R_{Z2}$; in another specific embodiment, $Z_2$ is substituted with two $R_{Z2}$.

$Z_3$

In a specific embodiment, $Z_3$ is O atom; in another specific embodiment, $Z_3$ is S atom; in another specific embodiment, $Z_3$ is N atom; in another specific embodiment, $Z_3$ is C atom; in another specific embodiment, $Z_3$ is substituted with one $R_{Z3}$; in another specific embodiment, $Z_3$ is substituted with two $R_{Z3}$.

In a specific embodiment, $Z_1$, $Z_2$ and $Z_3$ are all absent.

$Z_4$

In a specific embodiment, $Z_4$ is N; in another specific embodiment, $Z_4$ is $CR_{Z4}$.

$Z_5$

In a specific embodiment, $Z_5$ is N; in another specific embodiment, $Z_5$ is $CR_{Z5}$.

$R_a$, $R_b$ and $R_c$

In a specific embodiment, $R_a$ is H; in another specific embodiment, $R_a$ is halogen; in another specific embodiment, $R_a$ is OR'; in another specific embodiment, $R_a$ is NR'R"; in another specific embodiment, $R_a$ is $C_{1-6}$ alkyl; in another specific embodiment, $R_a$ is $C_{1-6}$ haloalkyl.

In a specific embodiment, $R_b$ is H; in another specific embodiment, $R_b$ is halogen; in another specific embodiment, $R_b$ is OR'; in another specific embodiment, $R_b$ is NR'R"; in another specific embodiment, $R_b$ is $C_{1-6}$ alkyl; in another specific embodiment, $R_b$ is $C_{1-6}$ haloalkyl.

In a specific embodiment, $R_c$ is H; in another specific embodiment, $R_c$ is halogen; in another specific embodiment, $R_c$ is OR'; in another specific embodiment, Re is NR'R"; in another specific embodiment, $R_c$ is $C_{1-6}$ alkyl; in another specific embodiment, $R_c$ is $C_{1-6}$ haloalkyl.

In a specific embodiment, $R_a$ and $R_b$ are taken together with the carbon atom to which they are attached to form C═O; in another specific embodiment, $R_a$ and $R_b$ are taken together with the carbon atom to which they are attached to form $C_{3-7}$ cycloalkyl; in another specific embodiment, $R_a$ and $R_b$ are taken together with the carbon atom to which they are attached to form 4- to 8-membered heterocyclyl; in another specific embodiment, $R_a$ and Re are taken together to form bond; in another specific embodiment, $R_a$ and $R_c$ are taken together with the carbon atoms to which they are attached to form $C_{3-7}$ cycloalkyl or 4- to 8-membered heterocyclyl.

$R_{Z1}$

In a specific embodiment, $R_{Z1}$ is absent; in another specific embodiment, $R_{Z1}$ is H; in another specific embodiment, $R_{Z1}$ is CN; in another specific embodiment, $R_{Z1}$ is halogen; in another specific embodiment, $R_{Z1}$ is —$(CH_2)_{0-5}$—OR'; in another specific embodiment, $R_{Z1}$ is —$(CH_2)_{0-5}$—NR'R"; in another specific embodiment, $R_{Z1}$ is $C_{1-6}$ alkyl; in another specific embodiment, $R_{Z1}$ is $C_{1-6}$ haloalkyl; in another specific embodiment, $R_{Z1}$ is —$(CH_2)_{0-5}$—$C_{3-7}$ cycloalkyl; in another specific embodiment, $R_{Z1}$ is —$(CH_2)_{0-5}$-4- to 8-membered heterocyclyl; in another specific embodiment, two $R_{Z1}$ are taken together with $Z_1$ to form C—O; in another specific embodiment, two $R_{Z1}$ are taken together with $Z_1$ to form $C_{3-7}$ cycloalkyl; in another specific embodiment, two $R_{Z1}$ are taken together with $Z_1$ to form 4- to 8-membered heterocyclyl.

$R_{Z2}$

In a specific embodiment, $R_{Z2}$ is absent; in another specific embodiment, $R_{Z2}$ is H; in another specific embodiment, $R_{Z2}$ is CN; in another specific embodiment, $R_{Z2}$ is halogen; in another specific embodiment, $R_{Z2}$ is —$(CH_2)_{0-5}$—OR'; in another specific embodiment, $R_{Z2}$ is —$(CH_2)_{0-5}$—NR'R"; in another specific embodiment, $R_{Z2}$ is $C_{1-6}$ alkyl; in another specific embodiment, $R_{Z2}$ is $C_{1-6}$ haloalkyl; in another specific embodiment, $R_{Z2}$ is —$(CH_2)_{0-5}$—$C_{3-7}$ cycloalkyl; in another specific embodiment, $R_{Z2}$ is —$(CH_2)_{0-5}$-4- to 8-membered heterocyclyl; in another specific embodiment, two $R_{Z2}$ are taken together with $Z_2$ to form C—O; in another specific embodiment, two $R_{Z2}$ are taken together with $Z_2$ to form $C_{3-7}$ cycloalkyl; in another specific embodiment, two $R_{Z2}$ are taken together with $Z_2$ to form 4- to 8-membered heterocyclyl.

$R_{Z3}$

In a specific embodiment, $R_{Z3}$ is absent; in another specific embodiment, $R_{Z3}$ is H; in another specific embodiment, $R_{Z3}$ is CN; in another specific embodiment, $R_{Z3}$ is halogen; in another specific embodiment, $R_{Z3}$ is —$(CH_2)_{0-5}$—OR'; in another specific embodiment, $R_{Z3}$ is —$(CH_2)_{0-5}$—NR'R"; in another specific embodiment, $R_{Z3}$ is $C_{1-6}$ alkyl; in another specific embodiment, $R_{Z3}$ is $C_{1-6}$ haloalkyl; in another specific embodiment, $R_{Z3}$ is —$(CH_2)_{0-5}$—$C_{3-7}$ cycloalkyl; in another specific embodiment, $R_{Z3}$ is —$(CH_2)_{0-5}$-4- to 8-membered heterocyclyl; in another specific embodiment, two $R_{Z3}$ are taken together with $Z_3$ to form C=O; in another specific embodiment, two $R_{Z3}$ are taken together with $Z_3$ to form $C_{3-7}$ cycloalkyl; in another specific embodiment, two $R_{Z3}$ are taken together with $Z_3$ to form 4- to 8-membered heterocyclyl.

$R_{Z4}$

In a specific embodiment, $R_{Z4}$ is H; in another specific embodiment, $R_{Z4}$ is CN; in another specific embodiment, $R_{Z4}$ is halogen; in another specific embodiment, $R_{Z4}$ is —(CH$_2$)$_{0-5}$—OR'; in another specific embodiment, $R_{Z4}$ is —(CH$_2$)$_{0-5}$—NR'R"; in another specific embodiment, $R_{Z4}$ is $C_{1-6}$ alkyl; in another specific embodiment, $R_{Z4}$ is $C_{1-6}$ haloalkyl.

$R_{Z5}$

In a specific embodiment, $R_{Z5}$ is H; in another specific embodiment, $R_{Z5}$ is CN; in another specific embodiment, $R_{Z5}$ is halogen; in another specific embodiment, $R_{Z5}$ is —(CH$_2$)$_{0-5}$—OR'; in another specific embodiment, $R_{Z5}$ is —(CH$_2$)$_{0-5}$—NR'R"; in another specific embodiment, $R_{Z5}$ is $C_{1-6}$ alkyl; in another specific embodiment, $R_{Z5}$ is $C_{1-6}$ haloalkyl; in another specific embodiment, $R_{Z5}$ is —(CH$_2$)$_{0-5}$—$C_{3-7}$ cycloalkyl; in another specific embodiment, $R_{Z5}$ is —(CH$_2$)$_{0-5}$-4- to 8-membered heterocyclyl.

In a specific embodiment, the ring in which $Z_4$ is located is absent.

$L_1$

In a specific embodiment, $L_1$ is bond; in another specific embodiment, $L_1$ is —O—; in another specific embodiment, $L_1$ is —S(O)$_p$—; in another specific embodiment, $L_1$ is —S(O)(=NR*)—; in another specific embodiment, $L_1$ is —NR$^\#$—; in another specific embodiment, $L_1$ is —CR$^\#$R$^{\#'}$—; in another specific embodiment, $L_1$ is —C$_a$R$^\#$R$^{\#'}$—C$_b$R$^\#$R$^{\#'}$—; in another specific embodiment, $L_1$ is —N=S(O)(R*)—; in another specific embodiment, $L_1$ is —S(O)(R*)=N—.

$L_2$

In a specific embodiment, $L_2$ is bond; in another specific embodiment, $L_2$ is —O—; in another specific embodiment, $L_2$ is —S(O)$_p$—; in another specific embodiment, $L_2$ is —S(O)(=NR*)—; in another specific embodiment, $L_2$ is —NR$^\#$—; in another specific embodiment, $L_2$ is —CR$^\#$R$^{\#'}$—; in another specific embodiment, $L_2$ is —C$_a$R$^\#$R$^{\#'}$—C$_b$R$^\#$R$^{\#'}$—; in another specific embodiment, $L_2$ is —N=S(O)(R*)—; in another specific embodiment, $L_2$ is —S(O)(R*)=N—.

In another specific embodiment, one of C$_a$R$^\#$R$^{\#'}$ and C$_b$R$^\#$R$^{\#'}$ in $L_1$ or $L_2$ can be replaced by O, S(O)$_p$, S(O)(=NR*) or NR$^\#$, and when one of C$_a$R$^\#$R$^{\#'}$ and C$_b$R$^\#$R$^{\#'}$ is replaced by O, S or NR$^\#$, the other of C$_a$R$^\#$R$^{\#'}$ and C$_b$R$^\#$R$^{\#'}$ can further be replaced by S(O)$_q$;

E

In a specific embodiment, E is bond; in another specific embodiment, E is —C$_c$R$^\#$R$^{\#'}$—C$_d$R$^\#$R$^{\#'}$—C$_e$R$^\#$R$^{\#'}$; in another specific embodiment, E is

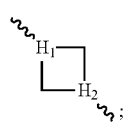

in another specific embodiment, E is

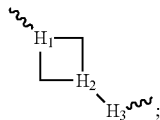

in another specific embodiment, E is

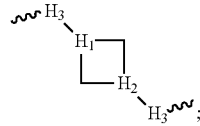

in another specific embodiment, E is

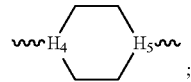

in another specific embodiment, E is

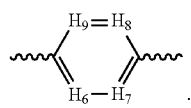

In another specific embodiment, one of C$_c$R$^\#$R$^{\#'}$, C$_d$R$^\#$R$^{\#'}$ or C$_e$R$^\#$R$^{\#'}$, or both of C$_c$R$^\#$R$^{\#'}$ and C$_e$R$^\#$R$^{\#'}$ can be replaced by O, S(O)$_p$, S(O)(=NR*) or NR$^\#$, and when one of C$_c$R$^\#$R$^{\#'}$, C$_d$R$^\#$R$^{\#'}$ or C$_e$R$^{190}$' is replaced by O, S or NR$^\#$, the other one or two of C$_c$R$^\#$R$^{\#'}$, C$_d$R$^\#$R$^{\#'}$ or C$_e$R$^\#$R$^{\#'}$ adjacent to it can further be replaced by S(O)$_q$;

In another specific embodiment, two E moieties can be taken together to form —CH$_2$CH$_2$OCH$_2$CH$_2$—; in another specific embodiment, two E moieties can be taken together to form —OCH$_2$CH$_2$CH$_2$CH$_2$—; in another specific embodiment, two E moieties can be taken together to form —CH$_2$CH$_2$CH$_2$CH$_2$O—; in another specific embodiment, two E moieties can be taken together to form

in another specific embodiment, two E moieties can be taken together to form

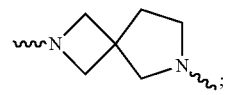

in another specific embodiment, two E moieties can be taken together to form

;

in another specific embodiment, two E moieties can be taken together to form

;

in another specific embodiment, two E moieties can be taken together to form

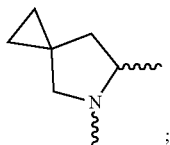

;

in another specific embodiment, two E moieties can be taken together to form

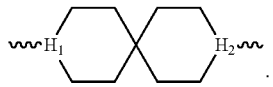

.

In another specific embodiment, in the embodiment of $L_1$, $L_2$ or E, $R^{\#}$ and $R^{\#}$ on adjacent atoms can be taken together to form bond, and $R^{\#'}$ and $R^{\#'}$ on adjacent atoms can be taken together to form bond;

In another specific embodiment, in the embodiment of $L_1$, $L_2$ or E, $R^{\#}$ and $R^{\#'}$ on the same atom can be taken together to form =O, or $C_{3-7}$ cycloalkyl, 4- to 8-membered heterocyclyl, $C_{6-10}$ aryl or 5- to 6-membered heteroaryl, each of which is optionally substituted with Rx group; in another specific embodiment, in the embodiment of $L_1$, $L_2$ or E, $R^{\#}$ and $R^{\#'}$ on different atoms can be taken together to form $C_{3-7}$ cycloalkyl, 4- to 8-membered heterocyclyl, $C_{6-10}$ aryl or 5- to 6-membered heteroaryl, each of which is optionally substituted with Rx group.

m

In a specific embodiment, m is 0; in another specific embodiment, m is 1; in another specific embodiment, m is 2; in another specific embodiment, m is 3; in another specific embodiment, m is 4; in another specific embodiment, m is 5; in another specific embodiment, m is 6; in another specific embodiment, m is 7; in another specific embodiment, m is 8; in another specific embodiment, m is 9; in another specific embodiment, m is 10.

$X_1$

In a specific embodiment, $X_1$ is C atom; in another specific embodiment, $X_1$ is N atom.

$X_2$

In a specific embodiment, $X_2$ is C atom; in another specific embodiment, $X_2$ is N atom.

$X_3$

In a specific embodiment, $X_3$ is C atom; in another specific embodiment, $X_3$ is N atom.

$X_4$

In a specific embodiment, $X_4$ is O atom; in another specific embodiment, $X_4$ is S atom; in another specific embodiment, $X_4$ is C atom; in another specific embodiment, $X_4$ is N atom; in another specific embodiment, $X_4$ is substituted with one $R_2$; in another specific embodiment, $X_4$ is substituted with two $R_2$.

$X_5$

In a specific embodiment, $X_5$ is O atom; in another specific embodiment, $X_5$ is S atom; in another specific embodiment, $X_5$ is C atom; in another specific embodiment, $X_5$ is N atom.

$X_6$

In a specific embodiment, $X_6$ is C atom; in another specific embodiment, $X_6$ is N atom.

$X_7$

In a specific embodiment, $X_7$ is O atom; in another specific embodiment, $X_7$ is S atom; in another specific embodiment, $X_7$ is C atom; in another specific embodiment, $X_7$ is N atom.

In a specific embodiment, the ring where $X_4$, $X_5$, $X_6$ and $X_7$ are located is pyrazole ring; in another specific embodiment, the ring where $X_4$, $X_5$, $X_6$ and $X_7$ are located is imidazole ring; in another specific embodiment, the ring where $X_4$, $X_5$, $X_6$ and $X_7$ are located is thiazole ring; in another specific embodiment, the ring where $X_4$, $X_5$, $X_6$ and $X_7$ are located is oxazole ring; in another specific embodiment, the ring where $X_4$, $X_5$, $X_6$ and $X_7$ are located is triazole ring; in another specific embodiment, the ring where $X_4$, $X_5$, $X_6$ and $X_7$ are located is tetrazole ring; in another specific embodiment, the ring where $X_4$, $X_5$, $X_6$ and $X_7$ are located is

;

in another specific embodiment, the ring where $X_4$, $X_5$, $X_6$ and $X_7$ are located is

;

in another specific embodiment, the ring where $X_4$, $X_5$, $X_6$ and $X_7$ are located is

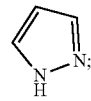

;

in another specific embodiment, the ring where $X_4$, $X_5$, $X_6$ and $X_7$ are located is

;

in another specific embodiment, the ring where $X_4$, $X_5$, $X_6$ and $X_7$ are located is

in another specific embodiment, the ring where $X_4$, $X_5$, $X_6$ and $X_7$ are located is

in another specific embodiment, the ring where $X_4$, $X_5$, $X_6$ and $X_7$ are located is

in another specific embodiment, the ring where $X_4$, $X_5$, $X_6$ and $X_7$ are located is

in another specific embodiment, the ring where $X_4$, $X_5$, $X_6$ and $X_7$ are located is

in another specific embodiment, the ring where $X_4$, $X_5$, $X_6$ and $X_7$ are located is

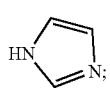

in another specific embodiment, the ring where $X_4$, $X_5$, $X_6$ and $X_7$ are located is

in another specific embodiment, the ring where $X_4$, $X_5$, $X_6$ and $X_7$ are located is

in another specific embodiment, the ring where $X_4$, $X_5$, $X_6$ and $X_7$ are located is

in another specific embodiment, the ring where $X_4$, $X_5$, $X_6$ and $X_7$ are located is

in another specific embodiment, the ring where $X_4$, $X_5$, $X_6$ and $X_7$ are located is

Any technical solution in any one of the above specific embodiments, or any combination thereof, may be combined with any technical solution in other specific embodiments or any combination thereof. The present disclosure is intended to include all combinations of such technical solutions, which are not exhaustively listed here to save space.

In a more specific embodiment, the present disclosure provides a compound of general formula (I), or a pharmaceutically acceptable salt, enantiomer, diastereomer, racemate, solvate, hydrate, polymorph, prodrug, or isotopic variant thereof, or a mixture thereof:

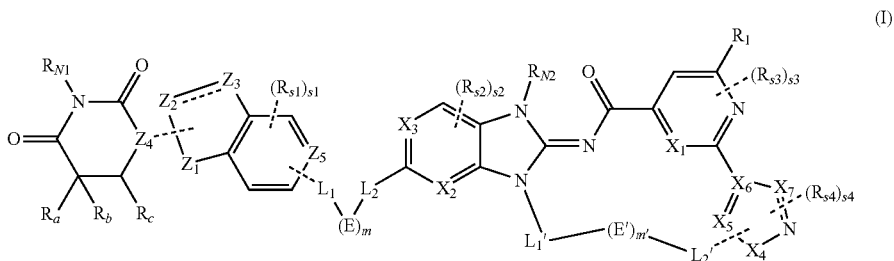

(I)

wherein

═ represents single bond or double bond;

----- represents that the point of attachment to the rest of the molecule can be located at an available point of a ring;

$Z_1$ is O, S, N or C atom, which is optionally substituted with one or two $R_{Z1}$;

$Z_2$ is O, S, N or C atom, which is optionally substituted with one or two $R_{Z2}$;

$Z_3$ is O, S, N or C atom, which is optionally substituted with one or two $R_{Z3}$; with the proviso that when ═ represents double bond, $Z_2$ is N or C atom, and $Z_3$ is N or C atom;

$Z_4$ is N or $CR_{Z4}$;

$Z_5$ is N or $CR_{Z5}$;

$R_a$, $R_b$ and $R_c$ are independently H, halogen, $C_{1-6}$ alkyl or $C_{1-6}$ haloalkyl;

$R_{N1}$ is H, $C_{1-6}$ alkyl or $C_{1-6}$ haloalkyl;

$R_{Z1}$ is absent, H, CN, halogen, $C_{1-6}$ alkyl, or $C_{1-6}$ haloalkyl; or two $R_{Z1}$ are taken together with $Z_1$ to form C═O;

$R_{Z2}$ is absent, H, CN, halogen, $C_{1-6}$ alkyl, or $C_{1-6}$ haloalkyl;

$R_{Z3}$ is absent, H, CN, halogen, $C_{1-6}$ alkyl, or $C_{1-6}$ haloalkyl; or two $R_{Z3}$ are taken together with $Z_3$ to form C═O;

$R_{Z4}$ is H, CN, halogen, $C_{1-6}$ alkyl, or $C_{1-6}$ haloalkyl;

$R_{Z5}$ is H, CN, halogen, $C_{1-6}$ alkyl, or $C_{1-6}$ haloalkyl;

$L_1$ is selected from bond, —O—, —S(O)$_p$—, —NR$^\#$—, —CR$^\#$R$^{\#'}$— or —C$_a$R$^\#$R$^{\#'}$—C$_b$R$^\#$R$^{\#'}$—;

$L_2$ is selected from bond, —O—, —S(O)$_p$—, —NR$^\#$—, —CR$^\#$R$^{\#'}$— or —C$_a$R$^\#$R$^{\#'}$—C$_b$R$^\#$R$^{\#'}$—;

wherein one of C$_a$R$^\#$R$^{\#'}$ or C$_b$R$^\#$R$^{\#'}$ can be replaced by O, S(O)$_p$ or NR$^\#$, and when one of C$_a$R$^\#$R$^{\#'}$ or C$_b$R$^\#$R$^{\#'}$ is replaced by O, S or NR$^\#$, the other of C$_a$R$^\#$R$^{\#'}$ or C$_b$R$^\#$R$^{\#'}$ can further be replaced by S(O)$_q$;

E is independently selected from: —C$_c$R$^\#$R$^{\#'}$—C$_d$R$^\#$R$^{\#'}$—C$_e$R$^\#$R$^{\#'}$ or

[structure: ring fragment with H$_4$ and H$_5$]

wherein any one of C$_c$R$^\#$R$^{\#'}$, C$_d$R$^\#$R$^{\#'}$ or C$_e$R$^\#$R$^{\#'}$, or both of C$_c$R$^\#$R$^{\#'}$ and C$_e$R$^\#$R$^{\#'}$ can be replaced by O, S(O)$_p$ or NR$^\#$, and when any one of C$_c$R$^\#$R$^{190}$, C$_d$R$^\#$R$^\#$ or C$_e$R$^\#$R$^{\#'}$ is replaced by O, S or NR$^\#$, the other one or two of C$_c$R$^\#$R$^{\#'}$, C$_d$R$^\#$R$^{\#'}$ or C$_e$R$^\#$R$^{\#'}$ adjacent to it can further be replaced by S(O)$_q$;

$H_4$ and $H_5$ are N or C atom;

p is 0, 1 or 2;

q is 1 or 2;

R$^\#$ is H, halogen, $C_{1-6}$ alkyl, $C_{1-6}$ haloalkyl, $C_{2-6}$ alkenyl or $C_{2-6}$ alkynyl;

R$^{\#'}$ is H, halogen, $C_{1-6}$ alkyl, $C_{1-6}$ haloalkyl, $C_{2-6}$ alkenyl or $C_{2-6}$ alkynyl;

or, R$^\#$ and R$^\#$ on adjacent atoms can be taken together to form bond, and R$^{\#'}$ and R$^{\#'}$ on adjacent atoms can be taken together to form bond;

or, R$^\#$ and R$^{\#'}$ on the same or different atoms can be taken together to form ═O;

m is 0, 1, 2, 3, 4, 5, 6, 7, 8, 9 or 10;

$X_1$ is C or N atom;

$X_2$ is C or N atom;

$X_3$ is C or N atom;

$X_4$ is O, S, C or N atom, which is optionally substituted with one or two $R_2$;

$X_5$ is O, S, C or N atom;

$X_6$ is C or N atom;

$X_7$ is O, S, C or N atom;

$R_1$ is H, CN, halogen, $C_{1-6}$ alkyl, $C_{1-6}$ haloalkyl, $C_{2-6}$ alkenyl or $C_{2-6}$ alkynyl;

$R_2$ is H, CN, halogen, $C_{1-6}$ alkyl, $C_{1-6}$ haloalkyl, $C_{2-6}$ alkenyl or $C_{2-6}$ alkynyl;

$R_{N2}$ is H, $C_{1-6}$ alkyl or $C_{1-6}$ haloalkyl;

the definition of $L_1'$ is the same as that of $L_1$;

the definition of $L_2'$ is the same as that of $L_2$;

the definition of $E'$ is the same as that of $E$;

the definition of $m'$ is the same as that of $m$;

$R_{s1}$ is selected from H, CN, halogen, $C_{1-6}$ alkyl or $C_{1-6}$ haloalkyl;

$R_{s2}$ is selected from H, CN, halogen, $C_{1-6}$ alkyl, $C_{1-6}$ haloalkyl, $C_{2-6}$ alkenyl or $C_{2-6}$ alkynyl;

$R_{s3}$ is selected from H, CN, halogen, $C_{1-6}$ alkyl or $C_{1-6}$ haloalkyl;

$R_{s4}$ is selected from H, CN, halogen, $C_{1-6}$ alkyl, $C_{1-6}$ haloalkyl, $C_{2-6}$ alkenyl or $C_{2-6}$ alkynyl;

s1 is 0, 1, 2 or 3;

s2 is 0, 1, 2 or 3;

s3 is 0, 1 or 2;

s4 is 0, 1, 2, 3, 4 or 5.

In a more specific embodiment, the present disclosure provides a compound of general formula (II), or a pharmaceutically acceptable salt, enantiomer, diastereomer, racemate, solvate, hydrate, polymorph, prodrug, or isotopic variant thereof, or a mixture thereof, wherein (II)

[chemical structure of formula (II)]

wherein all the groups are as defined in above;
alternatively,
═ represents single bond or double bond;
----- represents that the point of attachment to the rest of the molecule can be located at an available point of a ring;
$Z_1$ is N or C atom, which is optionally substituted with one or two $R_{Z1}$; or $Z_1$ is absent, and thus $Z_2$ and C atom on the aromatic ring that are connected to $Z_1$ are connected to R to form a compound of general formula (II'):

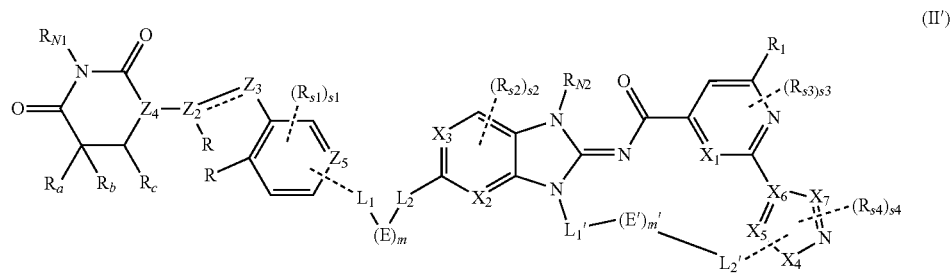

(II')

$Z_2$ is N or C atom, which is optionally substituted with $R_{Z2}$;

$Z_3$ is N or C atom, which is optionally substituted with one or two $R_{Z3}$;

$Z_4$ is N or $CR_{Z4}$;

$Z_5$ is N or $CR_{Z5}$;

$R_{Z1}$ is absent, H, CN, halogen, —(CH$_2$)$_{0-5}$—OR', —(CH$_2$)$_{0-5}$—NR'R", $C_{1-6}$ alkyl, $C_{1-6}$ haloalkyl, —(CH$_2$)$_{0-5}$—C$_{3-7}$ cycloalkyl or —(CH$_2$)$_{0-5}$-4- to 8-membered heterocyclyl; or two $R_{Z1}$ are taken together with $Z_1$ to form C═O, $C_{3-7}$ cycloalkyl or 4- to 8-membered heterocyclyl;

$R_{Z2}$ is absent, H, CN, halogen, —(CH$_2$)$_{0-5}$—OR', —(CH$_2$)$_{0-5}$—NR'R", $C_{1-6}$ alkyl, $C_{1-6}$ haloalkyl, —(CH$_2$)$_{0-5}$—C$_{3-7}$ cycloalkyl or —(CH$_2$)$_{0-5}$-4- to 8-membered heterocyclyl;

$R_{Z3}$ is absent, H, CN, halogen, —(CH$_2$)$_{0-5}$—OR', —(CH$_2$)$_{0-5}$—NR'R", $C_{1-6}$ alkyl, $C_{1-6}$ haloalkyl, —(CH$_2$)$_{0-5}$—C$_{3-7}$ cycloalkyl or —(CH$_2$)$_{0-5}$-4- to 8-membered heterocyclyl; or two $R_{Z3}$ are taken together with $Z_3$ to form C═O, $C_{3-7}$ cycloalkyl or 4- to 8-membered heterocyclyl;

$R_{Z4}$ is H, CN, halogen, —(CH$_2$)$_{0-5}$—OR', —(CH$_2$)$_{0-5}$—NR'R", $C_{1-6}$ alkyl or $C_{1-6}$ haloalkyl;

$R_{Z5}$ is H, CN, halogen, —(CH$_2$)$_{0-5}$—OR', —(CH$_2$)$_{0-5}$—NR'R", $C_{1-6}$ alkyl, $C_{1-6}$ haloalkyl, —(CH$_2$)$_{0-5}$—C$_{3-7}$ cycloalkyl or —(CH$_2$)$_{0-5}$-4- to 8-membered heterocyclyl;

and other groups are as defined in above.

In a more specific embodiment, the present disclosure provides a compound of general formula (III), or a pharmaceutically acceptable salt, enantiomer, diastereomer, racemate, solvate, hydrate, polymorph, prodrug, or isotopic variant thereof, or a mixture thereof, wherein

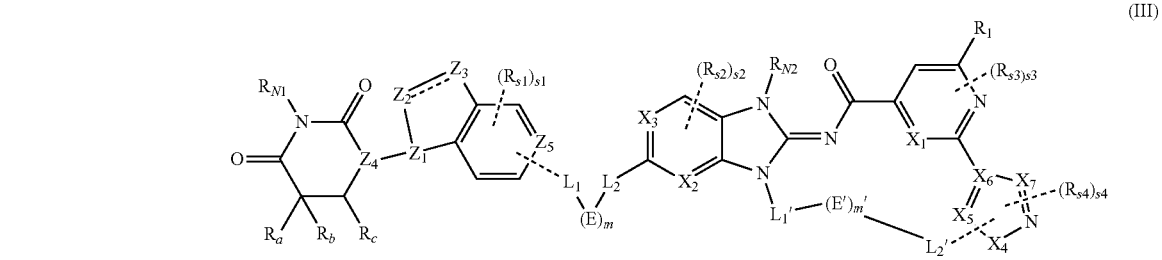

(III)

wherein all the groups are as defined in above; alternatively,

═ represents single bond or double bond;

----- represents that the point of attachment to the rest of the molecule can be located at an available point of a ring;

$Z_1$ is N or C atom, which is optionally substituted with $R_{Z1}$;

$Z_2$ is N or C atom, which is optionally substituted with one or two $R_{Z2}$;

$Z_3$ is N or C atom, which is optionally substituted with one or two $R_{Z3}$;

$Z_4$ is N or $CR_{Z4}$;

$Z_5$ is N or $CR_{Z5}$;

$R_{Z1}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl;

$R_{Z2}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z2}$ are taken together with $Z_2$ to form C=O, $C_{3-7}$ cycloalkyl or 4- to 8-membered heterocyclyl;

$R_{Z3}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z3}$ are taken together with $Z_3$ to form C—O, $C_{3-7}$ cycloalkyl or 4- to 8-membered heterocyclyl;

$R_{Z4}$ is H, CN, halogen, —$(CH_2)_{0-5}$—OR', —$(CH_2)_{0-5}$—NR'R", $C_{1-6}$ alkyl or $C_{1-6}$ haloalkyl;

$R_{Z5}$ is H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl;

and other groups are as defined in above.

In a more specific embodiment, the present disclosure provides a compound of general formula (IV) or (IV'), or a pharmaceutically acceptable salt, enantiomer, diastereomer, racemate, solvate, hydrate, polymorph, prodrug, or isotopic variant thereof, or a mixture thereof, wherein wherein all the groups are as defined in above; alternatively, ═ represents single bond or double bond;

----- represents that the point of attachment to the rest of the molecule can be located at an available point of a ring;

$Z_2$ is N or C atom, which is optionally substituted with one or two $R_{Z2}$;

$Z_3$ is O, S, N or C atom, which is optionally substituted with one or two $R_{Z3}$; with the proviso that when ═ represents double bond, $Z_3$ is N or C atom;

$Z_4$ is N or $CR_{Z4}$;

$Z_5$ is N or $CR_{Z5}$;

$R_{Z2}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z2}$ are taken together with $Z_2$ to form C=O, $C_{3-7}$ cycloalkyl or 4- to 8-membered heterocyclyl;

$R_{Z3}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z3}$ are taken together with $Z_3$ to form C—O, $C_{3-7}$ cycloalkyl or 4- to 8-membered heterocyclyl;

$R_{Z4}$ is H, CN, halogen, —$(CH_2)_{0-5}$—OR', —$(CH_2)_{0-5}$—NR'R", $C_{1-6}$ alkyl or $C_{1-6}$ haloalkyl;

$R_{Z5}$ is H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl;

R is H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl;

and other groups are as defined in above.

In a more specific embodiment, the present disclosure provides a compound of general formula (V), or a pharmaceutically acceptable salt, enantiomer, diastereomer, racemate, solvate, hydrate, polymorph, prodrug, or isotopic variant thereof, or a mixture thereof, wherein

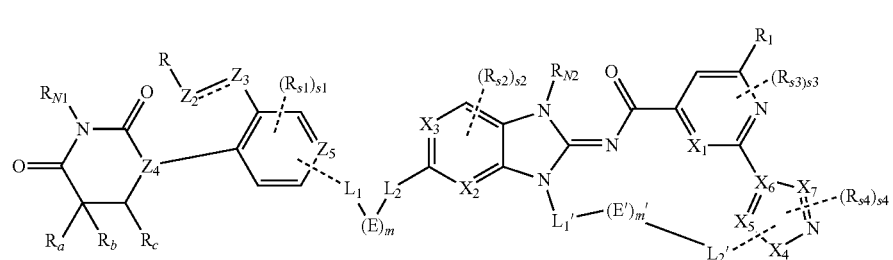

(IV)

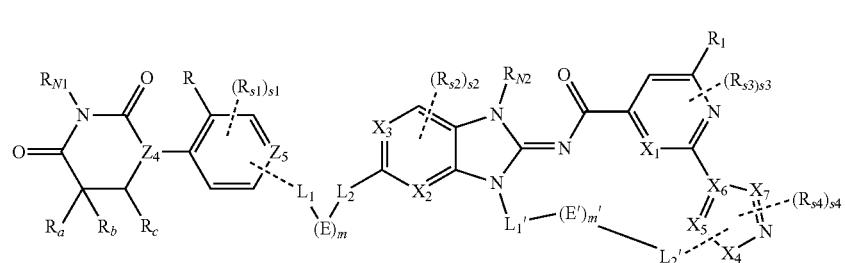

(IV')

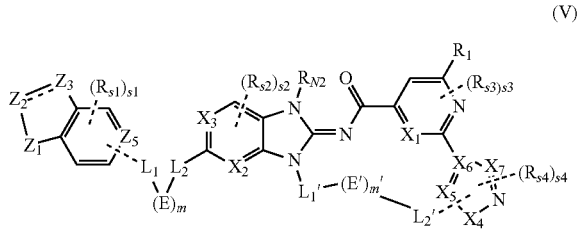

(V)

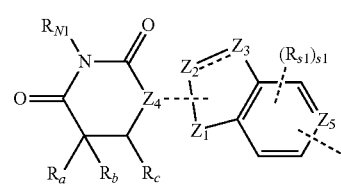
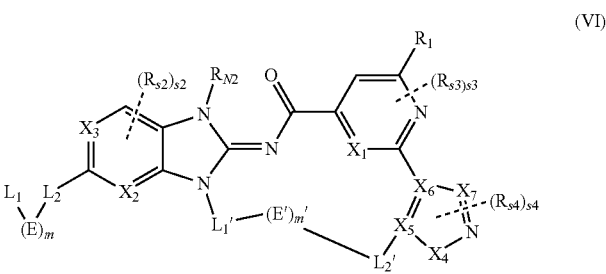

(VI)

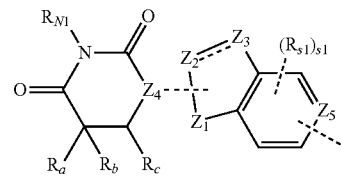
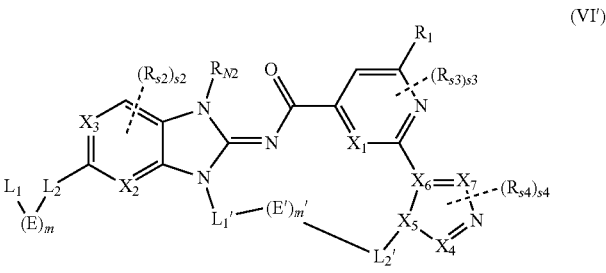

(VI')

wherein all the groups are as defined in above; alternatively,

═ represents single bond or double bond;

----- represents that the point of attachment to the rest of the molecule can be located at an available point of a ring;

$Z_1$ is O, S, N or C atom, which is optionally substituted with one or two $R_{Z1}$;

$Z_2$ is O, S, N or C atom, which is optionally substituted with one or two $R_{Z2}$;

$Z_3$ is O, S, N or C atom, which is optionally substituted with one or two $R_{Z3}$; with the proviso that when ═ represents double bond, $Z_2$ is N or C atom, and $Z_3$ is N or C atom; $Z_5$ is N or $CR_{Z5}$;

$R_{Z1}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z1}$ are taken together with $Z_1$ to form C═O, $C_{3-7}$ cycloalkyl or 4- to 8-membered heterocyclyl;

$R_{Z2}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z2}$ are taken together with $Z_2$ to form C═O, $C_{3-7}$ cycloalkyl or 4- to 8-membered heterocyclyl;

$R_{Z3}$ is absent, H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl; or two $R_{Z3}$ are taken together with $Z_3$ to form C═O, $C_{3-7}$ cycloalkyl or 4- to 8-membered heterocyclyl;

$R_{Z5}$ is H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl or —$(CH_2)_{0-5}$-4- to 8-membered heterocyclyl;

and other groups are as defined in above.

In a more specific embodiment, the present disclosure provides a compound of general formula (VI) or (VI'), or a pharmaceutically acceptable salt, enantiomer, diastereomer, racemate, solvate, hydrate, polymorph, prodrug, or isotopic variant thereof, or a mixture thereof, wherein wherein all the groups are as defined in above; alternatively, in general formula (VI) or (VI'), $X_1$ is C or N atom;

$X_2$ is C or N atom;

$X_3$ is C or N atom;

$X_4$ is O, S, C or N atom; when $X_4$ is C or N atom, $X_4$ is optionally substituted with one or two $R_2$;

$X_5$ is C or N atom;

$X_6$ is C or N atom;

$X_7$ is O, S, C or N atom;

$R_1$ is H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl, —$(CH_2)_{0-5}$-4- to 8-membered heterocyclyl, —$(CH_2)_{0-5}$—$C_{6-10}$ aryl, —$(CH_2)_{0-5}$-5- to 14-membered heteroaryl, —C(O)R, —S(O)R or —S(O)$_2$R;

$R_2$ is H, CN, halogen, —$(CH_2)_{0-5}$—OR', —$(CH_2)_{0-5}$—NR'R", $C_{1-6}$ alkyl, $C_{1-6}$ haloalkyl, —$(CH_2)_{0-5}$—$C_{3-7}$ cycloalkyl, —$(CH_2)_{0-5}$-4- to 8-membered heterocyclyl, $C_{2-6}$ alkenyl, $C_{2-6}$ alkynyl, —$(CH_2)_{0-5}$—$C_{3-10}$ halocycloalkyl, —$(CH_2)_{0-5}$—$C_{6-10}$ aryl, —$(CH_2)_{0-5}$-5- to 14-membered heteroaryl, —C(O)R, —S(O)R or —S(O)$_2$R;

and other groups are as defined in above.

In a more specific embodiment, the present disclosure provides a compound of general formula (VII) or (VII'), or a pharmaceutically acceptable salt, enantiomer, diastereomer, racemate, solvate, hydrate, polymorph, prodrug, or isotopic variant thereof, or a mixture thereof, wherein

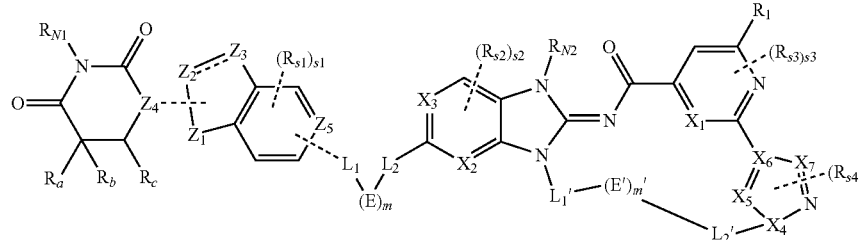

(VII)

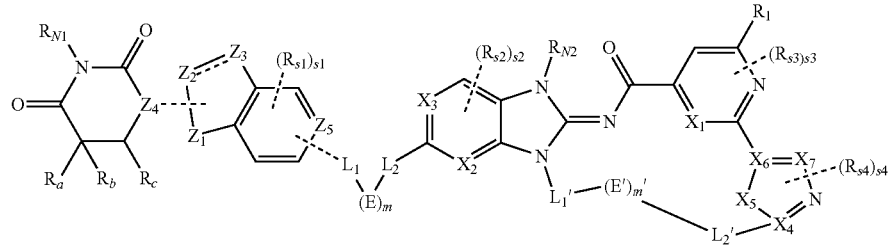

(VII')

wherein all the groups are as defined in above; alternatively, in general formula (VII) or (VII'), $X_1$ is C or N atom;

$X_2$ is C or N atom;

$X_3$ is C or N atom;

$X_4$ is C or N atom; when $X_4$ is C atom, $X_4$ is optionally substituted with $R_2$;

$X_5$ is O, S, C or N atom;

$X_6$ is C or N atom;

$X_7$ is O, S, C or N atom;

$R_1$ is H, —(CH$_2$)$_{0-5}$—OR', —(CH$_2$)$_{0-5}$—NR'R", halogen, cyano, C$_{1-6}$ alkyl, C$_{1-6}$ haloalkyl, —(CH$_2$)$_{0-5}$—C$_{3-7}$ cycloalkyl, —(CH$_2$)$_{0-5}$-4- to 8-membered heterocyclyl, —(CH$_2$)$_{0-5}$—C$_{6-10}$ aryl, —(CH$_2$)$_{0-5}$-5- to 14-membered heteroaryl, —C(O)R, —S(O)R or —S(O)$_2$R;

$R_2$ is H, CN, halogen, —(CH$_2$)$_{0-5}$—OR', —(CH$_2$)$_{0-5}$—NR'R", C$_{1-6}$ alkyl, C$_{1-6}$ haloalkyl, —(CH$_2$)$_{0-5}$—C$_{3-7}$ cycloalkyl, —(CH$_2$)$_{0-5}$-4- to 8-membered heterocyclyl, —(CH$_2$)$_{0-5}$—C$_{6-10}$ aryl, —(CH$_2$)$_{0-5}$-5- to 14-membered heteroaryl, —C(O)R, —S(O)R or —S(O)$_2$R;

and other groups are as defined in above.

In a more specific embodiment, the present disclosure provides a compound, or a pharmaceutically acceptable salt, enantiomer, diastereomer, racemate, solvate, hydrate, polymorph, prodrug, or isotopic variant thereof, or a mixture thereof as mentioned above, wherein

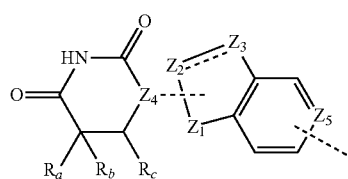

is selected from the following groups:

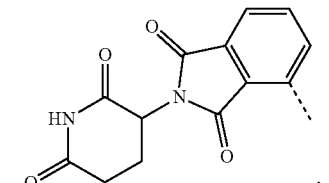

,

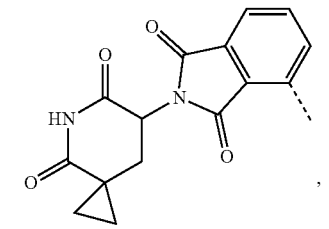

,

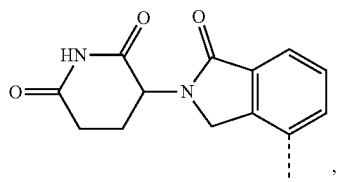

,

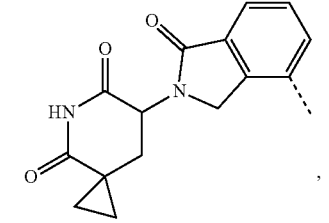

,

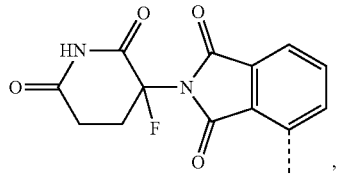

,

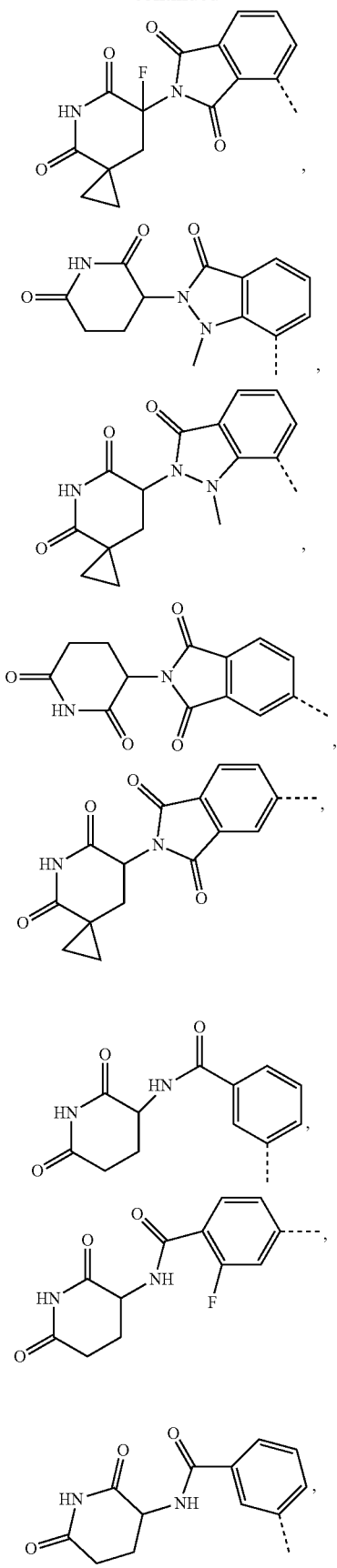
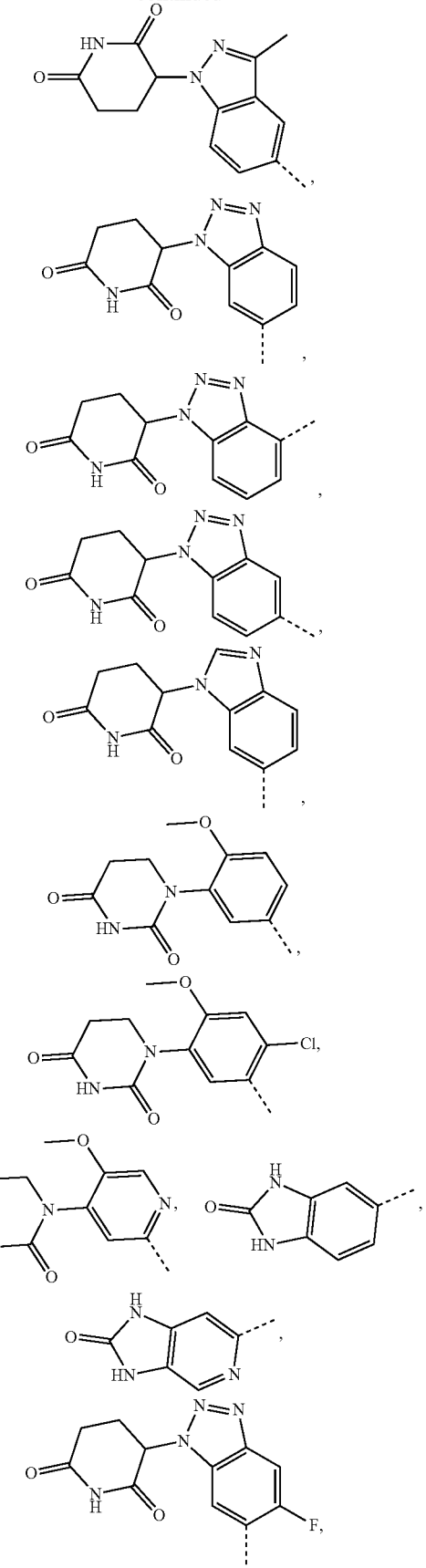

-continued
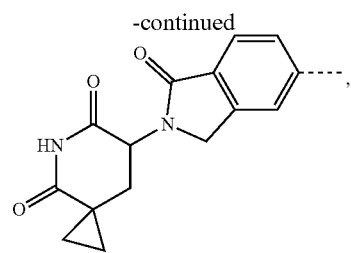
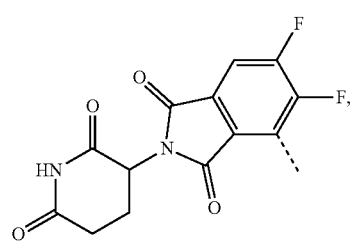
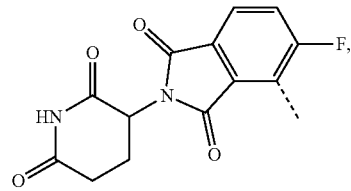
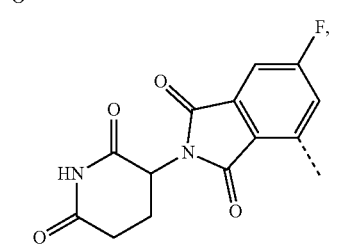
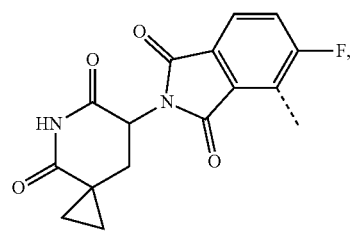
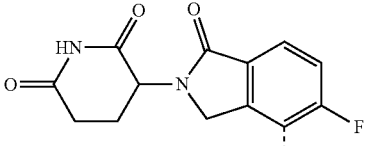
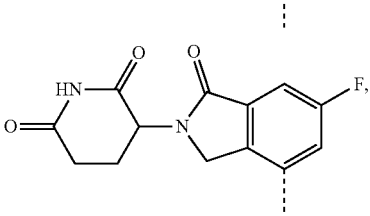
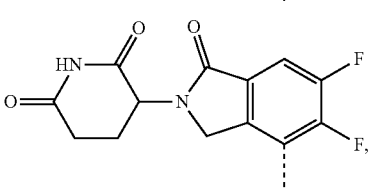
-continued
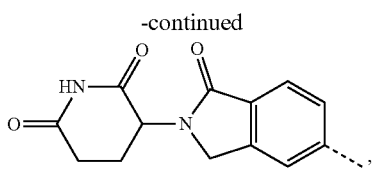
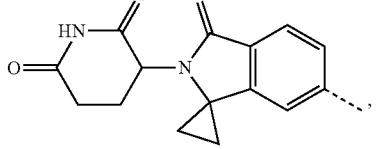
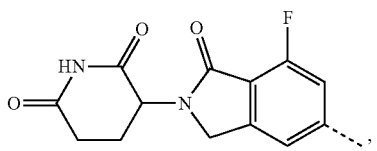
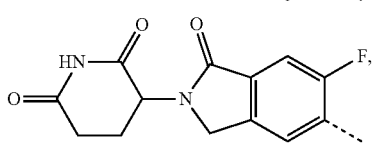
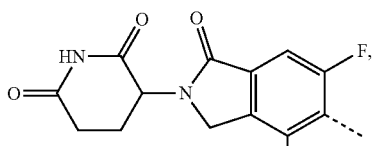
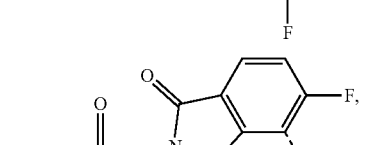
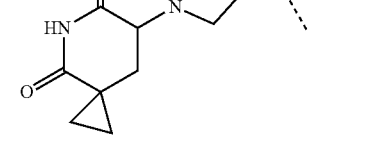
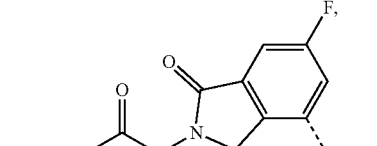
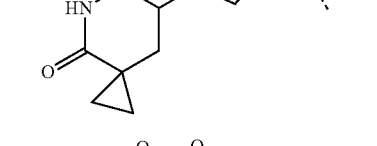
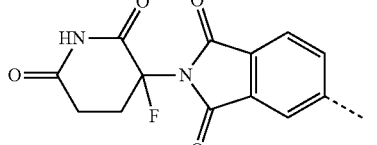
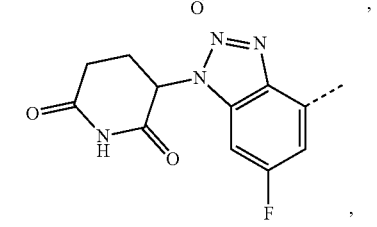

-continued
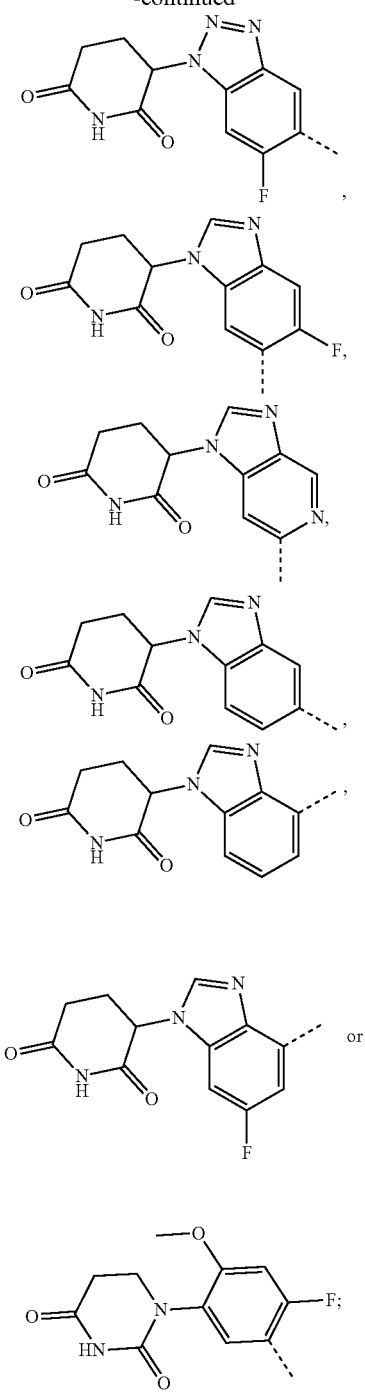
alternatively, wherein
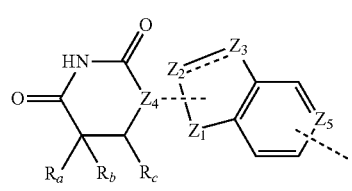
is selected from the following groups:
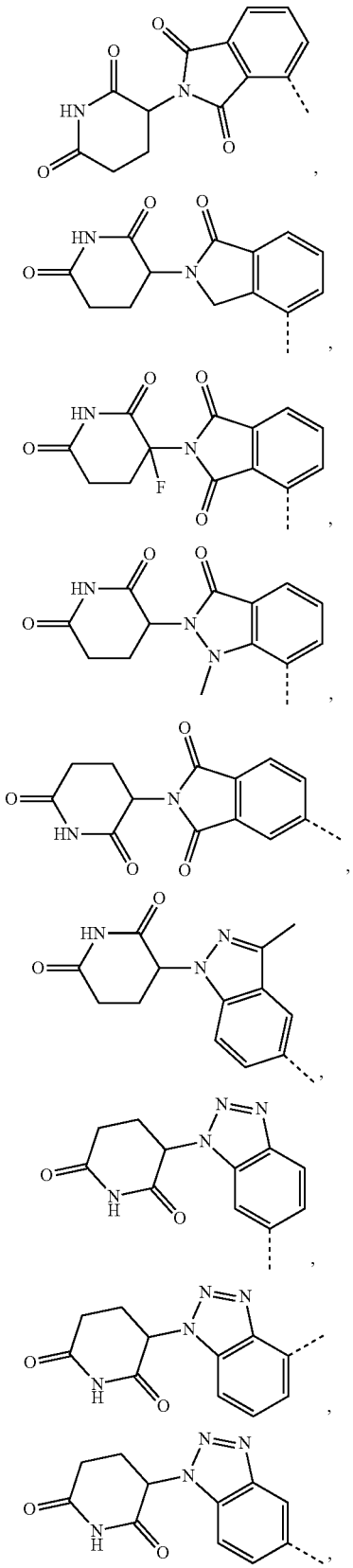

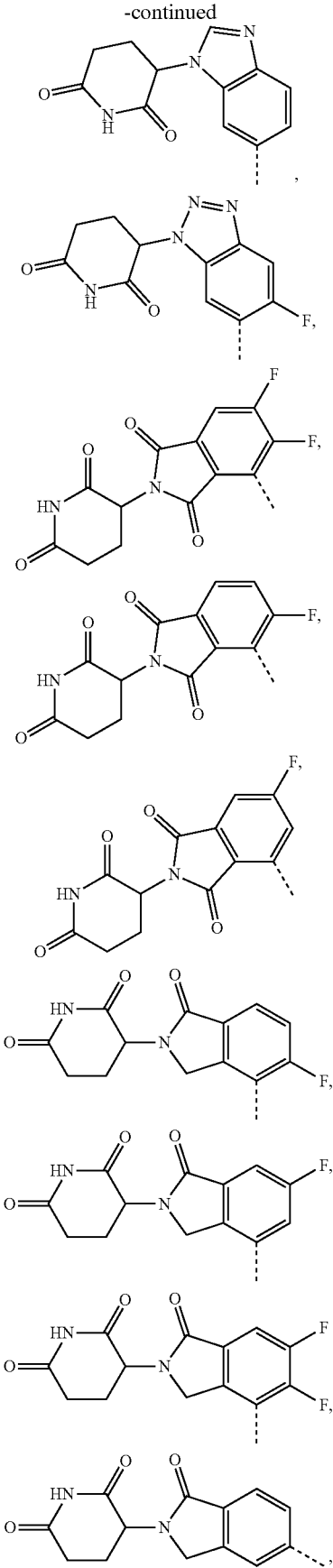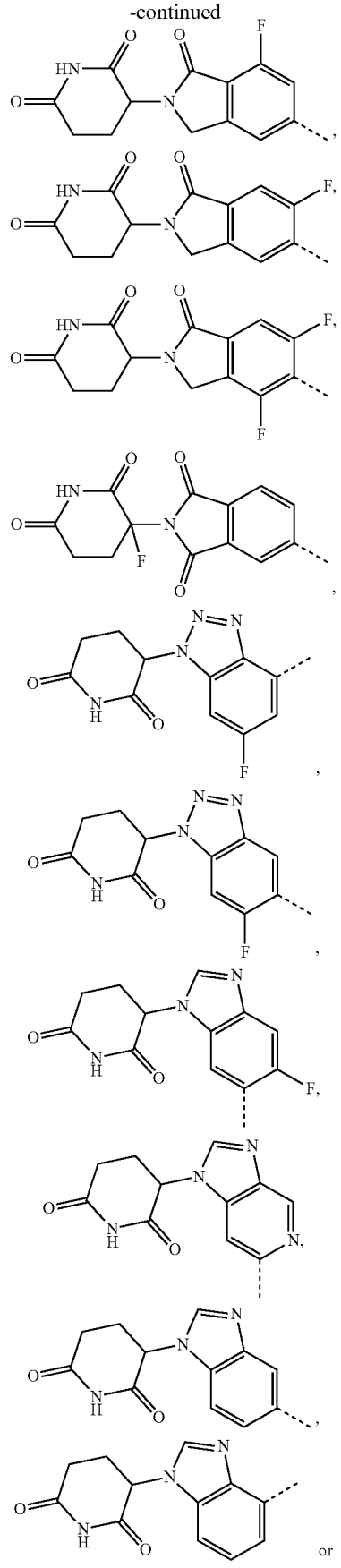

-continued

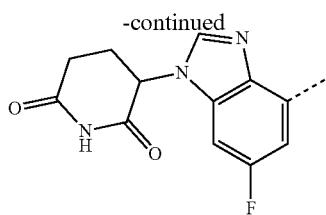

In a more specific embodiment, the present disclosure provides a compound, or a pharmaceutically acceptable salt, enantiomer, diastereomer, racemate, solvate, hydrate, polymorph, prodrug, or isotopic variant thereof, or a mixture thereof as mentioned above, wherein $L_1$, $L_2$, $L_1'$ and $L_2'$ are independently selected from bond, —O—, —S—, —S(O)—, —S(O)$_2$—, —S(O)(=NH)—, —S(O)(=NMe)-,

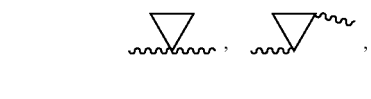

—NH—, —N(Me)-,

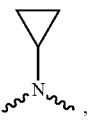

—N(CF$_3$)—, —CH$_2$—, —CH(OMe)-, —CH(Cl)—, —CH(F)—, —CF$_2$—, —CH(CF$_3$)—, —C(O)—, —CH$_2$CH$_2$—, —CH=CH—, —C≡C—, —OCH$_2$—, —CH$_2$O—, —SCH$_2$—, —CH$_2$S—, —S(O)CH$_2$—, —CH$_2$S(O)—, —S(O)$_2$CH$_2$—, —CH$_2$S(O)$_2$—, —NHCH$_2$—, —N(Me)CH$_2$—, —CH$_2$NH—, —CH$_2$N(Me)-, —C(O)CH$_2$—, —CH$_2$C(O)—, —C(O)CMe$_2$-, —CMe$_2$C(O)—, —OC(O)—, —C(O)O—, —SC(O)—, —C(O)S—, —NHC(O)—, —N(Me)C(O)—, —C(O)N(Me)-, —C(O)NH—, —S(O)=NH—, —NH=S(O)—, —N=S(O)Me-, —S(O)Me=N—,

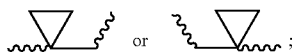 or ;

alternatively, wherein $L_1$, $L_2$, $L_1'$ and $L_2'$ are each independently selected from bond, —O—, —S—, —S(O)—, —S(O)$_2$—, —NH—, —N(Me)-, —N(CF$_3$)—, —CH$_2$—, —CH(Cl)—, —CH(F)—, —CF$_2$—, —CH(CF$_3$)—, —C(O)—, —CH$_2$CH$_2$—, —CH=CH—, —C≡C—, —OCH$_2$—, —CH$_2$O—, —SCH$_2$—, —CH$_2$S—, —S(O)CH$_2$—, —CH$_2$S(O)—, —S(O)$_2$CH$_2$—, —CH$_2$S(O)$_2$—, —NHCH$_2$—, —N(Me)CH$_2$—, —CH$_2$NH—, —CH$_2$N(Me)-, —C(O)CH$_2$—, —CH$_2$C(O)—, —C(O)CMe$_2$-, —CMe$_2$C(O)—, —OC(O)—, —C(O)O—, —SC(O)—, —C(O)S—, —NHC(O)—, —N(Me)C(O)—, —C(O)NH— or —C(O)N(Me)-.

In a more specific embodiment, the present disclosure provides a compound, or a pharmaceutically acceptable salt, enantiomer, diastereomer, racemate, solvate, hydrate, polymorph, prodrug, or isotopic variant thereof, or a mixture thereof as mentioned above, wherein E and E' are independently selected from bond, —CH$_2$CH$_2$CH$_2$—, —CH$_2$CH=CH—, —CH=CHCH$_2$—, —CH$_2$C≡C—, —C≡CCH$_2$—, —CH$_2$CH$_2$C(O)—, —CH$_2$C(O)CH$_2$—, —C(O)CH$_2$CH$_2$—, —CH$_2$CH$_2$S(O)$_2$—, —CH$_2$S(O)$_2$CH$_2$—, —S(O)$_2$CH$_2$CH$_2$—, —C(O)CH=CH—, —C(O)C≡C—, —CH$_2$CH$_2$O—, —CH$_2$OCH$_2$—, —OCH$_2$CH$_2$—, —CH$_2$CH$_2$S—, —CH$_2$SCH$_2$—, —SCH$_2$CH$_2$—, —C(O)CH$_2$O—, —OCH$_2$C(O)—, —CH$_2$C(O)O—, —C(O)CH$_2$S—, —SCH$_2$C(O)—, —CH$_2$C(O)S—, —OC(O)CH$_2$—, —C(O)OCH$_2$—, —CH$_2$OC(O)—, —SC(O)CH$_2$—, —C(O)SCH$_2$—, —CH$_2$SC(O)—, —CH$_2$CH$_2$NH—, —CH$_2$NHCH$_2$—, —NHCH$_2$CH$_2$—, —CH$_2$CH$_2$NMe-, —CH$_2$NMeCH$_2$—, —NMeCH$_2$CH$_2$—, —C(O)CH$_2$NH—, —NHCH$_2$C(O)—, —CH$_2$C(O)NH—, —NHC(O)CH$_2$—, —C(O)NHCH$_2$—, —CH$_2$NHC(O)—,

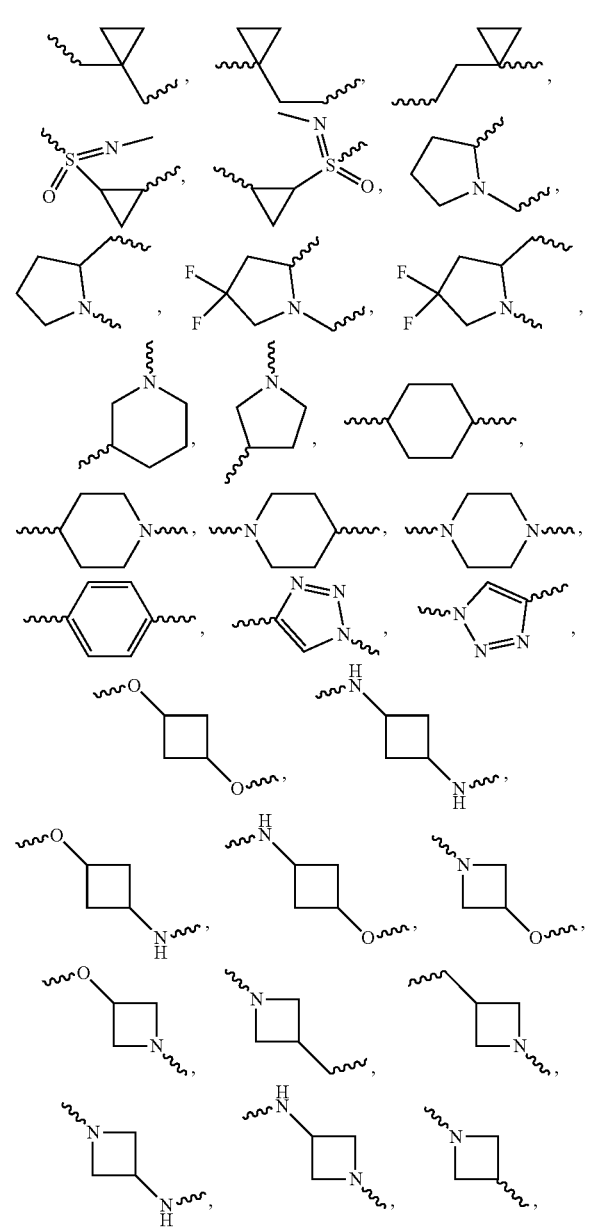

47
-continued

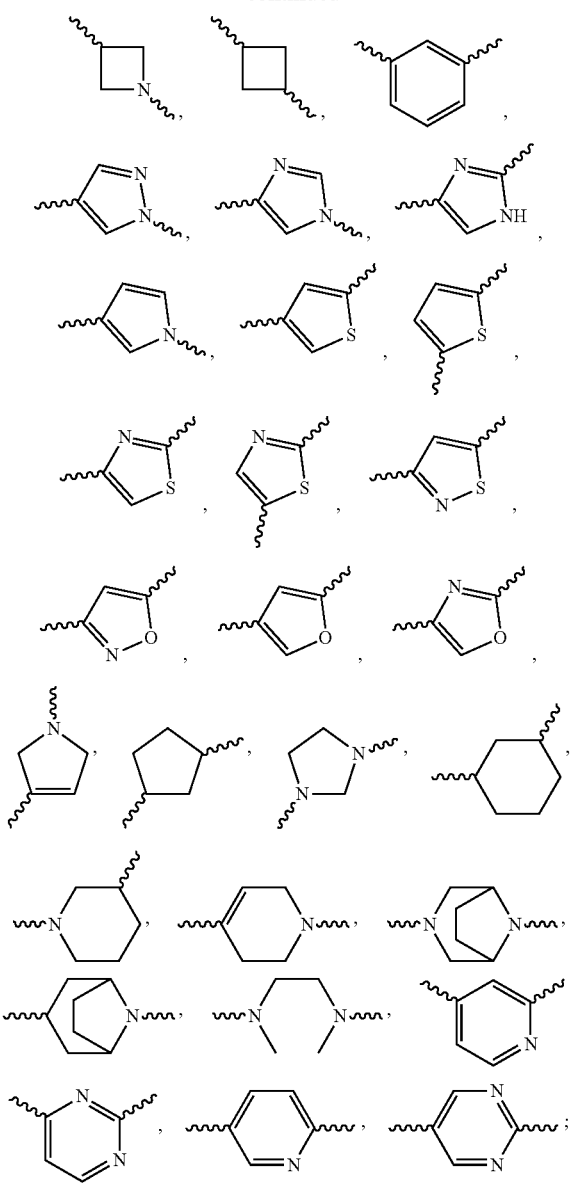

or two E moieties or two E' moieties can be taken together to form —CH₂CH₂OCH₂CH₂—, —OCH₂CH₂CH₂CH₂—, —CH₂CH₂CH₂CH₂O—,

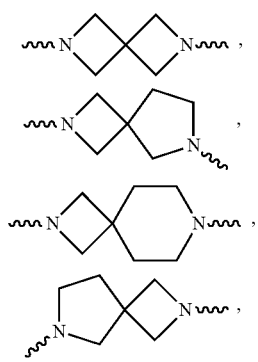

48
-continued

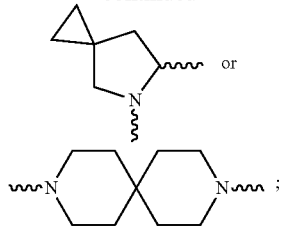

In a more specific embodiment, the present disclosure provides a compound, or a pharmaceutically acceptable salt, enantiomer, diastereomer, racemate, solvate, hydrate, polymorph, prodrug, or isotopic variant thereof, or a mixture thereof as mentioned above, wherein the ring where $X_4$, $X_5$, $X_6$ and $X_7$ are located is

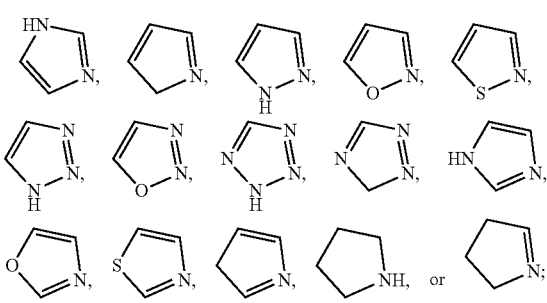

alternatively, wherein E and E' are independently selected from bond, —CH₂CH₂CH₂—, —CH₂CH=CH—, —CH=CHCH₂—, —CH₂C≡C—, —C≡CCH₂—, —CH₂CH₂C(O)—, —CH₂C(O)CH₂—, —C(O)CH₂CH₂—, —CH₂CH₂S(O)₂—, —CH₂S(O)₂CH₂—, —S(O)₂CH₂CH₂—, —C(O)CH=CH—, —C(O)C≡C—, —CH₂CH₂O—, —CH₂OCH₂—, —OCH₂CH₂—, —CH₂CH₂S—, —CH₂SCH₂—, —SCH₂CH₂—, —C(O)CH₂O—, —OCH₂C(O)—, —CH₂C(O)O—, —C(O)CH₂S—, —SCH₂C(O)—, —CH₂C(O)S—, —OC(O)CH₂—, —C(O) OCH₂—, —CH₂OC(O)—, —SC(O)CH₂—, —C(O) SCH₂—, —CH₂SC(O)—, —CH₂CH₂NH—, —CH₂NHCH₂—, —NHCH₂CH₂—, —CH₂CH₂NMe-, —CH₂NMeCH₂—, —NMeCH₂CH₂—, —C(O) CH₂NH—, —NHCH₂C(O)—, —CH₂C(O)NH—, —NHC(O)CH₂—, —C(O)NHCH₂—, —CH₂NHC (O)—,

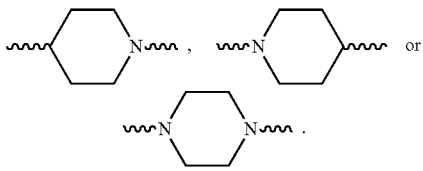

In a more specific embodiment, the present disclosure provides a compound, or a pharmaceutically acceptable salt, enantiomer, diastereomer, racemate, solvate, hydrate, polymorph, prodrug, or isotopic variant thereof, or a mixture thereof as mentioned above, wherein

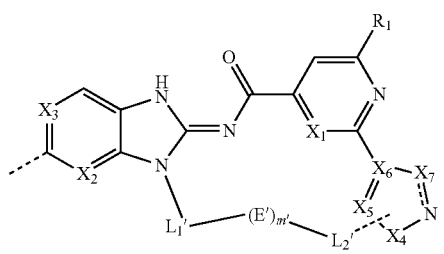
is selected from the following groups:
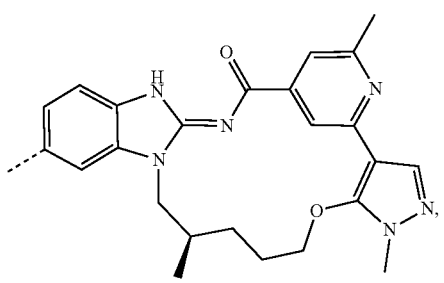
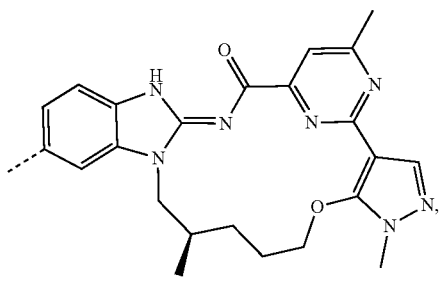
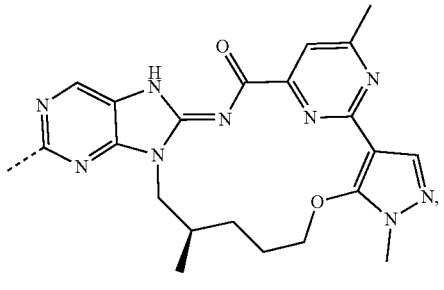
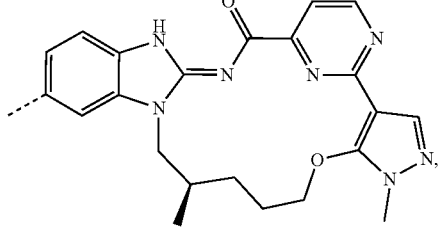
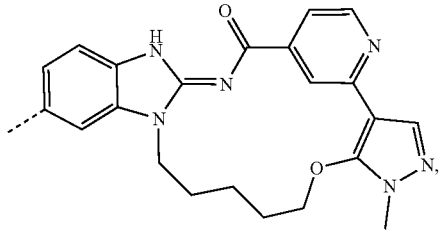
-continued
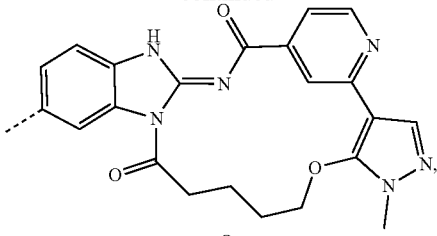
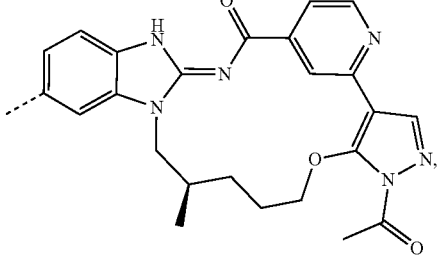
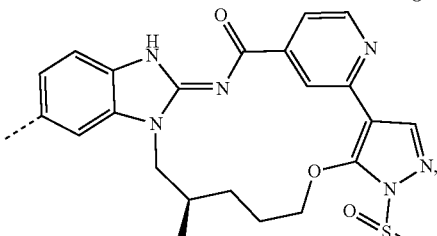
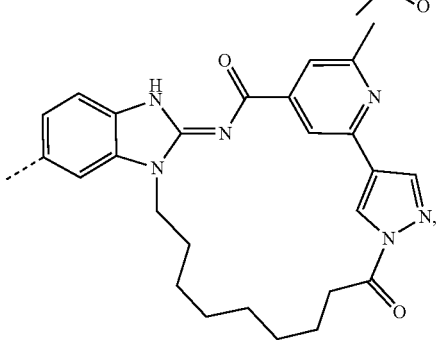
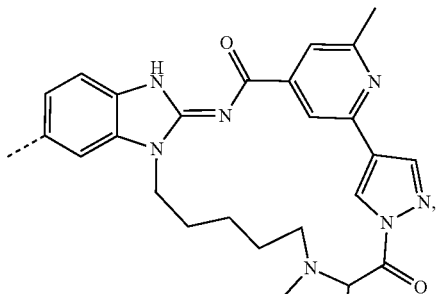
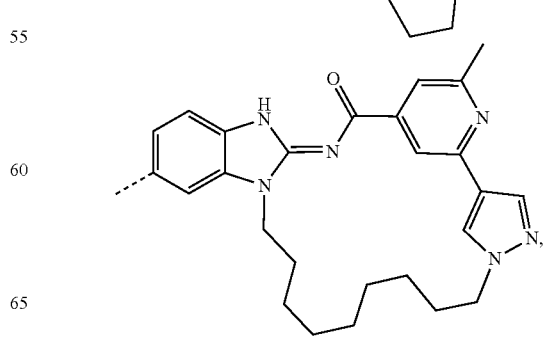

51
-continued
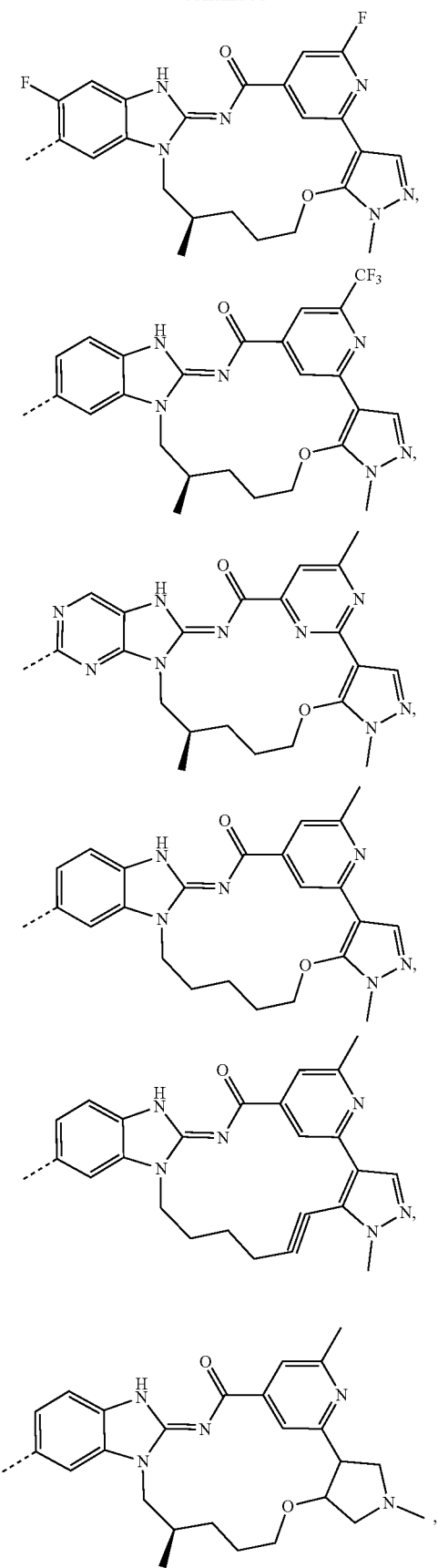
52
-continued
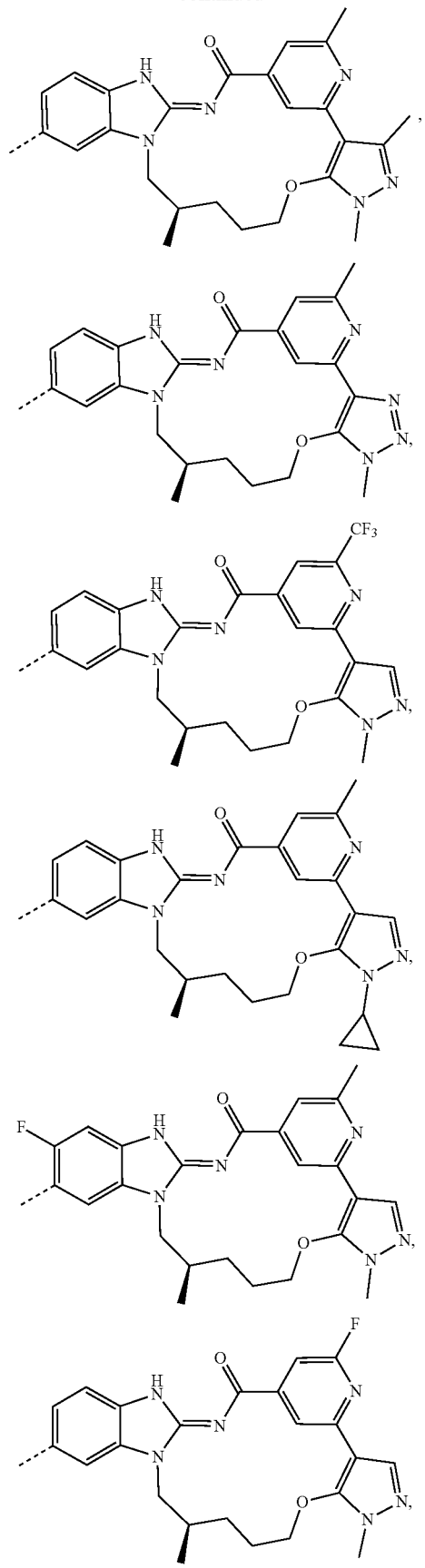

53
-continued
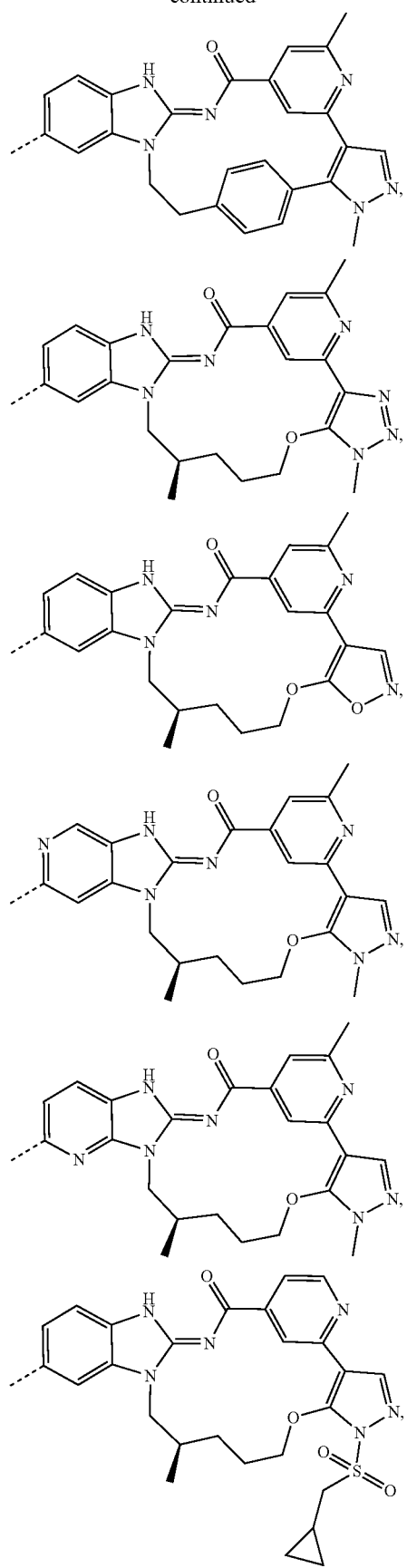
54
-continued
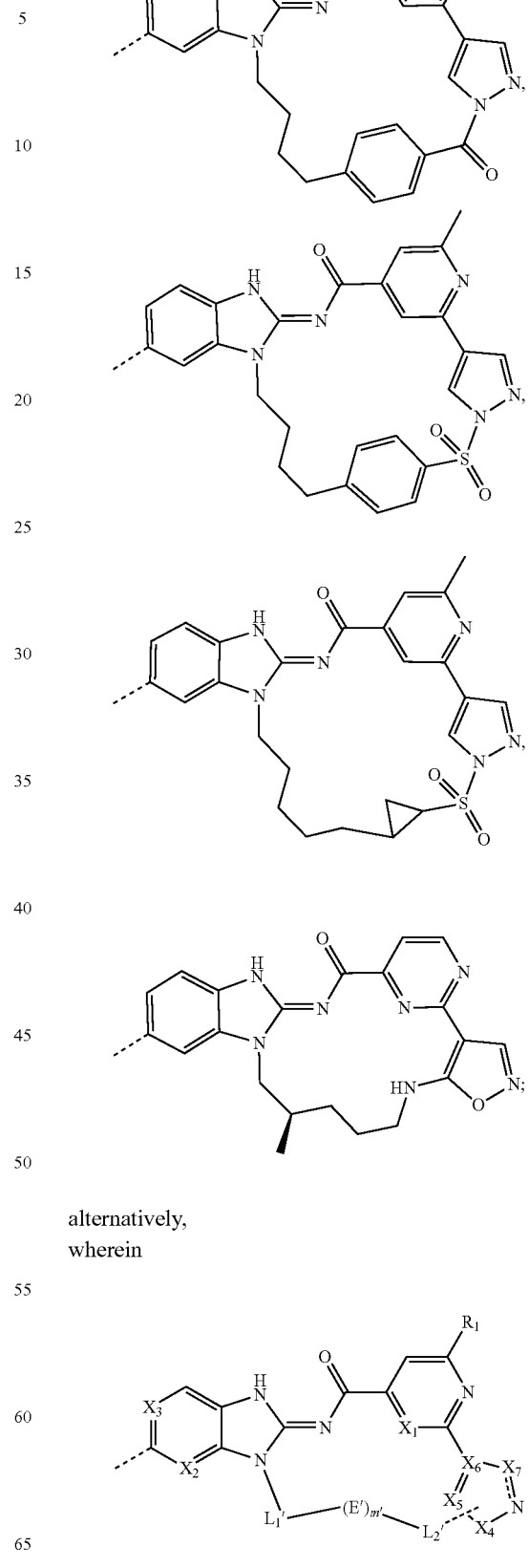
alternatively, wherein is selected from the following groups:
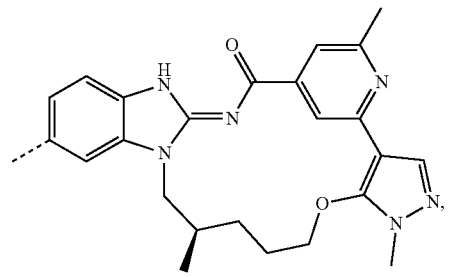
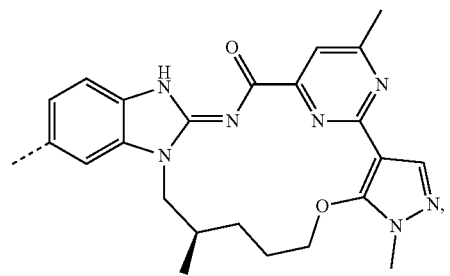
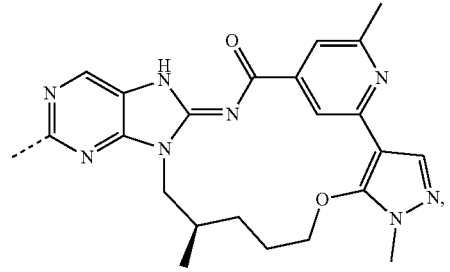
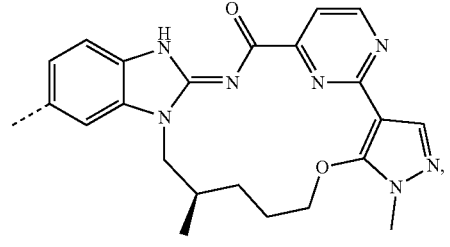
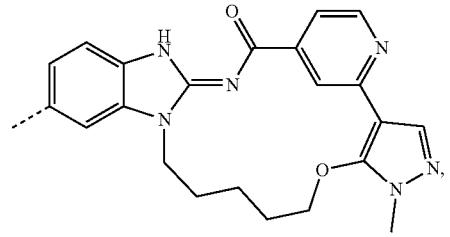
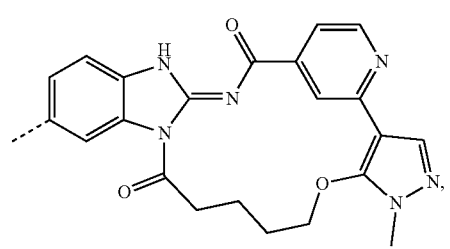
-continued
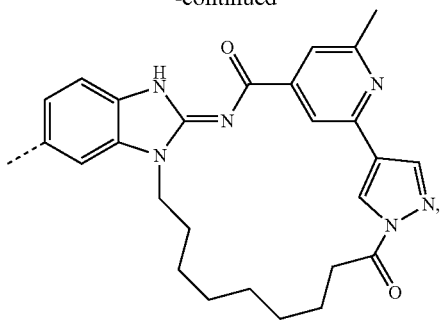
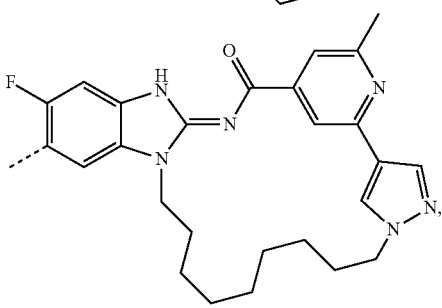
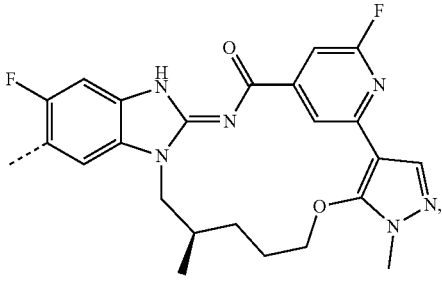
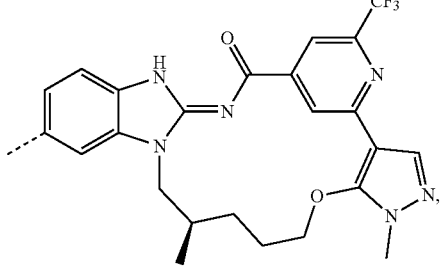
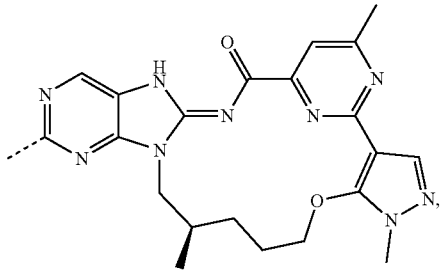
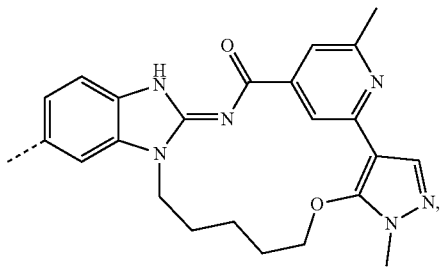

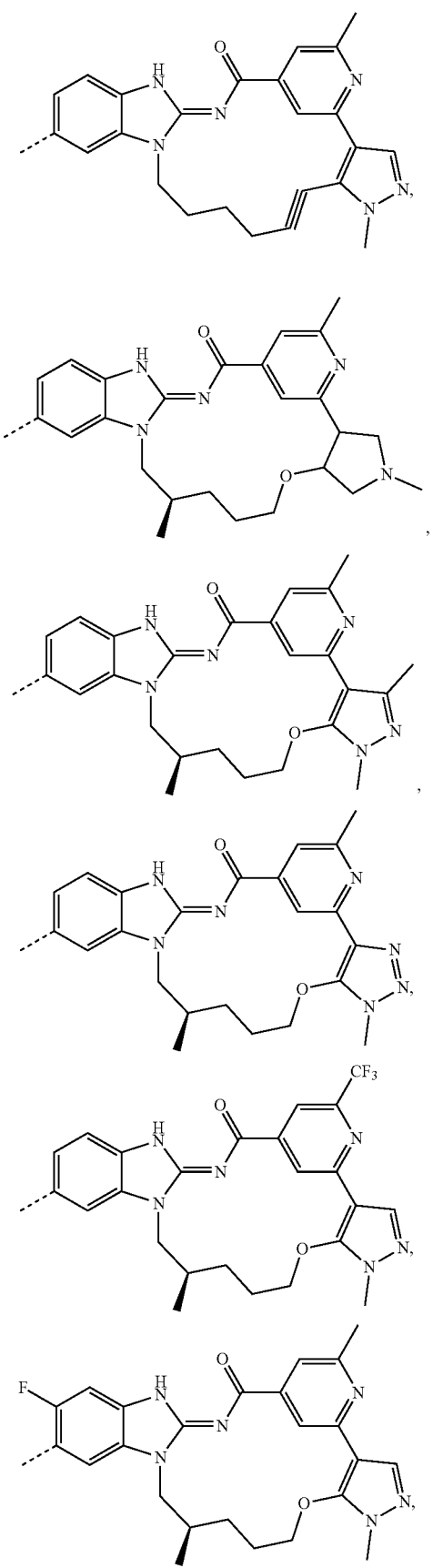
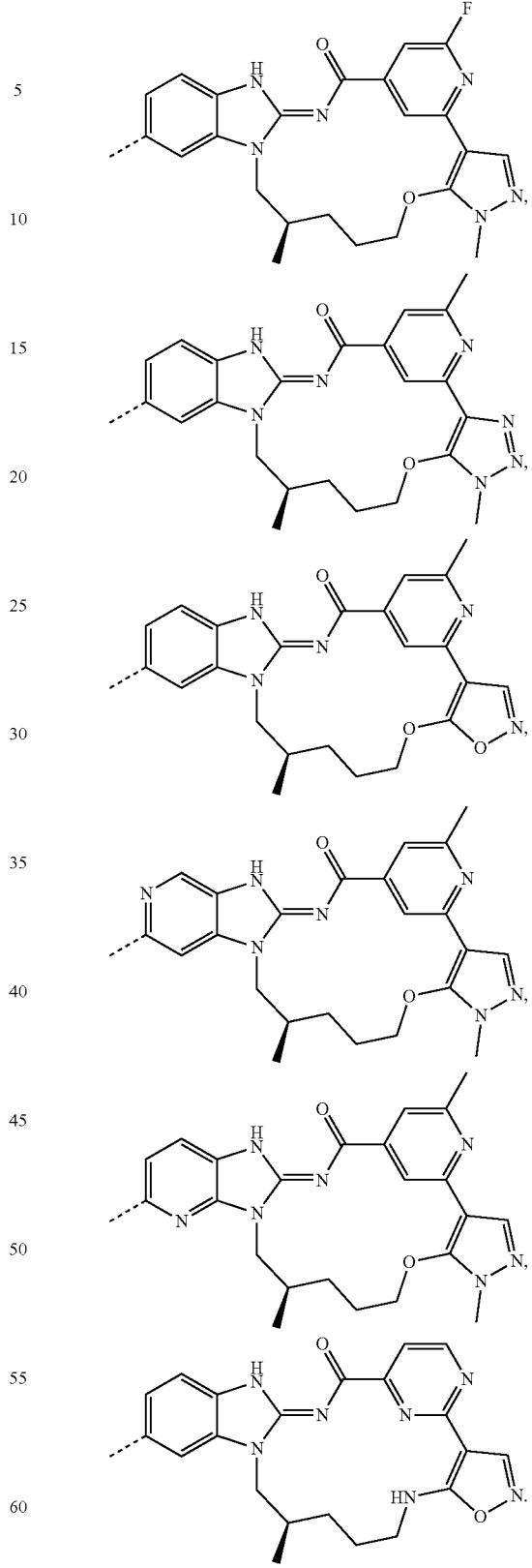
In a more specific embodiment, the present disclosure provides a compound, or a pharmaceutically acceptable salt, enantiomer, diastereomer, racemate, solvate, hydrate, polymorph, prodrug, or isotopic variant thereof, or a mixture thereof as mentioned above, which is a compound of general formula (VIII):

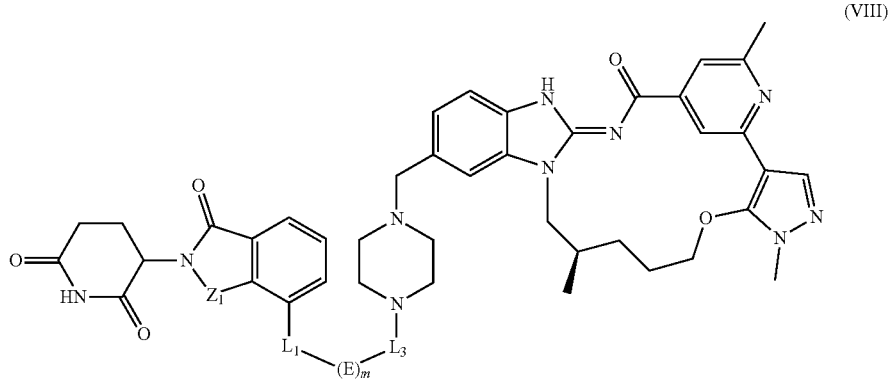

wherein
$Z_1$ is O, S, N or C atom, which is optionally substituted with one or two $R_{Z1}$;
wherein $R_{Z1}$ is H, CN, halogen, $C_{1-6}$ alkyl, or $C_{1-6}$ haloalkyl; or two $R_{Z1}$ are taken together with $Z_1$ to form C=O;
$L_1$ is selected from bond, —O—, —NR$^\#$—, —CR$^\#$R$^{\#'}$— or —C$_a$R$^\#$R$^{\#'}$C$_b$R$^\#$R$^{\#'}$—;
$L_3$ is selected from bond, —O—, —NR$^\#$—, —CR$^\#$R$^{\#'}$— or —C$_a$R$^\#$R$^{\#'}$C$_b$R$^\#$R$^{\#'}$—;
wherein one of C$_a$R$^\#$R$^{\#'}$ or C$_b$R$^\#$R$^{\#'}$ can be replaced by O, S(O)$_p$ or NR$^\#$, and when one of C$_a$R$^\#$R$^{\#'}$ or C$_b$R$^\#$R$^{\#'}$ is replaced by O, S or NR$^\#$, the other of C$_a$R$^\#$R$^{\#'}$ or C$_b$R$^\#$R$^{\#'}$ can further be replaced by S(O)$_q$;
E is independently —C$_c$R$^\#$R$^{\#'}$—C$_d$R$^\#$R$^{\#'}$—C$_e$R$^\#$R$^{\#'}$;
wherein any one of C$_c$R$^\#$R$^{\#'}$, C$_d$R$^\#$R$^{\#'}$ or C$_e$R$^\#$R$^{\#'}$, or both of C$_c$R$^\#$R$^{\#'}$ and C$_e$R$^\#$R$^{\#'}$ can be replaced by O, S(O)$_p$ or NR$^\#$, and when any one of C$_c$R$^\#$R$^{\#'}$, C$_d$R$^\#$R$^{\#'}$ or C$_e$R$^\#$R$^{\#'}$ is replaced by O, S or NR$^\#$, the other one or two of C$_c$R$^\#$R$^{\#'}$, C$_d$R$^\#$R$^{\#'}$ or C$_e$R$^\#$R$^{\#'}$ adjacent to it can further be replaced by S(O)$_q$;
p is 0, 1 or 2;
q is 1 or 2;
R$^\#$ is H, halogen, $C_{1-6}$ alkyl, $C_{1-6}$ haloalkyl, $C_{2-6}$ alkenyl or $C_{2-6}$ alkynyl;
R$^{\#'}$ is H, halogen, $C_{1-6}$ alkyl, $C_{1-6}$ haloalkyl, $C_{2-6}$ alkenyl or $C_{2-6}$ alkynyl;
or, R$^\#$ and R$^\#$ on adjacent atoms can be taken together to form bond, and R$^{\#'}$ and R$^{\#'}$ on adjacent atoms can be taken together to form bond;
or, R$^\#$ and R$^{\#'}$ on the same atom can be taken together to form =O;
m is 1, 2 or 3.

In a more specific embodiment, the present disclosure provides a compound of general formula (VIII), or a pharmaceutically acceptable salt, enantiomer, diastereomer, racemate, solvate, hydrate, polymorph, prodrug, or isotopic variant thereof, or a mixture thereof as mentioned above, wherein
$Z_1$ is —CH$_2$— or —C(O)—;
$L_1$ is selected from bond, —O—, —NH—, —CH$_2$—, —CH$_2$CH$_2$—, —CH=CH— or —C≡C—;
E is independently —CH$_2$CH$_2$CH$_2$—, —CH$_2$CH=CH—, —CH=CHCH$_2$—, —CH$_2$C≡C—, —C≡CCH$_2$—, —CH$_2$CH$_2$O—, —CH$_2$OCH$_2$—, —OCH$_2$CH$_2$—, —CH$_2$CH$_2$NH—, —CH$_2$NHCH$_2$—, —NHCH$_2$CH$_2$—, —CH$_2$CH$_2$C(O)—, —CH$_2$C(O)CH$_2$—, —C(O)CH$_2$CH$_2$—, —CH$_2$OC(O)—, —CH$_2$C(O)O—, —OC(O)CH$_2$—, —C(O)OCH$_2$—, —CH$_2$NHC(O)—, —CH$_2$C(O)NH—, —NHC(O)CH$_2$—, —C(O)NHCH$_2$—, —OCH$_2$C(O)—, —C(O)CH$_2$O—, —NHCH$_2$C(O)— or —C(O)CH$_2$NH—;
$L_3$ is selected from bond, —O—, —NH—, —CH$_2$—, —C(O)—, —CH$_2$CH$_2$—, —C(O)CH$_2$— or —CH$_2$C(O)—;
m is 1, 2 or 3.

In a more specific embodiment, the present disclosure provides a compound of general formula (VIII), or a pharmaceutically acceptable salt, enantiomer, diastereomer, racemate, solvate, hydrate, polymorph, prodrug, or isotopic variant thereof, or a mixture thereof as mentioned above, wherein
$Z_1$ is —CH$_2$— or —C(O)—;
$L_1$ is selected from bond, —O—, —NH—, —CH$_2$—, —CH$_2$CH$_2$—, —CH=CH— or —C≡C—;
E is independently —CH$_2$CH$_2$CH$_2$—, —CH$_2$CH=CH—, —CH—CHCH$_2$—, —CH$_2$C=C— or —C≡CCH$_2$—; $L_3$ is selected from bond, —O—, —NH—, —CH$_2$— or —C(O)—;
m is 1, 2 or 3.

In a more specific embodiment, the present disclosure provides a compound of general formula (VIII), or a pharmaceutically acceptable salt, enantiomer, diastereomer, racemate, solvate, hydrate, polymorph, prodrug, or isotopic variant thereof, or a mixture thereof as mentioned above, wherein
$Z_1$ is —CH$_2$— or —C(O)—;
$L_1$ is selected from bond, —O—, —NH—, —CH$_2$—, —CH$_2$CH$_2$— or —C≡C—;
E is independently —CH$_2$CH$_2$CH$_2$—;
$L_3$ is selected from bond, —CH$_2$— or —C(O)—;
m is 1 or 2.

In a more specific embodiment, the present disclosure provides a compound of general formula (VIII), or a pharmaceutically acceptable salt, enantiomer, diastereomer, racemate, solvate, hydrate, polymorph, prodrug, or isotopic variant thereof, or a mixture thereof as mentioned above, wherein $Z_1$ is —$CH_2$—;
$L_1$ is selected from bond, —$CH_2$—, —$CH_2CH_2$— or —C≡C—;
E is independently —$CH_2CH_2CH_2$—;
$L_3$ is selected from bond or —$CH_2$—;
m is 1 or 2.

In a more specific embodiment, the present disclosure provides a compound, or a pharmaceutically acceptable salt, enantiomer, diastereomer, racemate, solvate, hydrate, polymorph, prodrug, or isotopic variant thereof, or a mixture thereof as mentioned above, which is a compound of general formula (VIII):

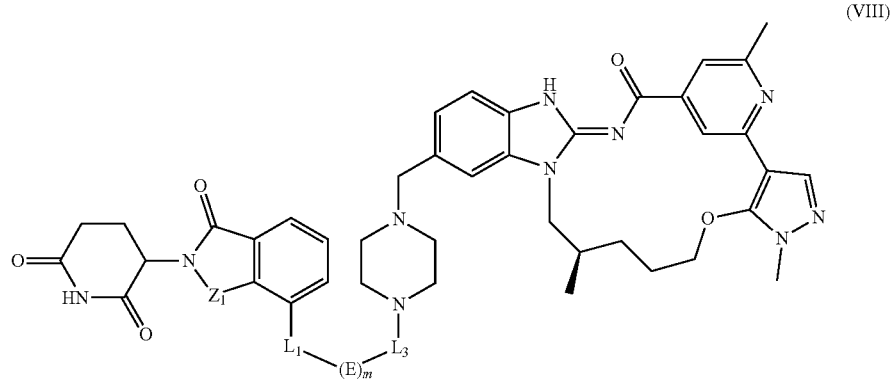

(VIII)

wherein
$Z_1$ is O, S, N or C atom, which is optionally substituted with one or two $R_{Z1}$;
$R_{Z1}$ is H, CN, halogen, $C_{1-6}$ alkyl, or $C_{1-6}$ haloalkyl; or two $R_{Z1}$ are taken together with $Z_1$ to form C—O;
$L_1$ is selected from bond, —O—, —$NR^\#$—, —$CR^\#R^{\#'}$— or —$C_aR^\#R^{\#'}C_bR^\#R^{\#'}$—;
$L_3$ is selected from bond, —O—, —$NR^\#$—, —$CR^\#R^{\#'}$— or —$C_aR^\#R^{\#'}C_bR^\#R^{\#'}$—;
E is —$C_cR^\#R^{\#'}$—$C_dR^\#R^{\#'}$—$C_eR^\#R^{\#'}$;
wherein one of $C_cR^\#R^{\#'}$ or $C_eR^\#R^{\#'}$ can be replaced by O, $S(O)_p$ or $NR^\#$;
p is 0, 1 or 2;
$R^\#$ is H, halogen, $C_{1-6}$ alkyl, $C_{1-6}$ haloalkyl, $C_{2-6}$ alkenyl or $C_{2-6}$ alkynyl;
$R^{\#'}$ is H, halogen, $C_{1-6}$ alkyl, $C_{1-6}$ haloalkyl, $C_{2-6}$ alkenyl or $C_{2-6}$ alkynyl;
or, $R^\#$ and $R^\#$ on adjacent atoms can be taken together to form bond, and $R^{\#'}$ and $R^{\#'}$ on adjacent atoms can be taken together to form bond;
or, $R^\#$ and $R^{\#'}$ on the same atom can be taken together to form =O;
m is 1.

In a more specific embodiment, the present disclosure provides a compound of general formula (VIII), or a pharmaceutically acceptable salt, enantiomer, diastereomer, racemate, solvate, hydrate, polymorph, prodrug, or isotopic variant thereof, or a mixture thereof as mentioned above, wherein
$Z_1$ is —$CH_2$— or —C(O)—;
$L_1$ is selected from bond, —O—, —NH—, —$CH_2$—, —$CH_2CH_2$—, —CH=CH— or —C≡C—;
E is —$CH_2CH_2CH_2$—, —$CH_2CH$=CH—, —CH=$CHCH_2$—, —$CH_2C$≡C—, —C≡$CCH_2$—, —$CH_2CH_2C(O)$—, —$CH_2C(O)CH_2$—, —C(O)$CH_2CH_2$—, —$OCH_2C(O)$—, —$C(O)CH_2O$—, —$NHCH_2C(O)$— or —$C(O)CH_2NH$—;
$L_3$ is selected from bond, —O—, —NH—, —$CH_2$—, —C(O)—, —$CH_2CH_2$—, —$C(O)CH_2$— or —$CH_2C(O)$—;
m is 1.

In a more specific embodiment, the present disclosure provides a compound of general formula (VIII), or a pharmaceutically acceptable salt, enantiomer, diastereomer, racemate, solvate, hydrate, polymorph, prodrug, or isotopic variant thereof, or a mixture thereof as mentioned above, wherein
$Z_1$ is —$CH_2$— or —C(O)—;
$L_1$ is selected from bond, —O—, —NH—, —$CH_2$—, —$CH_2CH_2$—, —CH=CH— or —C≡C—;
E is —$CH_2CH_2CH_2$—, —$CH_2CH$=CH—, —CH=$CHCH_2$—, —$CH_2C$=C— or —C≡$CCH_2$—;
$L_3$ is selected from bond, —O—, —NH—, —$CH_2$— or —C(O)—;
m is 1.

In a more specific embodiment, the present disclosure provides a compound of general formula (VIII), or a pharmaceutically acceptable salt, enantiomer, diastereomer, racemate, solvate, hydrate, polymorph, prodrug, or isotopic variant thereof, or a mixture thereof as mentioned above, wherein
$Z_1$ is —$CH_2$— or —C(O)—;
$L_1$ is selected from bond, —O—, —NH—, —$CH_2$—, —$CH_2CH_2$— or —C≡C—;
E is —$CH_2CH_2CH_2$—;
$L_3$ is selected from bond, —$CH_2$— or —C(O)—;
m is 1.

In a more specific embodiment, the present disclosure provides a compound of general formula (VIII), or a pharmaceutically acceptable salt, enantiomer, diastereomer, racemate, solvate, hydrate, polymorph, prodrug, or isotopic variant thereof, or a mixture thereof as mentioned above, wherein
$Z_1$ is —$CH_2$—;
$L_1$ is selected from bond, —$CH_2$—, —$CH_2CH_2$— or —C≡C—;
E is —$CH_2CH_2CH_2$—;
$L_3$ is selected from bond or —$CH_2$—;
m is 1.

In a more specific embodiment, the present disclosure provides a compound, or a pharmaceutically acceptable salt, enantiomer, diastereomer, racemate, solvate, hydrate, polymorph, prodrug, or isotopic variant thereof, or a mixture thereof as mentioned above, wherein the compound is selected from:
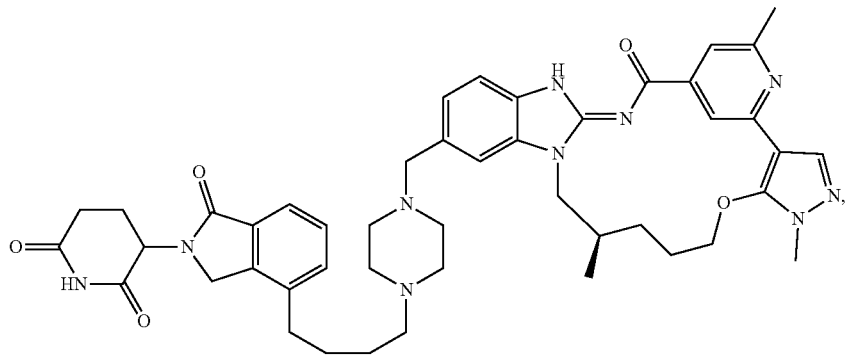
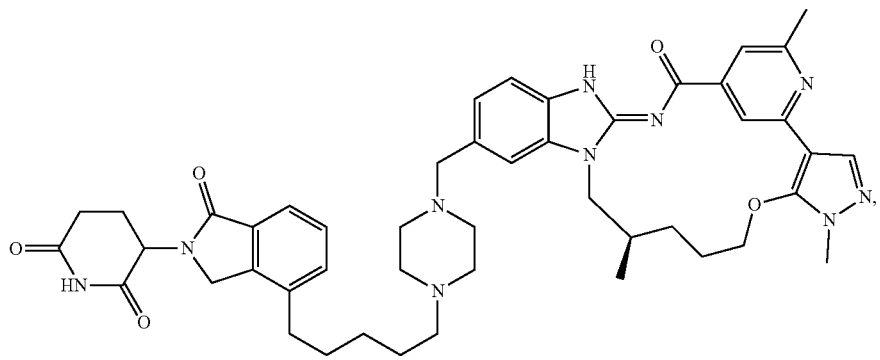
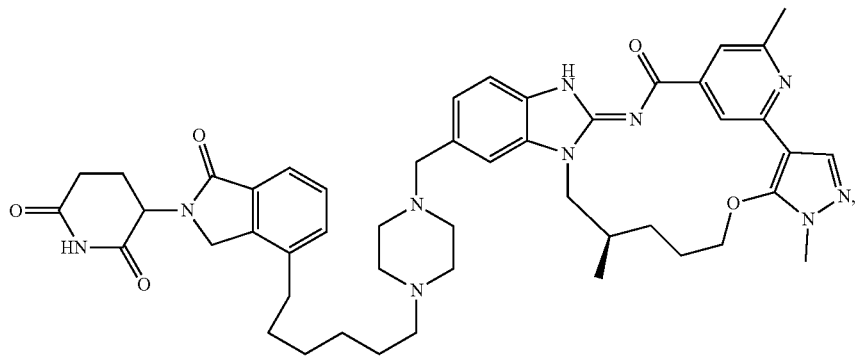
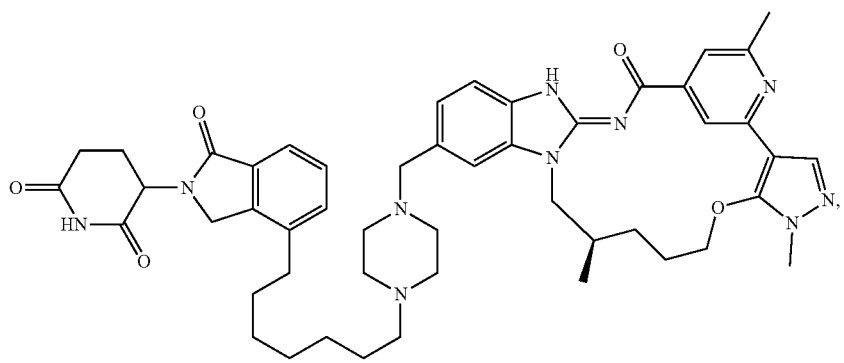

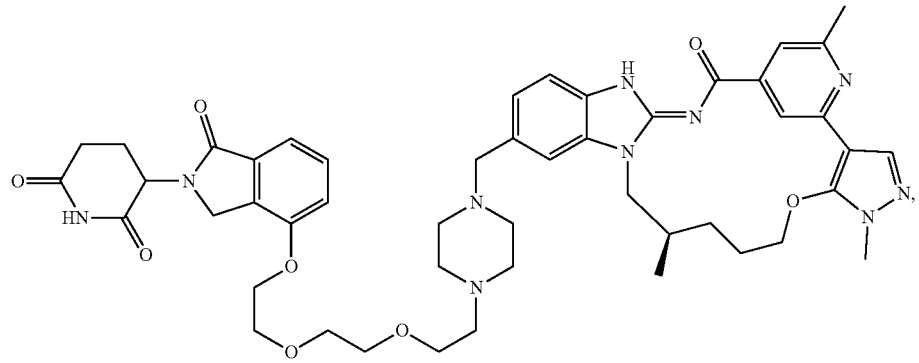
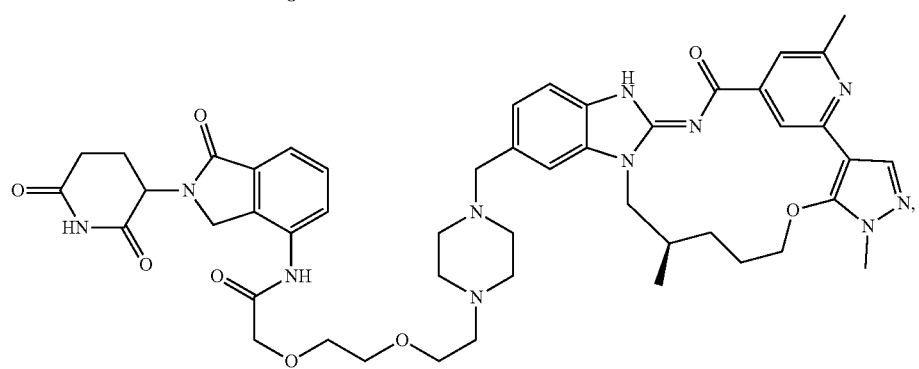
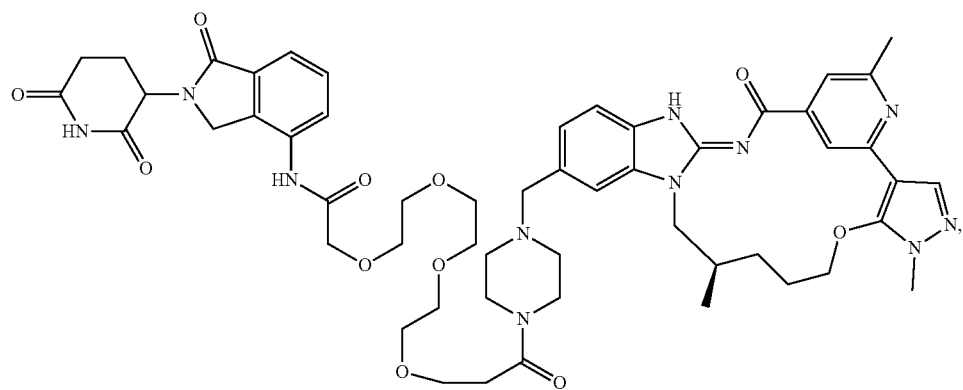
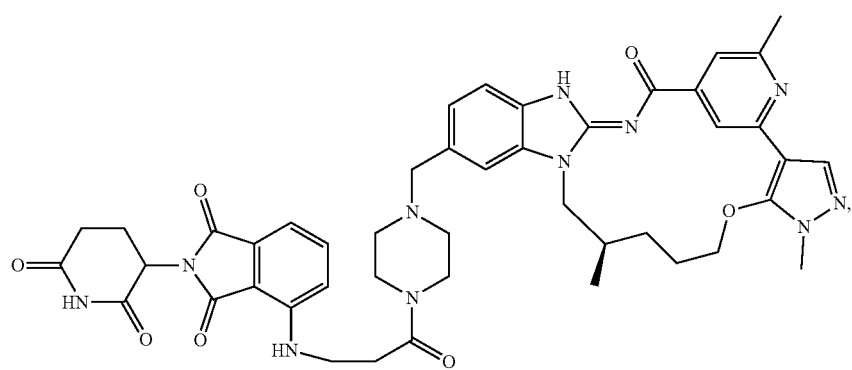

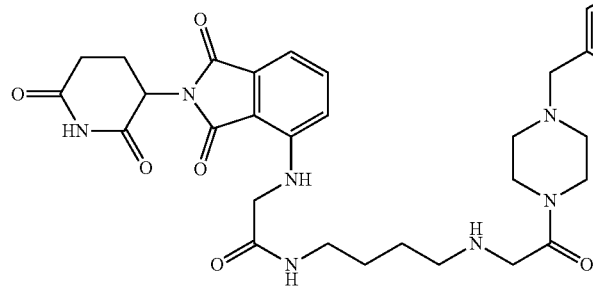
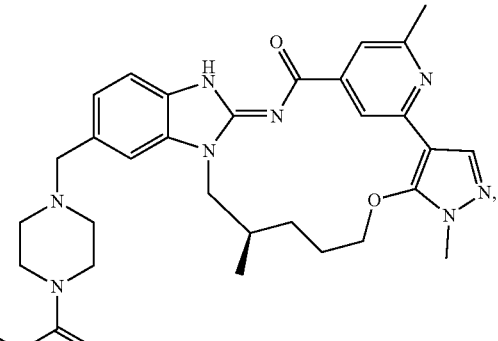
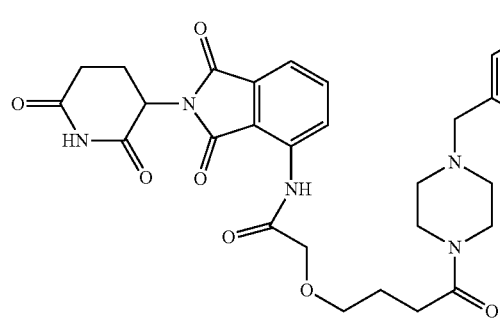
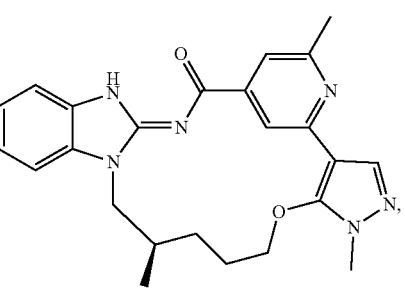
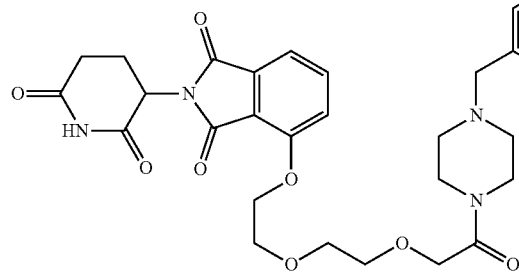
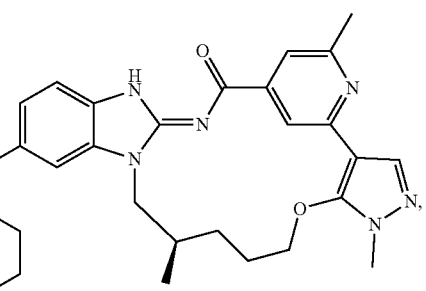
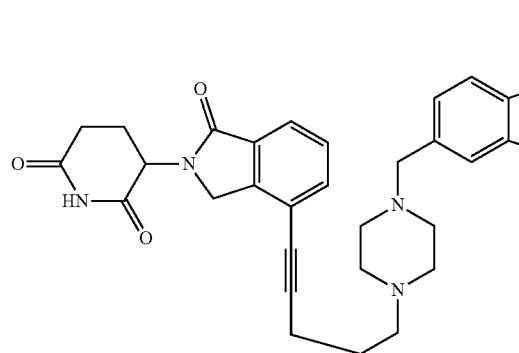
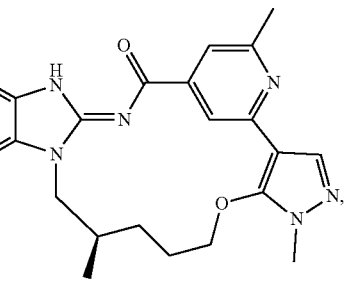

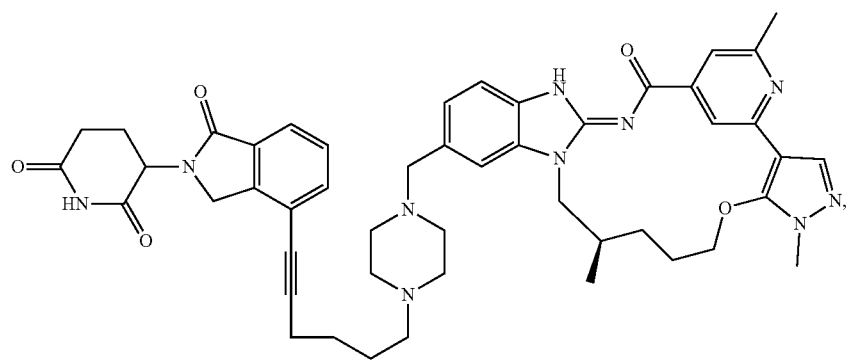
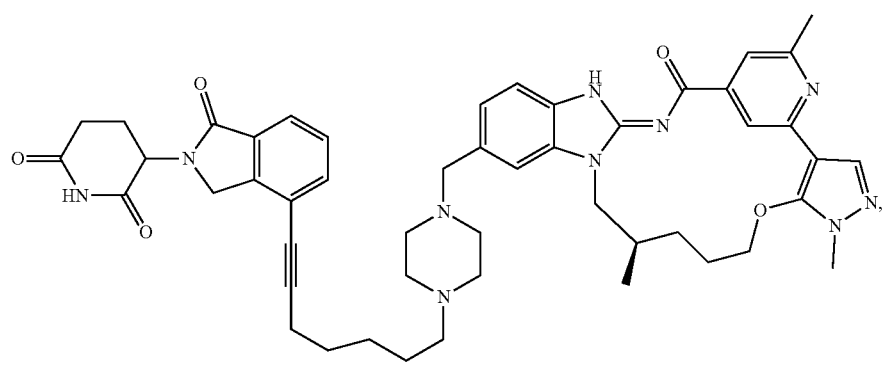
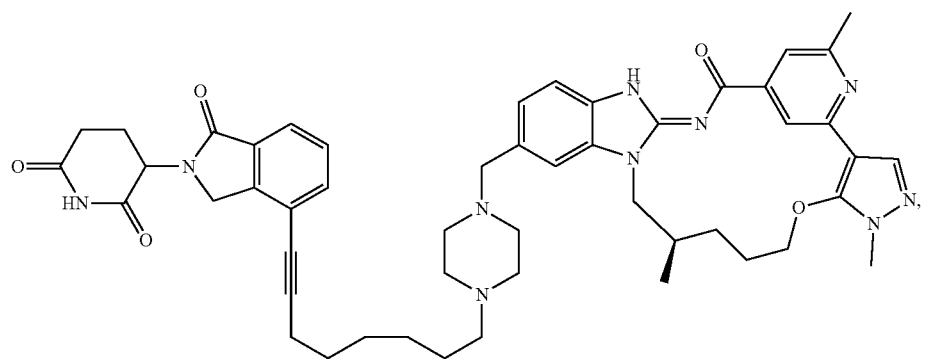
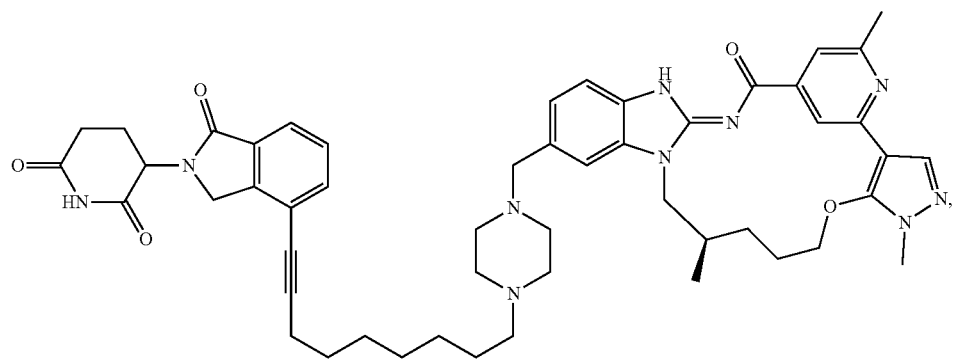

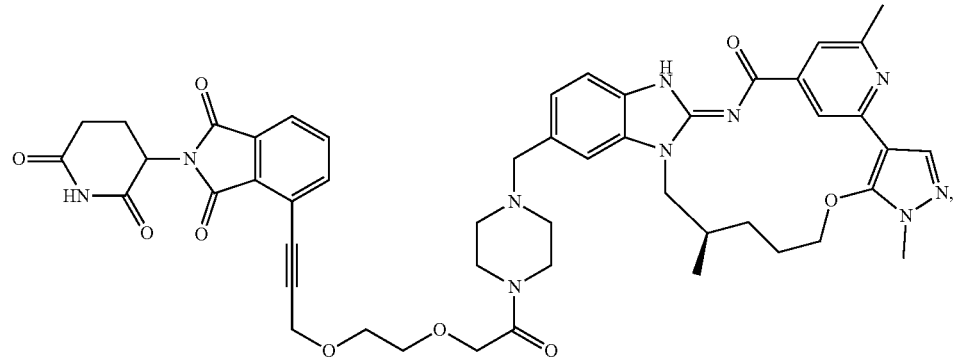
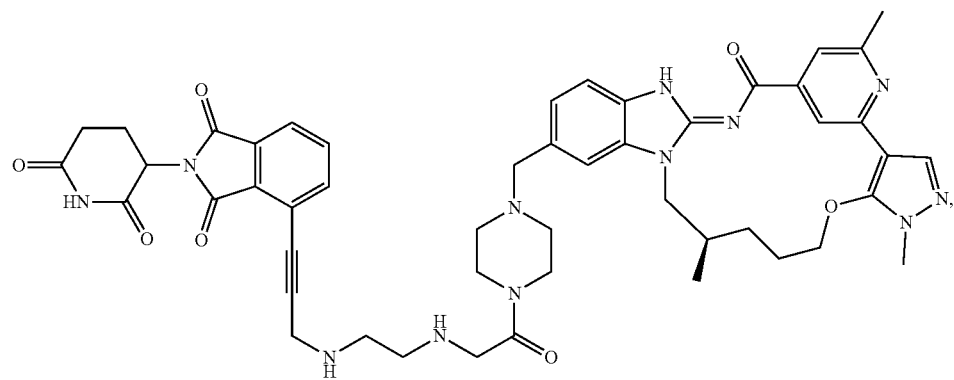
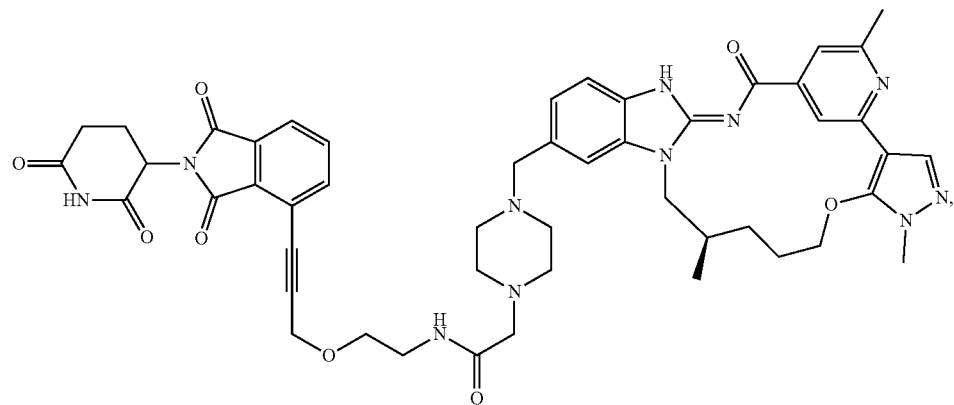
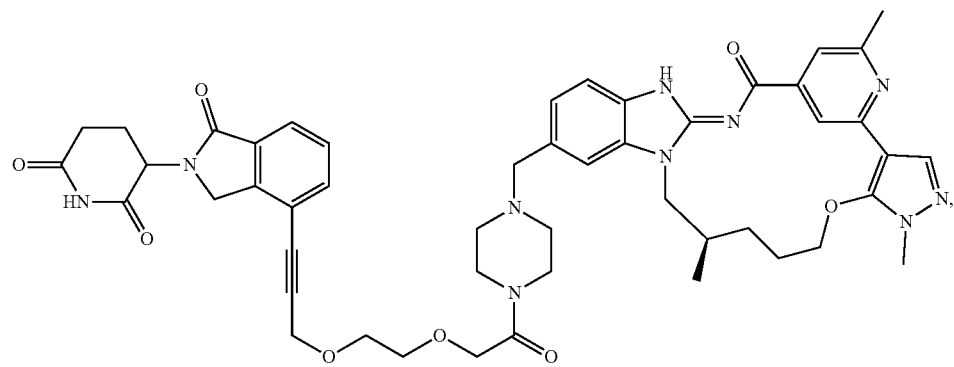

-continued

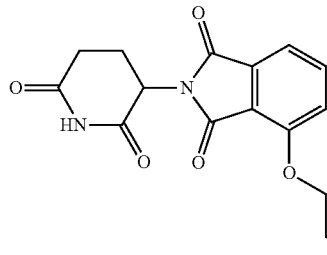
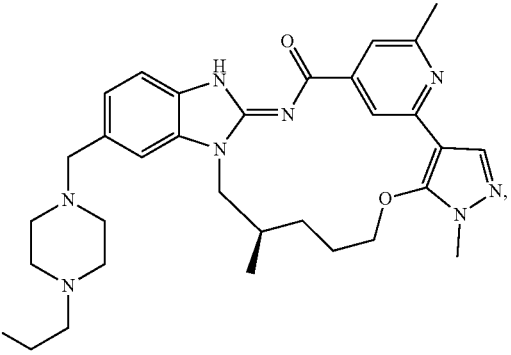

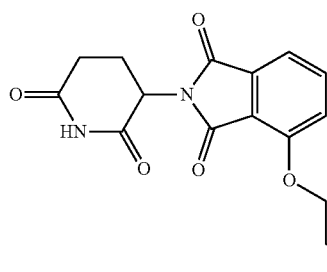
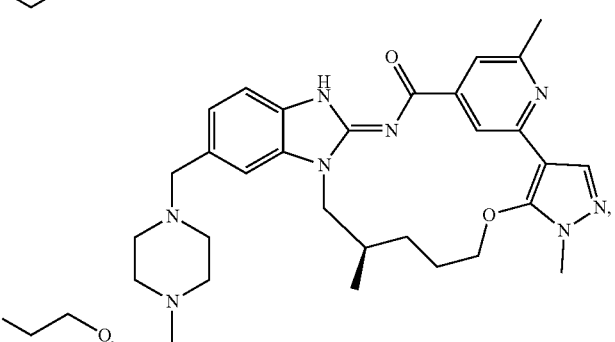

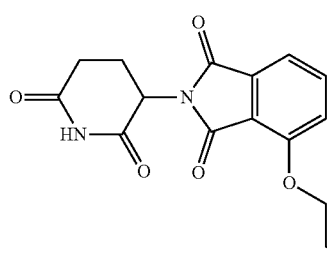
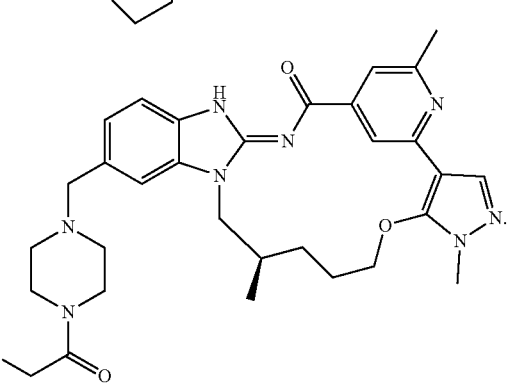

The compounds of the present disclosure may include one or more asymmetric centers, and thus may exist in a variety of stereoisomeric forms, for example, enantiomers and/or diastereomers. For example, the compounds of the present disclosure may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or alternative isomers can be prepared by asymmetric synthesis.

It will be understood by those skilled in the art that the organic compounds can form complexes with solvents in which they are reacted or from which they are precipitated or crystallized. These complexes are known as "solvates." Where the solvent is water, the complex is known as "hydrate." The present disclosure encompasses all solvates of the compounds of the present disclosure.

The term "solvate" refers to forms of a compound or a salt thereof, which are associated with a solvent, usually by a solvolysis reaction. This physical association may include hydrogen bonding. Conventional solvents include water, methanol, ethanol, acetic acid, DMSO, THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula $R \cdot xH_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates (R·0.5H$_2$O)) and polyhydrates (x is a number greater than 1, for example, dihydrates (R·2H$_2$O) and hexahydrates (R·6H$_2$O)).

Compounds of the present disclosure may be in an amorphous or a crystalline form (polymorph). Furthermore, the compounds of the present disclosure may exist in one or more crystalline forms. Therefore, the present disclosure includes all amorphous or crystalline forms of the compounds of the present disclosure within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

The present disclosure also comprises compounds that are labeled with isotopes (isotope variants), which are equivalent to those described in formula (I), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^2$H, $^3$H, $^{13}$C, $^{11}$C, $^{14}$C, $^{15}$N, $^{18}$O, $^{17}$O, $^{31}$P, $^{32}$P, $^{35}$S, $^{18}$F and $^{36}$Cl, respectively. Compounds of the present disclosure that comprise the above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^3$H and $^{14}$C), can be used for the measurement of the distribution of drug and/or substrate in tissue. Tritium, which is $^3$H and carbon-14, which is $^{14}$C isotope, are yet alternative, because they are easy to prepare and detect. Furthermore, replaced by heavier isotopes, such as deuterium, which is $^2$H, may provide therapeutic benefits due to the higher metabolic stability, such as prolonging the half-life in vivo or decreasing the dosage requirements, and thus may be alternative in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

In addition, prodrugs are also included within the context of the present disclosure. The term "prodrug" as used herein refers to a compound that is converted into an active form that has medical effects in vivo by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19 (2) 115-130, each of which are incorporated herein by reference.

The prodrugs are any covalently bonded compounds of the present disclosure, which release the parent compound in vivo when the prodrug is administered to a patient. Prodrugs are typically prepared by modifying functional groups in such a way that the modifications can be cleaved either by routine manipulation or decompose in vivo to yield the parent compound. Prodrugs include, for example, compounds of the present disclosure wherein the hydroxyl, amino or sulfhydryl groups are bonded to any group that, when administered to a patient, cleaves to form the hydroxyl, amino or sulfhydryl groups. Thus, representative examples of prodrugs include (but are not limited to) the acetate/acetamide, formate/formamide and benzoate/benzamide derivatives of the hydroxyl, amino or sulfhydryl functional groups of the compounds of formula (I). Furthermore, in the case of carboxylic acid (—COOH), esters such as methyl esters and ethyl esters, etc. can be employed. The ester itself may be active in their own and/or hydrolyzable under in vivo conditions in the human body. Suitable pharmaceutically acceptable in vivo hydrolysable ester groups include those groups that can readily break down in the human body to release the parent acids or salts thereof.

The present disclosure also provides a pharmaceutical formulation comprising a therapeutically effective amount of a compound of formula (I), or therapeutically acceptable salts thereof, and pharmaceutically acceptable carriers, diluents or excipients thereof. All of these forms belong to the present disclosure.

Pharmaceutical Compositions and Kits

In another aspect, the present disclosure provides a pharmaceutical composition comprising a compound of the present disclosure (also referred to as the "active ingredient") and a pharmaceutically acceptable excipient. In certain embodiments, the pharmaceutical composition comprises an effective amount of the compound of the present disclosure. In certain embodiments, the pharmaceutical composition comprises a therapeutically effective amount of the compound of the present disclosure. In certain embodiments, the pharmaceutical composition comprises a prophylactically effective amount of the compound of the present disclosure.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that may be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (e.g., vials, ampoules, bottles, syringes, and/or dispersible packages or other materials) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

Administration

The pharmaceutical composition provided by the present disclosure can be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present disclosure may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or alternatively from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with alternative doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, alternatively from about 0.1 to about 20% by weight, alternatively from about 0.1 to about 10% by weight, and still alternatively from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device.

Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pennsylvania, which is incorporated herein by reference.

The compounds of the present disclosure can also be administered in sustained release forms or from sustained release drug delivery systems. A description of representative sustained release materials can be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In certain embodiments, the formulation comprises hexapropyl-β-cyclodextrin (e.g., 10-50% in water).

Treatment

As stated herein, it is known that EGFR kinase have roles in tumourigenesis as well as numerous other diseases. We have found that the compounds of the present disclosure possess potent anti-tumour activity which it is believed is afforded by way of inhibition of EGFR kinase.

The compounds of the present disclosure are of value as anti-tumour agents. Particularly, the compounds of the present disclosure are of value as anti-proliferative, apoptotic and/or anti-invasive agents in the containment and/or treatment of solid and/or liquid tumour disease. Particularly, the compounds of the present disclosure are expected to be useful in the prevention or treatment of those tumours which are sensitive to inhibition of EGFR. Further, the compounds of the present disclosure are expected to be useful in the prevention or treatment of those tumours which are mediated alone or in part by EGFR. The compounds may thus be used to produce an EGFR enzyme inhibitory effect in a warm-blooded animal in need of such treatment.

As stated herein, inhibitors of EGFR kinase should be of therapeutic value for the treatment of cancer, such as ovarian cancer, cervical cancer, colorectal cancer, breast cancer, pancreatic cancer, glioma, glioblastoma, melanoma, prostate cancer, leukemia, lymphoma, non-Hodgkin's lymphoma, gastric cancer, lung cancer, hepatocellular cancer, stomach cancer, gastrointestinal stromal tumor (GIST), thyroid cancer, cancer of bile duct, endometrial cancer, kidney cancer, anaplastic large cell lymphoma, acute myeloid leukemia (AML), multiple myeloma, melanoma, and mesothelioma.

Anti-cancer effects which are accordingly useful in the treatment of cancer in a patient include, but are not limited to, anti-tumour effects, the response rate, the time to disease progression and the survival rate. Anti-tumour effects of a method of treatment of the present disclosure include but are not limited to, inhibition of tumour growth, tumour growth delay, regression of tumour, shrinkage of tumour, increased time to regrowth of tumour on cessation of treatment, slowing of disease progression. Anti-cancer effects include prophylactic treatment as well as treatment of existing disease.

A EGFR kinase inhibitor, or a pharmaceutically acceptable salt thereof, may also be useful for the treatment patients with cancers, including, but not limited to, haematologic malignancies such as leukaemia, multiple myeloma, lymphomas such as Hodgkin's disease, non-Hodgkin's lymphomas (including mantle cell lymphoma), and myelodysplastic syndromes, and also solid tumours and their metastases such as breast cancer, lung cancer (non-small cell lung cancer (NSCL), small cell lung cancer (SCLC), squamous cell carcinoma), endometrial cancer, tumours of the central nervous system such as gliomas, dysembryoplastic neuroepithelial tumour, glioblastoma multiforme, mixed gliomas, medulloblastoma, retinoblastoma, neuroblastoma, germinoma and teratoma, cancers of the gastrointestinal tract such as gastric cancer, oesophagal cancer, hepatocellular (liver) carcinoma, cholangiocarcinomas, colon and rectal carcinomas, cancers of the small intestine, pancreatic cancers, cancers of the skin such as melanomas (in particular metastatic melanoma), thyroid cancers, cancers of the head and neck and cancers of the salivary glands, prostate, testis, ovary, cervix, uterus, vulva, bladder, kidney (including renal cell carcinoma, clear cell and renal oncocytoma), squamous cell carcinomas, sarcomas such as osteosarcoma, chondrosarcoma, leiomyosarcoma, soft tissue sarcoma, Ewing's sarcoma, gastrointestinal stromal tumour (GIST), Kaposi's sarcoma, and paediatric cancers such as rhabdomyosarcomas and neuroblastomas.

The effective dose of the compound of the present disclosure is usually at an average daily dose of 0.01 mg to 50 mg compound/kg of patient weight, alternatively 0.1 mg to 25 mg compound/kg of patient weight, in single or multiple administrations. Generally, the compound of the present disclosure can be administered to the patient who needs this treatment in the daily dose range of about 1 mg to about 3500 mg per patient, alternatively 10 mg to 1000 mg. For example, the daily dose per patient can be 10, 20, 30, 40, 50, 60, 70, 80, 90, 100, 150, 200, 250, 300, 350, 400, 500, 600, 700, 800, 900 or 1000 mg. It can be administered once or several times a day, weekly (or several days apart) or on an intermittent schedule. For example, on a weekly basis (e.g. every Monday), the compound can be administered one or more times a day, variably for several weeks, for example 4-10 weeks. Or, the compound may be administered daily for several days (e.g. 2-10 days), and then a few days (e.g. 1-30 days) without administering the compound, repeating the cycle arbitrarily or repeating a given number of times, e.g. 4-10 cycles. For example, the compound of the present disclosure can be administered daily for 5 days, and then interrupted for 9 days, and then administered daily for 5 days, then interrupted for 9 days, and so on, repeating the cycle arbitrarily or repeating 4-10 times in total.

Combination Therapy

The treatment defined herein may be applied as a sole therapy or may involve, in addition to the compounds of the present disclosure, conventional surgery or radiotherapy or chemotherapy. Accordingly, the compounds of the present disclosure can also be used in combination with existing therapeutic agents for the treatment of cancer.

In addition to the compound disclosed herein, conventional surgery, radiotherapy, chemotherapy, or immunotherapy can be used for the treatment. Such chemotherapy can be administered simultaneously, sequentially or separately with the compound disclosed herein and may include one or more of the following categories of anti-tumour agents:

(i) antiproliferative/antineoplastic drugs and combinations thereof, as used in medical oncology, such as alkylating agents (for example czs-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl) ethoxy]-5-tetrahydropyran-4-yloxyquinazoline [AZD0530 (saracatinib)], N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825) and bosutinib (SKI-606), and metalloproteinase inhibitors like marimastat, inhibitors of urokinase plasminogen activator receptor function or antibodies to heparanase];

(iv) inhibitors of growth factor function: for example such inhibitors include growth factor antibodies and growth factor receptor antibodies (for example the anti-erbB2 antibody trastuzumab [Herceptin], the anti-EGFR antibody panitumumab and the anti-erbB1 antibody cetuximab [Erbitux, C225]); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)-quinazolin-4-amine (gefitinib, ZD 1839), N-(3-ethynylphenyl)-6,7-bis(2-methoxyethoxy) quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (RI 15777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF—IR kinase inhibitors, IGF receptor (insulinlike growth factor) kinase inhibitors; aurora kinase inhibitors (for example AZD1152, PH739358, VX-680, MLN8054, R763, MP235, MP529, VX-528 and AX39459) and cyclin dependent kinase inhibitors such as CDK2 and/or CDK4 inhibitors;

(v) antiangiogenic agents such as those which inhibit the effects of vascular endothelial growth factor, [for example the anti-human vascular endothelial cell growth factor antibody bevacizumab (Avastin) and for example, a VEGF receptor tyrosine kinase inhibitor such as vandetanib (ZD6474), vatalanib (PTK787), sunitinib (*SUI* 1248), axitinib (AG-013736), pazopanib (GW 786034) and 4-(4-fiuoro-2-methylindol-5-yloxy)-6-methoxy-7-(3-pyrrolidin-1-ylpropoxy) quinazoline (AZD2171) and compounds that work by other mechanisms (for example linomide, inhibitors of integrin αvβ3 function and angiostatin)];

(vi) vascular damaging agents such as combretastatin A4;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines, approaches using anti-idiotypic antibodies, approaches to decrease the function of immune suppressive cells such as regulatory T cells, myeloid-derived suppressor cells or IDO (indoleamine 2,3,-deoxygenase)-expressing dendritic cells, and approaches using cancer vaccines consisting of proteins or peptides derived from tumour-associated antigens such as NY-ESO-1, MAGE-3, WTI or Her2/neu.

EXAMPLES

The materials or reagents used herein are commercially available or are prepared by synthetic methods generally known in the art.

Preparation of Intermediates

Preparation of 3-(4-bromo-1-oxoisoindolin-2-yl)piperidine-2,6-dione (D1-1)

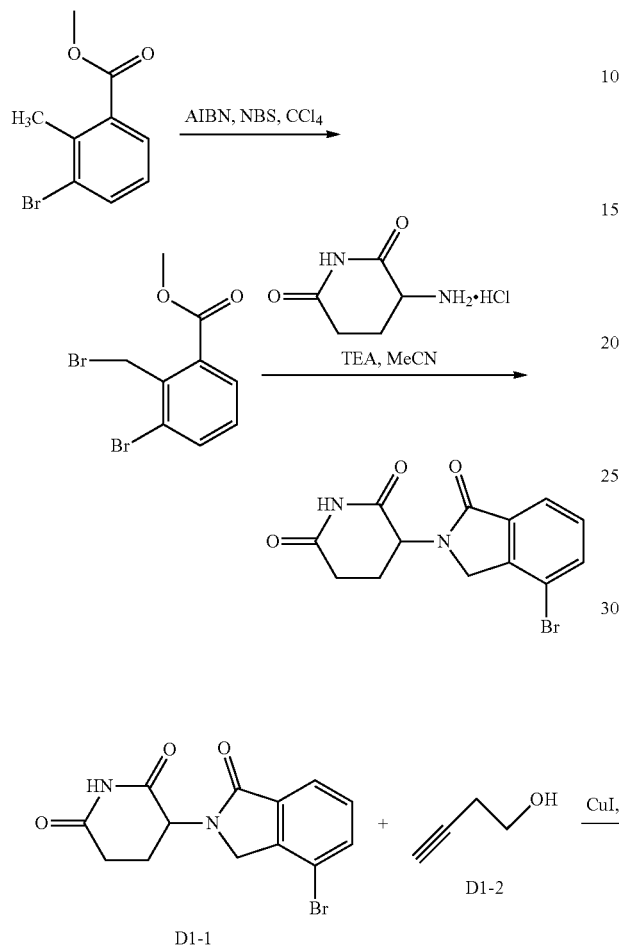

Methyl 3-bromo-2-methylbenzoate (1.14 g, 5.0 mmol) was dissolved in 20.0 mL of $CCl_4$. Under nitrogen protection, NBS (1.34 g, 7.5 mmol) and AIBN (164 mg, 1.0 mmol) were added. The temperature was raised to 85° C., and the reaction was refluxed for 20 h. TLC showed that there was no raw material remaining. The reaction solution was cooled to room temperature, and filtered with suction. The filtrate was concentrated under reduced pressure to give a crude product, which was purified by Flash to give 1.35 g of product as light-yellow oil. This oily compound (1.35 g, 4.41 mmol) and 3-aminopiperidine-2,6-dione hydrochloride (941 mg, 5.74 mmol) were dispersed in 25.0 mL of anhydrous MeCN, and TEA (580 mg, 5.74 mmol) was added. The temperature was raised to 80° C., and the reaction was refluxed for 16 h. The reaction was completed as detected by LCMS. The reaction solution was cooled to room temperature, and filtered with suction. The filter cake was rinsed three times with MeCN, and the solid was dried with baking to give compound D1-1 (1.31 g, yield: 92.3%), LCMS: $[M+H]^+=323, 325$.

Preparation of Target Compounds

Preparation of 3-(1-oxo-4-(4-(4-(((R,E)-1¹,2⁶,7-trimethyl-3-oxo-5²,5³-dihydro-1¹H,5¹H-11-oxa-4-aza-5(2,1)-benzo[d]imidazole-2(2,4)-pyridine-1(4,5)-pyrazolecyclododecan-5⁶-yl)methyl)piperazin-1-yl)butyl)isoindol-2-yl)piperidine-2,6-dione (D1)

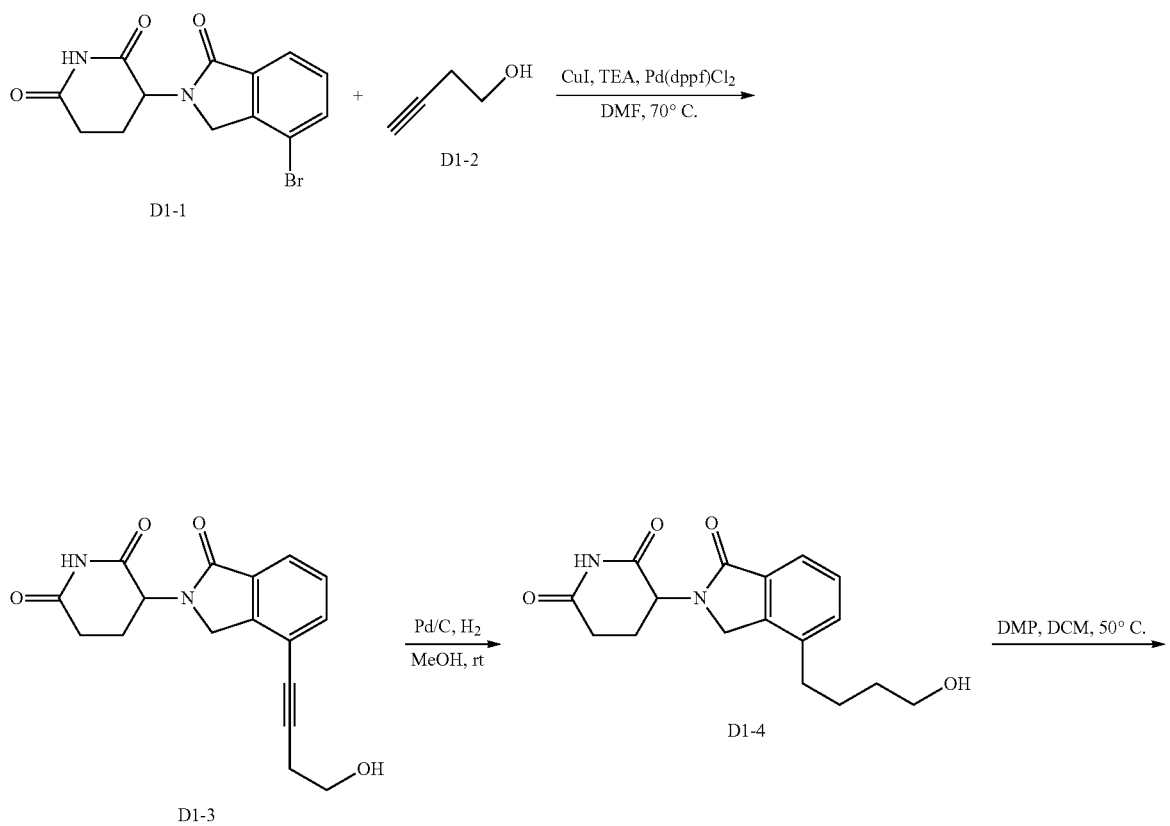

-continued

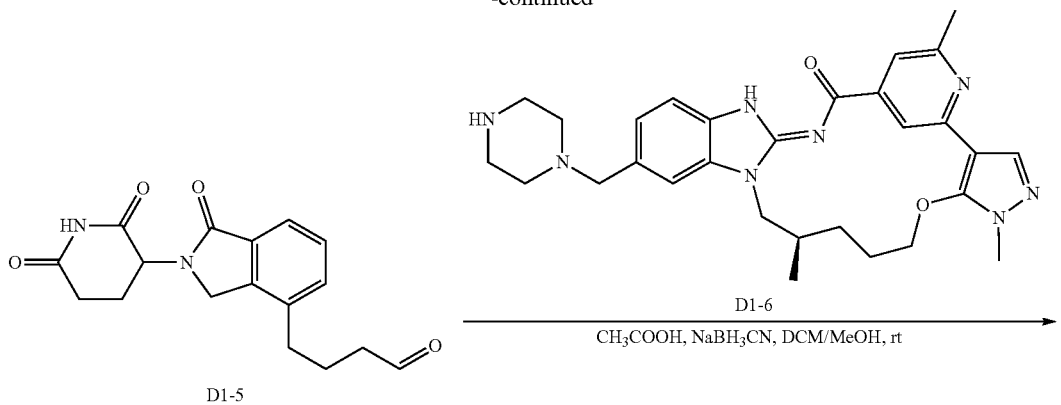

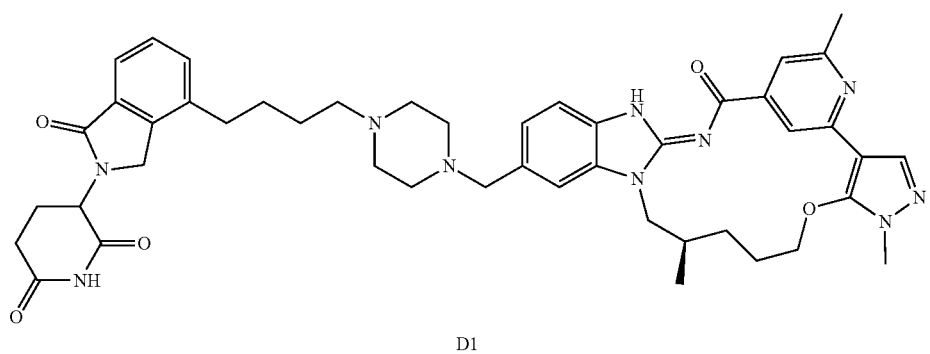

Step 1:

D1-1 (644 mg, 2.0 mmol), CuI (38 mg, 0.2 mmol) and Pd(dppf)Cl$_2$ (146.2 mg, 0.2 mmol) were dispersed in 20.0 mL of anhydrous DMF. Under the protection of N$_2$, D1-2 (280.4 mg, 4.0 mmol) and TEA (606 mg, 6.0 mmol) were sequentially added. The mixture was heated to 70° C. and reacted for 20 h. The reaction was completed as detected by LCMS. The reaction solution was cooled to room temperature, and purified by RP-Flash to give crude product D1-3 as pale-yellow solid (450 mg, yield: 72.1%), LCMS: [M+H]$^+$=313.

Step 2:

D1-3 (450 mg, 1.44 mmol) was dissolved in 90.0 mL of anhydrous MeOH, and 10% Pd/C (225 mg) was added to the mixture. H$_2$ (0.4 atm) was charged into the reaction solution, and the reaction was carried out at room temperature for 2 h. The reaction was completed as detected by LCMS.

The solid catalyst was removed by suction filtration of the reaction solution, and the solvent was removed from the filtrate under reduced pressure to give crude product D1-4 as a white solid (450 mg, yield: 98.9%). The crude product was directly used in the next reaction. LCMS: [M+H]$^+$=317.

Step 3:

D1-4 (420 mg, 1.33 mmol) was dissolved in 150 mL of anhydrous DCM. Under N$_2$ protection, Dess-Martin reagent (1010 mg, 2.39 mmol) was added. The temperature was raised to 50° C., and the reaction was refluxed for 2.0 h. The reaction was completed as detected by TLC. After the reaction solution was cooled to room temperature, 30 mL of saturated NaHCO$_3$ solution and 30 mL of saturated Na$_2$S$_2$O$_3$ solution were added to the reaction solution, and the mixture was stirred at room temperature for 5 min. The organic layer was separated, dried with anhydrous sodium sulfate, and filtered with suction. The filtrate was concentrated under reduced pressure to give crude product. The crude product was purified by Flash to give product D1-5 as a white solid (350 mg, yield: 83.3%). LCMS: [M+H]$^+$=315.

Step 4:

D1-5 (47.1 mg, 0.15 mmol) and D1-6 (63.4 mg, 0.12 mmol) were dissolved in a mixed solvent of 5.0 mL of anhydrous DCM and 0.5 mL of anhydrous MeOH, and CH$_3$COOH (13.5 mg, 0.225 mmol) was added under nitrogen protection. The mixture was stirred at room temperature for 0.5 h, and then solid NaBH$_3$CN (18.84 mg, 0.3 mmol) was added to the reaction solution. The mixture was reacted at room temperature for another 2 h. The reaction was completed as detected by LCMS and TLC. The reaction solution was purified by Prep-TLC to give a crude product, which was further purified by Prep-HPLC to give pure product D1 as a white solid (10.5 mg, yield: 10.61%). LCMS: [M+H]$^+$=827.

Preparation of 3-(1-oxo-4-(5-(4-(((R,E)-1¹,2⁶,7-trimethyl-3-oxo-5²,5³-dihydro-1¹H,5¹H-11-oxa-4-aza-5 (2,1)-benzo[d]imidazole-2 (2,4)-pyridine-1 (4,5)-pyrazolecyclododecan-5⁶-yl)methyl)piperazin-1-yl) pent-1-yn-1-yl)isoindol-2-yl)piperidine-2,6-dione (D2)

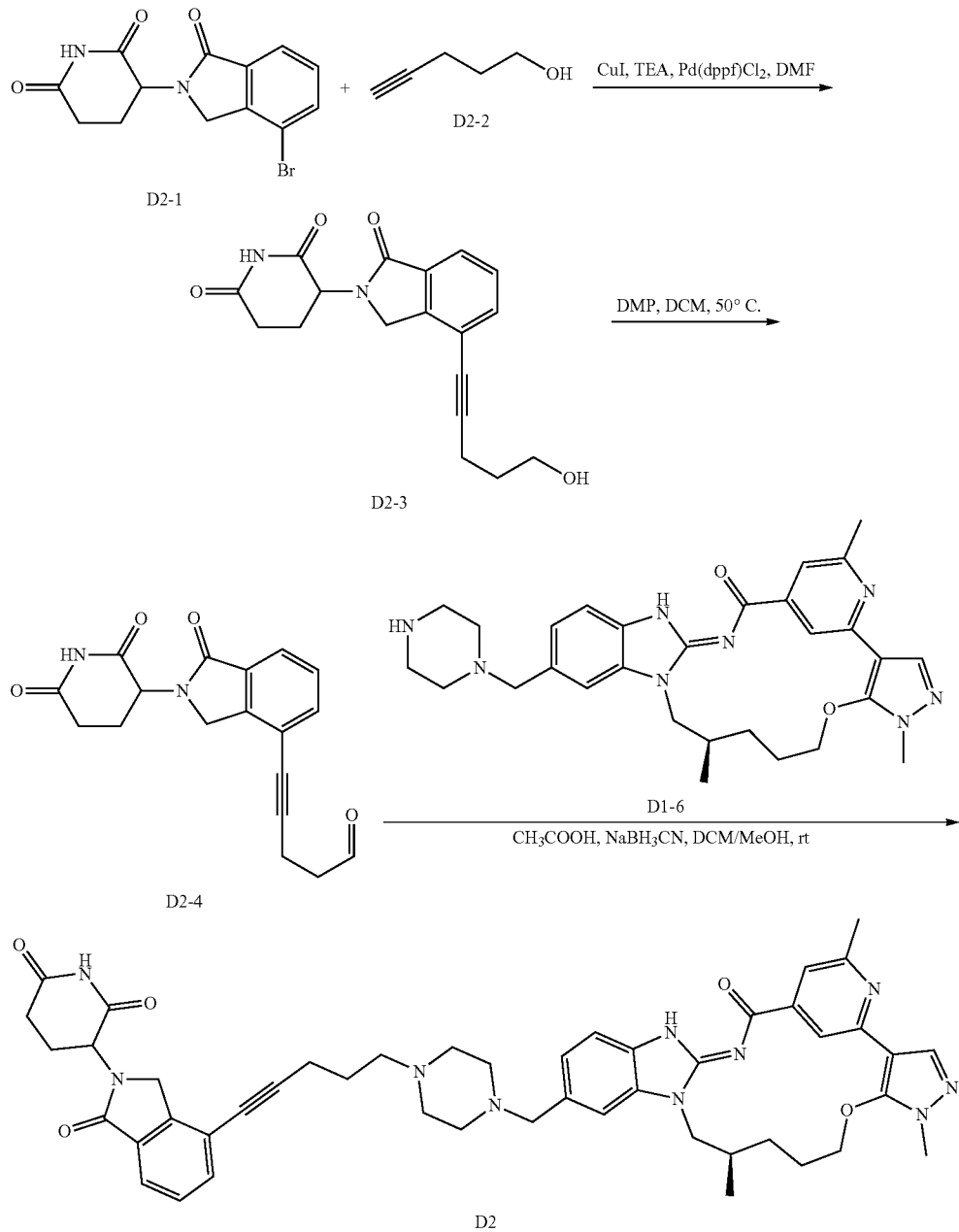

Step 1:

D2-1 (or D1-1)(322 mg, 1.0 mmol), CuI (19 mg, 0.1 mmol) and Pd(dppf)Cl₂ (73.1 mg, 0.1 mmol) were dispersed in 10.0 mL of anhydrous DMF. Under N₂ protection, pent-4-yn-1-ol (210 mg, 2.5 mmol) and TEA (303 mg, 3.0 mmol) were added in sequence. The mixture was heated to 70° C. and reacted for 20 h. The reaction was completed as detected by LCMS. The reaction solution was cooled to room temperature, and purified by RP-Flash to give crude product D2-3 as a white solid (410 mg, yield: 94.1%), LCMS: [M+H]⁺=327.

Step 2:

D2-3 (400 mg, 0.920 mmol) was dissolved in a mixed solvent of 150 mL of anhydrous DCM and 10 mL of anhydrous THF. Dess-Martin reagent (1.04 g, 2.454 mmol) was added under the protection of N₂. The temperature was raised to 50° C., and the reaction was refluxed for 2.0 h. The reaction was completed as detected by TLC. After the reaction solution was cooled to room temperature, 20 mL of saturated NaHCO$_3$ solution and 20 mL of saturated Na$_2$S$_2$O$_3$ solution were added to the reaction solution. The mixture was vigorously stirred at room temperature for 5 min. The organic layer was separated, dried with anhydrous sodium sulfate, and filtered with suction. The filtrate was concentrated under reduced pressure to give crude product. The crude product was purified by Flash to give product D2-4 as a light-yellow solid (280 mg, yield: 93.3%). LCMS: [M+H]$^+$=325.

Step 3:

D2-4 (48.6 mg, 0.15 mmol) and D1-6 (63.4 mg, 0.12 mmol) were dissolved in a mixed solvent of 50 mL of anhydrous DCM and 0.5 mL of anhydrous MeOH. Under nitrogen protection, CH$_3$COOH (13.5 mg, 0.225 mmol) was added, and the mixture was stirred at room temperature for 0.5 h. Solid NaBH$_3$CN (18.84 mg, 0.3 mmol) was then added to the reaction solution, and the mixture was reacted at room temperature for another 2 h. The reaction was completed as detected by LCMS and TLC. The reaction solution was purified by Prep-TLC to give a crude product, which was further purified by Prep-HPLC to give pure product D2 as a white solid (20 mg, yield: 20.0%). LCMS: [M+H]$^+$=837.

Preparation of 3-(1-oxo-4-(5-(4-(((R,E)-1$^1$,2$^6$,7-trimethyl-3-oxo-5$^2$,5$^3$-dihydro-1$^1$H,5$^1$H-11-oxa-4-aza-5 (2,1)-benzo[d]imidazole-2 (2,4)-pyridine-1 (4,5)-pyrazolecyclododecan-5$^6$-yl)methyl)piperazin-1-yl) pentyl)isoindol-2-yl)piperidine-2,6-dione (D3)

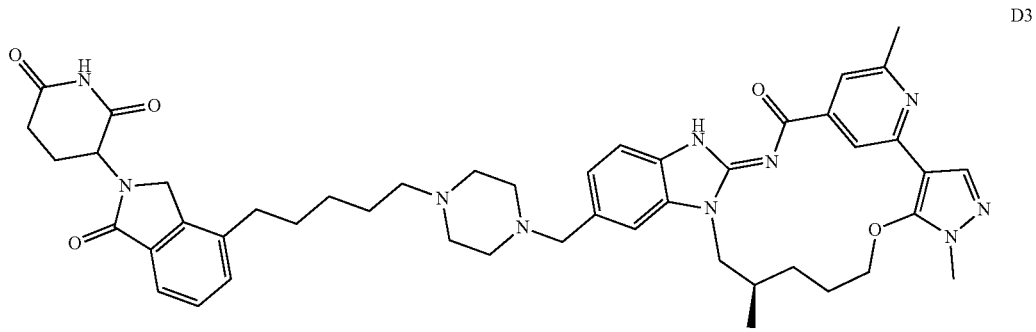 [SMILES: Cc1cc2cc(n1)-c1cnn(C)c1OCCC[C@@H](C)CN1/C(=N/C2=O)Nc2ccc(CN3CCN(CCCCCc4cccc5c4CN(C4CCC(=O)NC4=O)C5=O)CC3)cc21]

It was prepared by the same method as for the preparation of D1, using 3-(4-bromo-1-oxoisoindolin-2-yl)piperidine-2,6-dione (D1-1) and pent-4-yn-1-ol as raw materials, to give D3 as a white solid. LCMS: [M+H]$^+$=841.

Preparation of 3-(1-oxo-4-(6-(4-(((R,E)-1$^1$,2$^6$,7-trimethyl-3-oxo-5$^2$,5$^3$-dihydro-1$^1$H,5$^1$H-11-oxa-4-aza-5 (2,1)-benzo[d]imidazole-2 (2,4)-pyridine-1 (4,5)-pyrazolecyclododecan-5$^6$-yl)methyl)piperazin-1-yl) hexyl)isoindol-2-yl)piperidine-2,6-dione (D4)

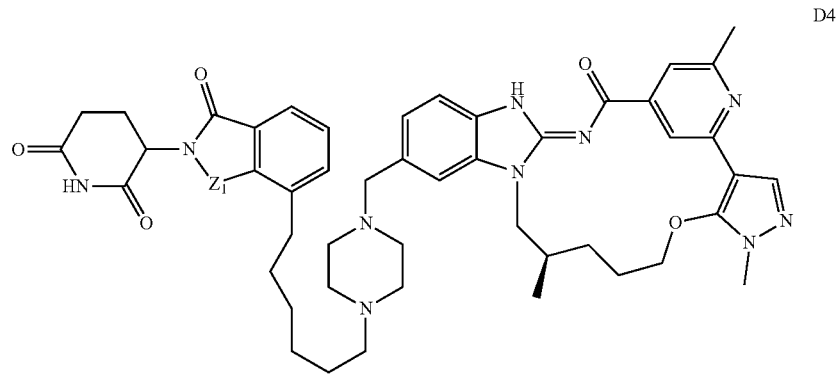

It was prepared by the same method as for the preparation of D1, using 3-(4-bromo-1-oxoisoindolin-2-yl)piperidine-2,6-dione (D1-1) and hex-5-yn-1-ol as raw materials, to give D4 as a white solid. LCMS: [M+H]$^+$=855.

Preparation of 3-(1-oxo-4-(7-(4-(((R,E)-1$^1$,2$^6$,7-trimethyl-3-oxo-5$^2$,5$^3$-dihydro-1$^1$H,5$^1$H-11-oxa-4-aza-5 (2,1)-benzo[d]imidazole-2 (2,4)-pyridine-1 (4,5)-pyrazolecyclododecan-5$^6$-yl)methyl)piperazin-1-yl) heptyl)isoindol-2-yl)piperidine-2,6-dione (D5)

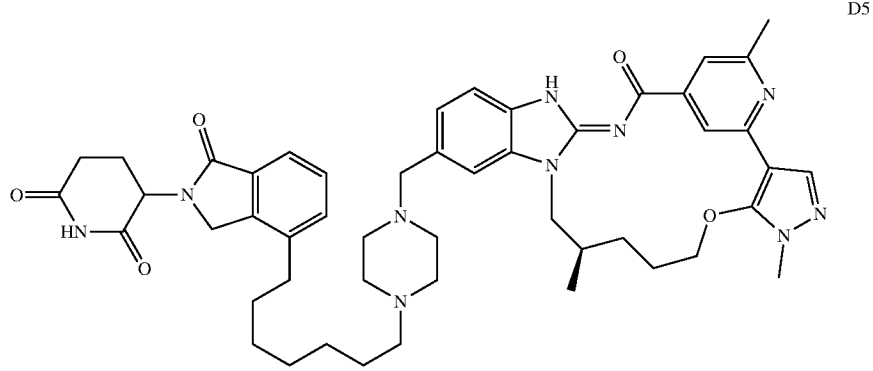 [SMILES: Cc1cc2cc(n1)-c1cnn(C)c1OCCC[C@@H](C)CN1/C(=N/C2=O)Nc2ccc(CN3CCN(CCCCCCCc4cccc5c4CN(C4CCC(=O)NC4=O)C5=O)CC3)cc21]

D5

It was prepared by the same method as for the preparation of D1, using 3-(4-bromo-1-oxoisoindolin-2-yl)piperidine-2,6-dione (D1-1) and hept-6-yn-1-ol as raw materials, to give D5 as a white solid. LCMS: [M+H]$^+$=869.

Assay of Inhibitory Activity on EGFR

1. Assay Method
   (1) A compound stock solution was prepared and diluted 3× to give a compound dilution; 10 nL of the compound dilution was transferred to a 384-well plate (784075, Greiner) by Echo 550;
   (2) The plate was sealed, and centrifuged at 1,000 g for 1 min;
   (3) 2×EGFR$^{L858R/T790M/C797S}$ protein working solutions were prepared with 1× kinase buffer, respectively;
   (4) 5 µl of the 2×EGFR protein working solution was added to the 384-well plate from step (2), centrifuged at 1,000 g for 30 s, and allowed to stand at room temperature (mixed thoroughly) for 10 min;
   (5) A mixture of 2× TK-substrate-biotin (2 µM) and ATP was prepared with 1× Kinase buffer;
   (6) 5 µL of the TK-substrate-biotin and ATP (the mixture prepared in step (5)) was added to the 384-well plate from step (4) to initiate the reaction;
   (7) The mixture was centrifuged at 1,000 g for 30 s; the plate was sealed, and allowed to stand (and reacted) at room temperature for 40 min;
   (8) 4×Sa-XL 665 and TK-antibody-Cryptate were prepared with detection buffer;
   (9) 5 µL of the Sa-XL 665 and 5 µL of the TK-antibody-Cryptate were added successively to the 384-well plate from step (7);
   (10) The mixture was centrifuged at 1,000 g for 30 s, and allowed to stand (react) at room temperature for 1 h;
   (11) Fluorescence values were read at 615 nm and 665 nm by enzyme labeling instrument (PerkinElmer, 74785).

2. Data Analysis

The ratio (665/615) of each well was calculated.

Formula of inhibition rate (%):

$$\text{Inhibition (\%)} = \left[1 - \frac{\text{Ratio}_{cmpd} - \overline{\text{Ratio}}_{positive}}{\overline{\text{Ratio}}_{vehicle} - \overline{\text{Ratio}}_{positive}}\right] \times 100$$

Ratio$_{cmpd}$: Ratio (665/615) value of assay compound.
$\overline{\text{Ratio}}_{positive}$: Average ratio (665/615) value of positive control drug (Brigatinib).
$\overline{\text{Ratio}}_{vehicle}$: Average ratio (665/615) value of negative control.

The nonlinear regression curve (dose response-variable slope) between the value of inhibition rate (%) and the logarithm of compound concentration was fitted with graphpad prism 8.0, the effect dose curve of compound was drawn, and IC$_{50}$ value was calculated.

3. Assay Result

IC$_{50}$ values of the inhibitory activity of the compounds of the present disclosure on mutant EGFR$^{L858R/T790M/C797S}$ are shown in the table below.

| Compound No. | IC$_{50}$ (nM) EGFR$^{L858R/T790M/C797S}$ |
|---|---|
| D1 | 4.529 |
| D2 | 3.838 |
| D3 | 1.088 |
| D4 | 10.09 |
| D5 | 35.91 |
| Osimertinib | >1000 |

Conclusion: the compounds of the present disclosure have strong inhibitory activity on mutant EGFR$^{L858R/T790M/C797S}$.

Assay of Activity on Ba/F3 (EGFR$^{L858R/T790M/C797S}$) and Ba/F3 (EGFR$^{Del19/T790M/C797S}$) Cells 1. Assay Method
   (1) Ba/F3 (EGFR$^{L858R/T790M/C797S}$) and Ba/F3 (EGFR$^{Del19/T790M/C797S}$) cells were respectively cultured according to the requirements of ATCC, incubated in an incubator at 37° C. and 5% CO$_2$, and analyzed by index; cells with viability of >90% can be used in the assay, and cells were seeded in a 384-well plate (PerkinElmer, 6007680) with 700 cells/well, 30 µL/well.
   (2) A compound stock solution was prepared, and then diluted 3× to give a compound dilution. 30 nL of the compound dilution was added to a 384-well plate by Echo (Labcyte, Echo550). The cells were incubated in an incubator at 37° C. and 5% $CO_2$ for 72 h.

(3) 30 μL of CTG was added to each well, and the 384-well plate was shaken on a Plate shaker (QILIN-BEIER, QB-9002). The 384-well plate was incubated at 37° C. and 5% $CO_2$ in the dark for 30 min, and the chemiluminescence value was read by Envision (PerkinElmer, En Vision 2104).

2. Data Analysis

The percent inhibition rate (% inhibition) was calculated by the following formula $$\text{Inhibition (\%)} = \left[1 - \frac{LUM_{cmpd} - \overline{LUM}_{positive}}{\overline{LUM}_{vehicle} - \overline{LUM}_{positive}}\right] \times 100$$

$LUM_{cmpd}$: Luminescence value of assay compound.
$\overline{LUM}_{positive}$: Average LUM value of positive drug (Brigatinib) with a concentration of 10 μM.
$\overline{LUM}_{vehicle}$: Average LUM value of negative control group without drug treatment.

The nonlinear regression curve (dose response-variable slope) between the value of inhibition rate (%) and the logarithm of compound concentration was fitted with graphpad prism 8.0, the effect dose curve of compound was drawn, and the $IC_{50}$ value was calculated.

$Y$=Bottom+($Top$−Bottom)/(1+10^(($LogIC_{50}$−$X$)*Hill-Slope))

X-axis: logarithm of compound concentration; Y axis: inhibition rate (% inhibition).

3. Assay Result $IC_{50}$ values of the inhibitory activity of the compounds of the present disclosure on Ba/F3 (EGFR$^{L858R/T790M/C797S}$) and Ba/F3 (EGFR$^{Del19/T790M/C797S}$) cells are shown in the table below.

| Compound No. | IC$_{50}$ (nM) Ba/F3 (EGFR$^{L858R/T790M/C797S}$) | Ba/F3 (EGFR$^{Del19/T790M/C797S}$) |
| --- | --- | --- |
| D1 | 2.119 | 2.697 |
| D2 | 3.958 | 3.889 |
| D3 | 2.877 | 3.126 |
| D4 | 4.390 | 4.405 |
| D5 | 11.57 | 10.70 |
| Osimertinib | >1000 | >1000 |

Conclusion: The compounds of the present disclosure have strong inhibitory activity on mutant Ba/F3 (EGFR$^{L858R/T790M/C797S}$) and Ba/F3 (EGFR$^{Del19/T790M/C797S}$) cells.

Assay of Activity of Compounds for Inducing EGFR$^{L858R/T790M/C797S}$ Protein Degradation In order to further explain the reason why the compounds of the present disclosure have inhibitory activity on Ba/F3 (EGFR$^{L858R/T790M/C797S}$) cells, representative compounds D3 was selected to study the mechanism of action of the compounds, and observe their effects on EGFR$^{L858R/T790M/C797S}$ protein levels.

(1) Cell Culture:
Ba/F3 (EGFR$^{L858R/T790M/C797S}$) cells were cultured according to the culture conditions recommended by ATCC, and analyzed by index.
Complete medium: 1640 medium, 10% FBS, 1× glutamine, 1× penicillin-streptomycin.
Culture conditions: incubated at 37° C., 95% air, 5% $CO_2$ incubator.

(2) Compound Stock Solution:
10 mM stock solution in DMSO, stored at −20° C.

(3) Preparation of Cell Suspension:
The cells in the cell culture bottle were collected, and the cells with viability of >90% can be used in the assay. Cells were seeded in a 96-well plate with 40 μL cells, 1*10$^5$ cells/well.

(4) Compound Treatment:
Compound was serially diluted 3× with DMSO, starting at 1.0 mM, into 10 concentrations to prepare working solutions.

(5) Compound was Pipetted into the 96-Well Plate to Treat Cells in a 37° C., 95% Air, 5% $CO_2$ Incubator for 6 h.

(6) Detection:
1) 1 μg/mL of EGF activated cells were treated for 10 min;
2) After the compound treatment, lysis buffer was added to lyse cells; 10 μL of cell lysate was transferred to a 384-well plate; in addition, 5 μL of acceptor mix was added to the 384-well plate, and shaken on a shaker for 1-2 min;
3) 5 μL of donor mix was added to each well; the 384-well plate was sealed, shaken on a shaker for 1-2 min, left in the dark at room temperature overnight, and read with an enzyme labeling instrument.

(7) Data Analysis:
Alpha counts were fitted by logarithmic treatment of compound concentration with Graphpad Prism 8.0.

$Y$=Bottom+($Top$−Bottom)/(1+10^(($LogIC_{50}$−$X$)*Hill-Slope))

X: logarithm of compound concentration; Y: Alpha Counts.

(8) Assay Result:
The effects of the compounds of the present disclosure on mutant EGFR$^{L858R/T790M/C797S}$ protein level are shown in FIG. 1.

As shown in FIG. 1, the assay results show that in the range of 0.01 nM to 1000 nM, EGFR$^{L858R/T790M/C797S}$ protein level decreases with the increase of the concentration of compound D3, and compound D3 significantly reduces EGFR$^{L858R/T790M/C797S}$ protein level with a DC$_{50}$ of 9.28 nM, which proves that the compounds of the present disclosure have significant degradation effect on EGFR$^{L858R/T790M/C797S}$ protein in a dose-dependent manner.

Conclusion: the compound of the present disclosure can significantly induce the degradation of EGFR$^{L858R/T790M/C797S}$ protein in cells in a dose-dependent manner.

The above is a further detailed description of the present disclosure in connection with the specific alternative embodiments, and the specific embodiments of the present disclosure are not limited to the description. It will be apparent to those skilled in the art that the present disclosure may be practiced by making various simple deduction and replacement, without departing from the spirit and scope of the invention.

What is claimed is:

1. A compound of general formula (I), or a pharmaceutically acceptable salt, enantiomer, diastereomer, racemate, solvate, hydrate, polymorph, prodrug, or isotopic variant thereof, or a mixture thereof:

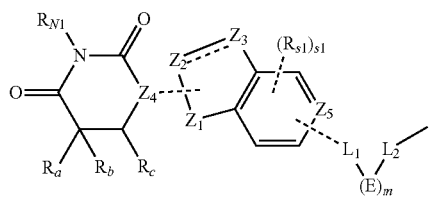 (I)

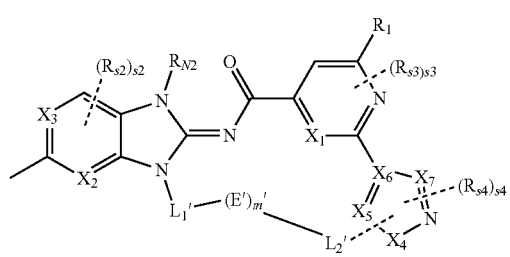

wherein
═ represents single bond or double bond;
----- represents that the point of attachment to the rest of the molecule can be located at an available point of a ring;
$Z_1$ is O, S, N or C atom, which is optionally substituted with one or two $R_{Z1}$;
$Z_2$ is O, S, N or C atom, which is optionally substituted with one or two $R_{Z2}$;
$Z_3$ is O, S, N or C atom, which is optionally substituted with one or two $R_{Z3}$; with the proviso that when ═ represents double bond, $Z_2$ is N or C atom, and $Z_3$ is N or C atom;
$Z_4$ is N or $CR_{Z4}$;
$Z_5$ is N or $CR_{Z5}$;
$R_a$, $R_b$ and $R_c$ are independently H, halogen, $C_{1-6}$ alkyl or $C_{1-6}$ haloalkyl;
$R_{N1}$ is H, $C_{1-6}$ alkyl or $C_{1-6}$ haloalkyl;
$R_{Z1}$ is absent, H, CN, halogen, $C_{1-6}$ alkyl, or $C_{1-6}$ haloalkyl; or two $R_{Z1}$ are taken together with $Z_1$ to form C═O;
$R_{Z2}$ is absent, H, CN, halogen, $C_{1-6}$ alkyl, or $C_{1-6}$ haloalkyl;
$R_{Z3}$ is absent, H, CN, halogen, $C_{1-6}$ alkyl, or $C_{1-6}$ haloalkyl; or two $R_{Z3}$ are taken together with $Z_3$ to form C═O;
$R_{Z4}$ is H, CN, halogen, $C_{1-6}$ alkyl, or $C_{1-6}$ haloalkyl;
$R_{Z5}$ is H, CN, halogen, $C_{1-6}$ alkyl, or $C_{1-6}$ haloalkyl;
$L_1$ is selected from bond, —O—, —S(O)$_p$—, —NR$^\#$—, —CR$^\#$R$^{\#'}$— or —C$_a$R$^\#$R$^{\#'}$—C$_b$R$^\#$R$^{\#'}$—;
$L_2$ is selected from bond, —O—, —S(O)$_p$—, —NR$^\#$—, —CR$^\#$R$^{190}$'— or —C$_a$R$^\#$R$^{\#'}$—C$_b$R$^\#$R$^{\#'}$—;
wherein any one of C$_a$R$^\#$R$^{\#'}$ or C$_b$R$^\#$R$^{\#'}$ can be replaced by O, S(O)$_p$ or NR$^\#$, and when any one of C$_a$R$^\#$R$^{\#'}$ or C$_b$R$^\#$R$^{\#'}$ is replaced by O, S or NR$^\#$, the other of C$_a$R$^\#$R$^{\#'}$ or C$_b$R$^\#$R$^{\#'}$ can further be replaced by S(O)$_q$;

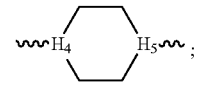

E is independently selected from: —C$_c$R$^\#$R$^{\#'}$—C$_d$R$^\#$R$^{\#'}$—C$_e$R$^\#$R$^{\#'}$ or
wherein any one of C$_c$R$^\#$R$^{\#'}$, C$_d$R$^\#$R$^{\#'}$ or C$_e$R$^\#$R$^{\#'}$, or both of C$_c$R$^\#$R$^{\#'}$ and C$_e$R$^\#$R$^{\#'}$ can be replaced by O, S(O)$_p$ or NR$^\#$, and when any one of C$_c$R$^\#$R$^{\#'}$, C$_d$R$^\#$R$^{\#'}$ or C$_e$R$^\#$R$^\#$ is replaced by O, S or NR$^\#$, the other one or two of C$_c$R$^\#$R$^{\#'}$, C$_d$R$^\#$R$^{\#'}$ or C$_e$R$^\#$R$^{\#'}$ adjacent to it can further be replaced by S(O)$_q$;
$H_4$ and $H_5$ are N or C atom;
p is 0, 1 or 2;
q is 1 or 2;
R$^\#$ is H, halogen, $C_{1-6}$ alkyl, $C_{1-6}$ haloalkyl, $C_{2-6}$ alkenyl or $C_{2-6}$ alkynyl;
R$^{\#'}$ is H, halogen, $C_{1-6}$ alkyl, $C_{1-6}$ haloalkyl, $C_{2-6}$ alkenyl or $C_{2-6}$ alkynyl;
or, R$^\#$ and R$^\#$ on adjacent atoms can be taken together to form bond, and R$^{\#'}$ and R$^{\#'}$ on adjacent atoms can be taken together to form bond;
or, R$^\#$ and R$^{\#'}$ on the same or different atoms can be taken together to form —O;
m is 0, 1, 2, 3, 4, 5, 6, 7, 8, 9 or 10;
$X_1$ is C or N atom;
$X_2$ is C or N atom;
$X_3$ is C or N atom;
$X_4$ is O, S, C or N atom, which is optionally substituted with one or two $R_2$;
$X_5$ is O, S, C or N atom;
$X_6$ is C or N atom;
$X_7$ is O, S, C or N atom;
$R_1$ is H, CN, halogen, $C_{1-6}$ alkyl, $C_{1-6}$ haloalkyl, $C_{2-6}$ alkenyl or $C_{2-6}$ alkynyl;
$R_2$ is H, CN, halogen, $C_{1-6}$ alkyl, $C_{1-6}$ haloalkyl, $C_{2-6}$ alkenyl or $C_{2-6}$ alkynyl;
$R_{N2}$ is H, $C_{1-6}$ alkyl or $C_{1-6}$ haloalkyl;
the definition of $L_1$' is the same as that of $L_1$;
the definition of $L_2$' is the same as that of $L_2$;
the definition of E' is the same as that of E;
the definition of m' is the same as that of m;
$R_{s1}$ is selected from H, CN, halogen, $C_{1-6}$ alkyl or $C_{1-6}$ haloalkyl;
$R_{s2}$ is selected from H, CN, halogen, $C_{1-6}$ alkyl, $C_{1-6}$ haloalkyl, $C_{2-6}$ alkenyl or $C_{2-6}$ alkynyl;
$R_{s3}$ is selected from H, CN, halogen, $C_{1-6}$ alkyl or $C_{1-6}$ haloalkyl;
$R_{s4}$ is selected from H, CN, halogen, $C_{1-6}$ alkyl, $C_{1-6}$ haloalkyl, $C_{2-6}$ alkenyl or $C_{2-6}$ alkynyl;
s1 is 0, 1, 2 or 3;
s2 is 0, 1, 2 or 3;
s3 is 0, 1 or 2;
s4 is 0, 1, 2, 3, 4 or 5.

2. The compound, or the pharmaceutically acceptable salt, enantiomer, diastereomer, racemate, solvate, hydrate, polymorph, prodrug, or isotopic variant thereof, or the mixture thereof according to claim 1, wherein $Z_4$ and $Z_2$ are connected to form a compound of formula (II) below:

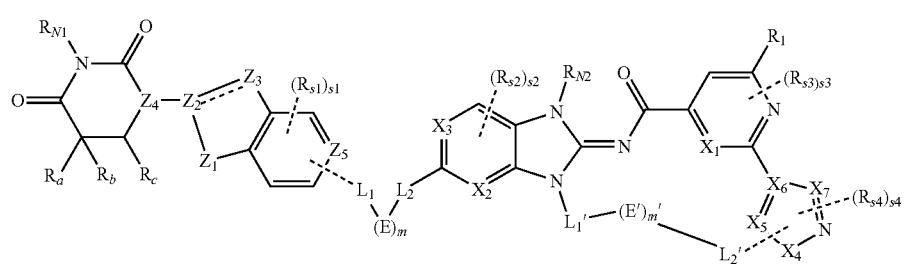

(II)

wherein all the groups are as defined in claim 1;
alternatively,

═ represents single bond or double bond;
----- represents that the point of attachment to the rest of the molecule can be located at an available point of a ring;

$Z_1$ is N or C atom, which is optionally substituted with one or two $R_{Z1}$;

$Z_2$ is N or C atom, which is optionally substituted with $R_{Z2}$;

$Z_3$ is N or C atom, which is optionally substituted with one or two $R_{Z3}$;

and other groups are as defined in claim 1.

3. The compound, or the pharmaceutically acceptable salt, enantiomer, diastereomer, racemate, solvate, hydrate, polymorph, prodrug, or isotopic variant thereof, or the mixture thereof according to claim 1, which is a compound of general formula (VI) or (VI') below:

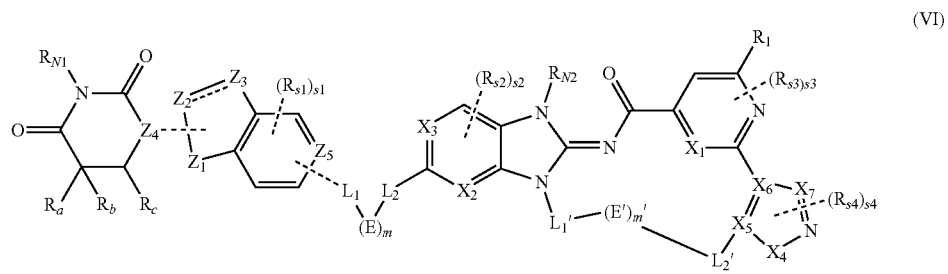

(VI)

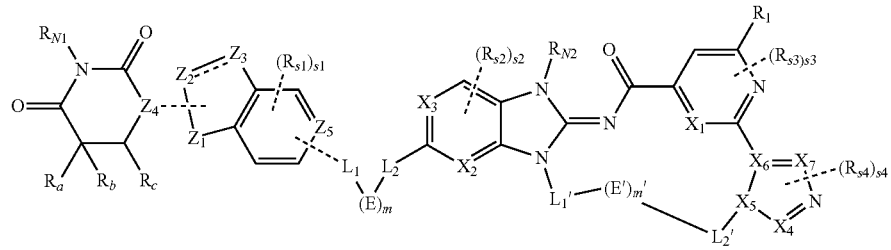

(VI')

wherein all the groups are as defined in claim 1.

4. The compound, or the pharmaceutically acceptable salt, enantiomer, diastereomer, racemate, solvate, hydrate, polymorph, prodrug, or isotopic variant thereof, or the mixture thereof according to claim 1,
wherein
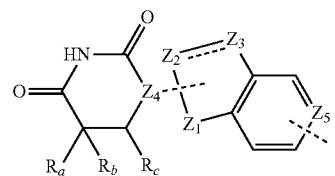
is selected from:
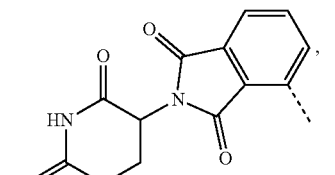
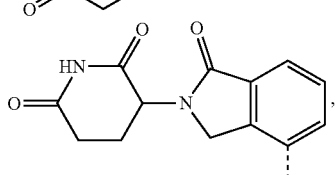
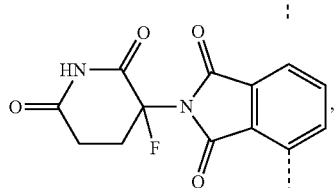
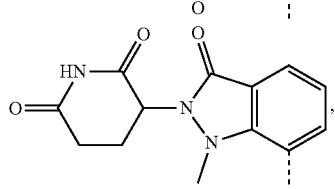
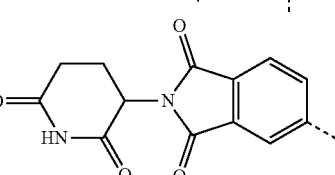
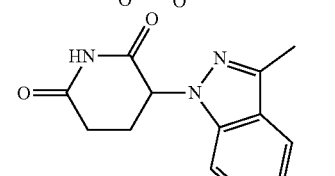
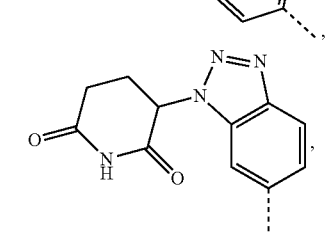
-continued
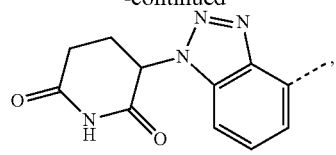
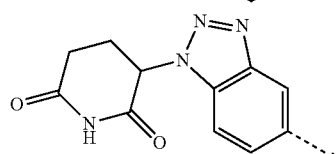
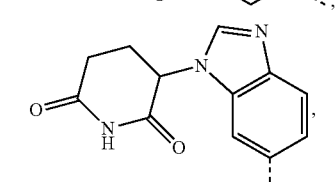
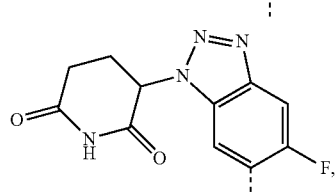
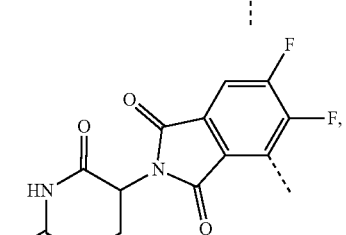
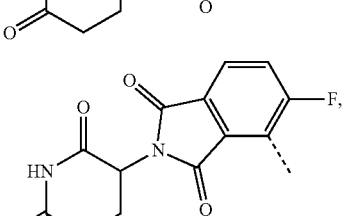
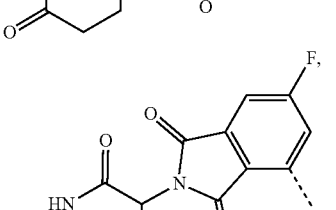
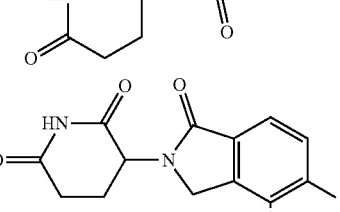
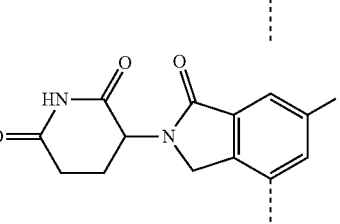

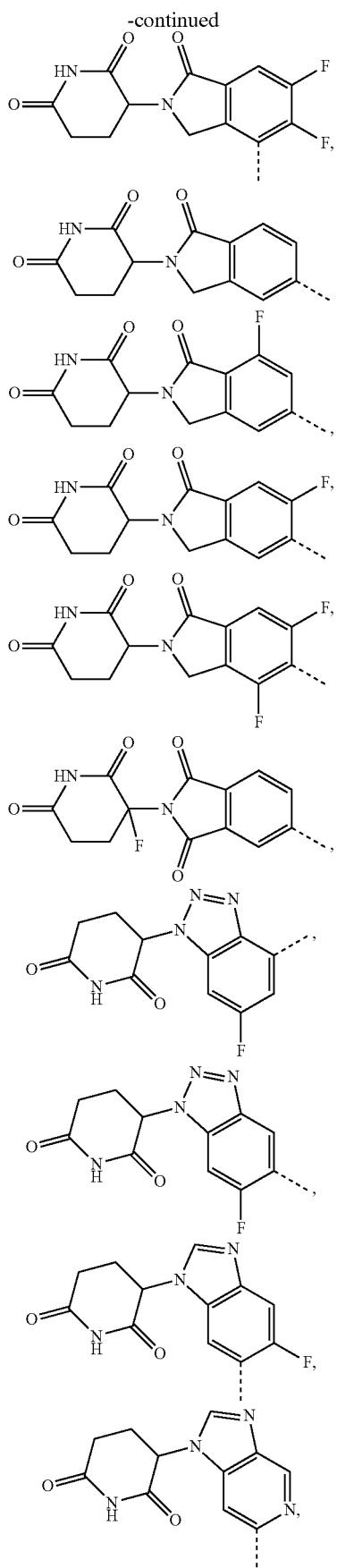

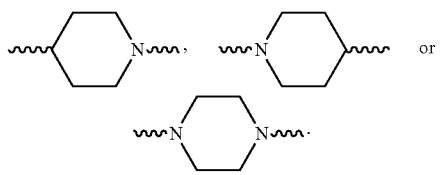

5. The compound, or the pharmaceutically acceptable salt, enantiomer, diastereomer, racemate, solvate, hydrate, polymorph, prodrug, or isotopic variant thereof, or the mixture thereof according to claim 1,
wherein $L_1$, $L_2$, $L_1'$ and $L_2'$ are each independently selected from bond, —O—, —S—, —S(O)—, —S(O)$_2$—, —NH—, —N(Me)-, —N(CF$_3$)—, —CH$_2$—, —CH(Cl)—, —CH(F)—, —CF$_2$—, —CH(CF$_3$)—, —C(O)—, —CH$_2$CH$_2$—, —CH=CH—, —C≡C—, —OCH$_2$—, —CH$_2$O—, —SCH$_2$—, —CH$_2$S—, —S(O)CH$_2$—, —CH$_2$S(O)—, —S(O)$_2$CH$_2$—, —CH$_2$S(O)$_2$—, —NHCH$_2$—, —N(Me) CH$_2$—, —CH$_2$NH—, —CH$_2$N(Me)-, —C(O)CH$_2$—, —CH$_2$C(O)—, —C(O)CMe$_2$-, —CMe$_2$C(O)—, —OC(O)—, —C(O)O—, —SC(O)—, —C(O)S—, —NHC(O)—, —N (Me) C(O)—, —C(O)NH— or —C(O)N(Me)-.

6. The compound, or the pharmaceutically acceptable salt, enantiomer, diastereomer, racemate, solvate, hydrate, polymorph, prodrug, or isotopic variant thereof, or the mixture thereof according to claim 1,
wherein E and E' are independently selected from bond, —CH$_2$CH$_2$CH$_2$—, —CH$_2$CH=CH—, —CH=CHCH$_2$—, —CH$_2$C≡C—, —C≡CCH$_2$—, —CH$_2$CH$_2$C(O)—, —CH$_2$C(O)CH$_2$—, —C(O)CH$_2$CH$_2$—, —CH$_2$CH$_2$S(O)$_2$—, —CH$_2$S(O)$_2$CH$_2$—, —S(O)$_2$CH$_2$CH$_2$—, —C(O)CH=CH—, —C(O)C≡C—, —CH$_2$CH$_2$O—, —CH$_2$OCH$_2$—, —OCH$_2$CH$_2$—, —CH$_2$CH$_2$S—, —CH$_2$SCH$_2$—, —SCH$_2$CH$_2$—, —C(O)CH$_2$O—, —OCH$_2$C(O)—, —CH$_2$C(O)O—, —C(O)CH$_2$S—, —SCH$_2$C(O)—, —CH$_2$C(O)S—, —OC(O)CH$_2$—, —C(O) OCH$_2$—, —CH$_2$OC(O)—, —SC(O)CH$_2$—, —C(O) SCH$_2$—, —CH$_2$SC(O)—, —CH$_2$CH$_2$NH—, —CH$_2$NHCH$_2$—, —NHCH$_2$CH$_2$—, —CH$_2$CH$_2$NMe-, —CH$_2$NMeCH$_2$—, —NMeCH$_2$CH$_2$—, —C(O)CH$_2$NH—, —NHCH$_2$C(O)—, —CH$_2$C(O)NH—, —NHC(O)CH$_2$—, —C(O)NHCH$_2$—, —CH$_2$NHC(O)—, 7. The compound, or the pharmaceutically acceptable salt, enantiomer, diastereomer, racemate, solvate, hydrate, polymorph, prodrug, or isotopic variant thereof, or the mixture thereof according to claim 1, wherein the ring where $X_4$, $X_5$, $X_6$ and $X_7$ are located is

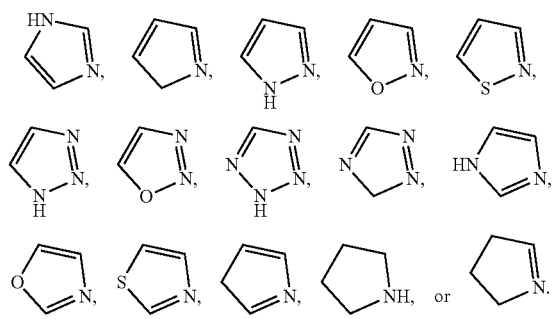

8. The compound, or the pharmaceutically acceptable salt, enantiomer, diastereomer, racemate, solvate, hydrate, polymorph, prodrug, or isotopic variant thereof, or the mixture thereof according to claim 1, wherein

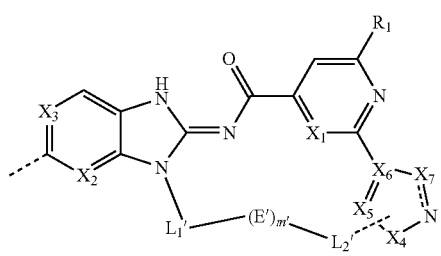

is selected from:

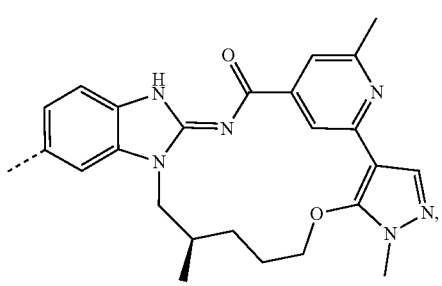

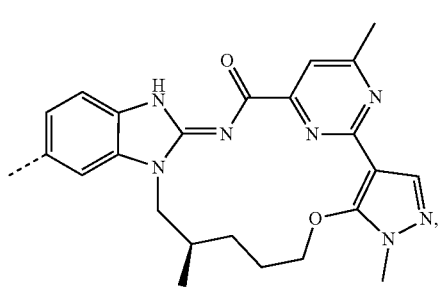

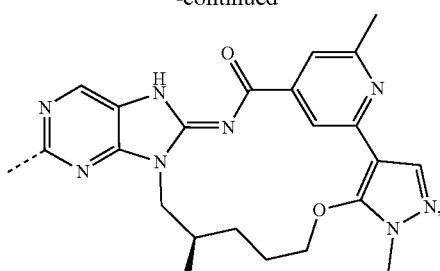

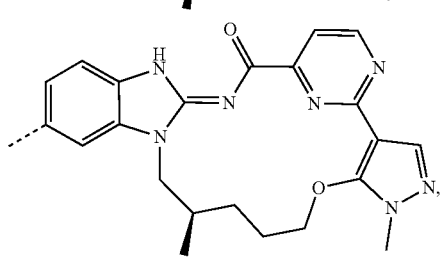

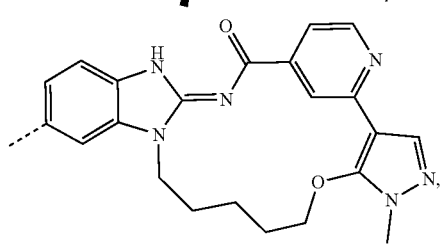

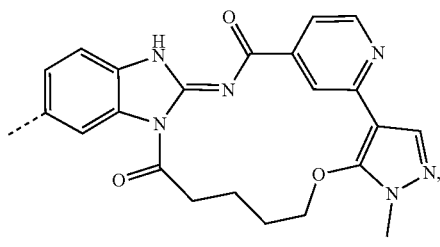

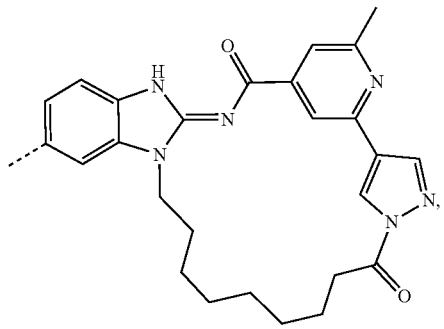

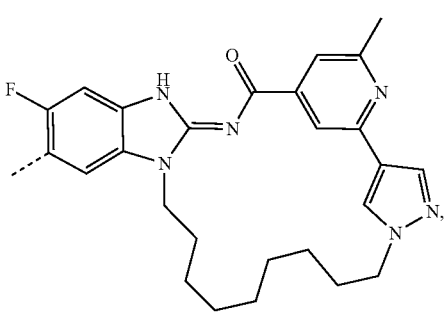

105
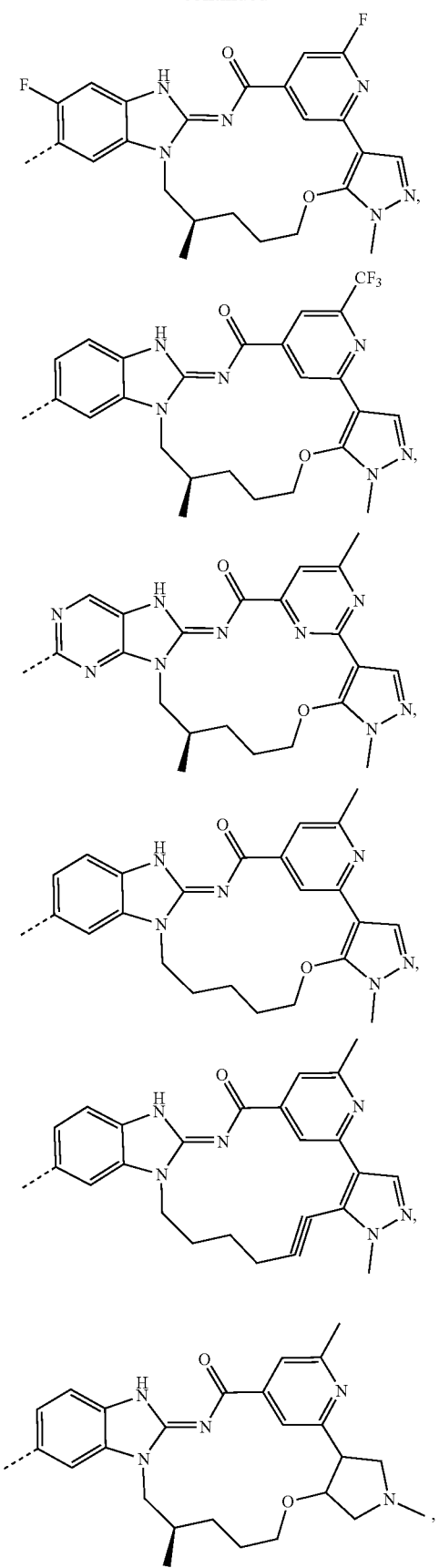
106
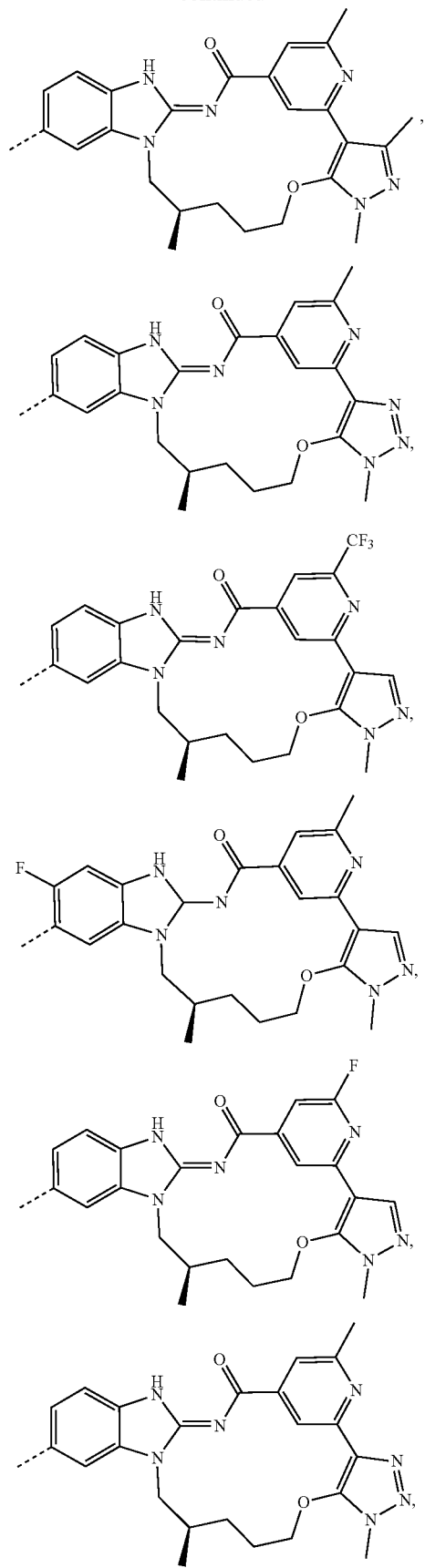

-continued

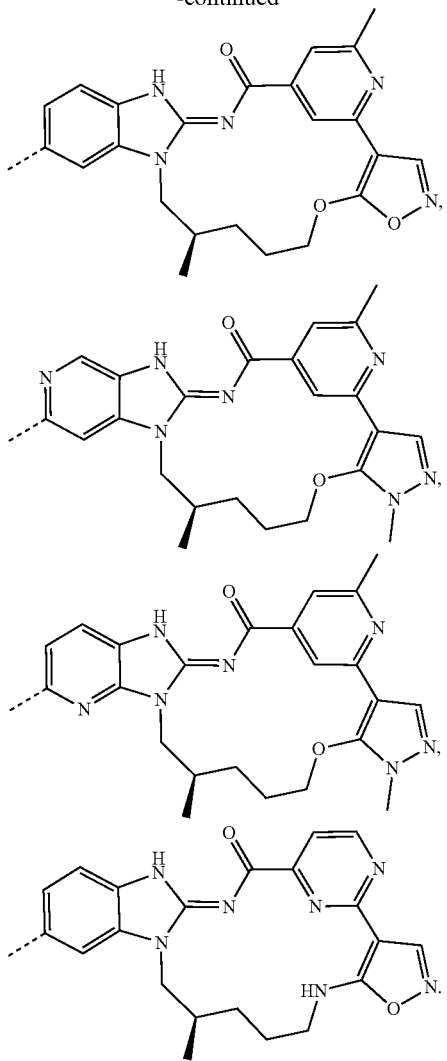

9. The compound, or the pharmaceutically acceptable salt, enantiomer, diastereomer, racemate, solvate, hydrate, polymorph, prodrug, or isotopic variant thereof, or the mixture thereof according to claim 1, which is a compound of general formula (VIII) below:

wherein
$Z_1$ is O, S, N or C atom, which is optionally substituted with one or two $R_{Z1}$;
  wherein $R_{Z1}$ is H, CN, halogen, $C_{1-6}$ alkyl, or $C_{1-6}$ haloalkyl; or two $R_{Z1}$ are taken together with $Z_1$ to form C—O;
$L_1$ is selected from bond, —O—, —NR$^{\#}$—, —CR$^{\#}$R$^{190\ '}$— or —$C_aR^{\#}R^{\#'}C_bR^{\#}R^{\#'}$—;
$L_3$ is selected from bond, —O—, —NR$^{\#}$—, —CR$^{\#}R^{\#'}$— or —$C_aR^{\#}R^{\#'}C_bR^{\#}R^{\#'}$—;
  wherein any one of $C_aR^{\#}R^{\#'}$ or $C_bR^{\#}R^{\#'}$ can be replaced by O, S(O)$_p$ or NR$^{\#}$, and when any one of $C_aR^{\#}R^{\#'}$ or $C_bR^{\#}R^{\#'}$ is replaced by O, S or NR$^{\#}$, the other of $C_aR^{\#}R^{\#'}$ or $C_bR^{\#}R^{\#'}$ can further be replaced by S(O)$_q$;
E is independently —$C_cR^{\#}R^{\#'}$—$C_dR^{\#}R^{\#'}$—$C_eR^{\#}R^{\#'}$;
  wherein any one of $C_cR^{\#}R^{\#'}$, $C_dR^{\#}R^{\#'}$ or $C_eR^{\#}R^{\#'}$, or both of $C_cR^{\#}R^{\#'}$ and $C_eR^{\#}R^{\#'}$ can be replaced by O, S(O)$_p$ or NR$^{\#}$, and when any one of $C_cR^{\#}R^{\#'}$, $C_dR^{\#}R^{\#'}$ or $C_eR^{\#}R^{\#'}$ is replaced by O, S or NR$^{\#}$, the other one or two of $C_cR^{\#}R^{\#'}$, $C_dR^{\#}R^{\#'}$ or $C_eR^{\#}R^{\#'}$ adjacent to it can further be replaced by S(O)$_q$;
p is 0, 1 or 2;
q is 1 or 2;
R$^{\#}$ is H, halogen, $C_{1-6}$ alkyl, $C_{1-6}$ haloalkyl, $C_{2-6}$ alkenyl or $C_{2-6}$ alkynyl;
R$^{\#'}$ is H, halogen, $C_{1-6}$ alkyl, $C_{1-6}$ haloalkyl, $C_{2-6}$ alkenyl or $C_{2-6}$ alkynyl;
  or, R$^{\#}$ and R$^{\#}$ on adjacent atoms can be taken together to form bond, and
R$^{\#'}$ and R$^{\#'}$ on adjacent atoms can be taken together to form bond;
  or, R$^{\#}$ and R$^{\#'}$ on the same atom can be taken together to form —O;
m is 1, 2 or 3.

10. The compound of general formula (VIII), or the pharmaceutically acceptable salt, enantiomer, diastereomer, racemate, solvate, hydrate, polymorph, prodrug, or isotopic variant thereof, or the mixture thereof according to claim 9, wherein
$Z_1$ is —CH$_2$— or —C(O)—;
$L_1$ is selected from bond, —O—, —NH—, —CH$_2$—, —CH$_2$CH$_2$—, —CH=CH— or —C≡C—;
E is independently —CH$_2$CH$_2$CH$_2$—, —CH$_2$CH=CH—, —CH=CHCH$_2$—, —CH$_2$C≡C—, —C≡CCH$_2$—, —CH$_2$CH$_2$O—, —CH$_2$OCH$_2$—, —OCH$_2$CH$_2$—, —CH$_2$CH$_2$NH—, —CH$_2$NHCH$_2$—,

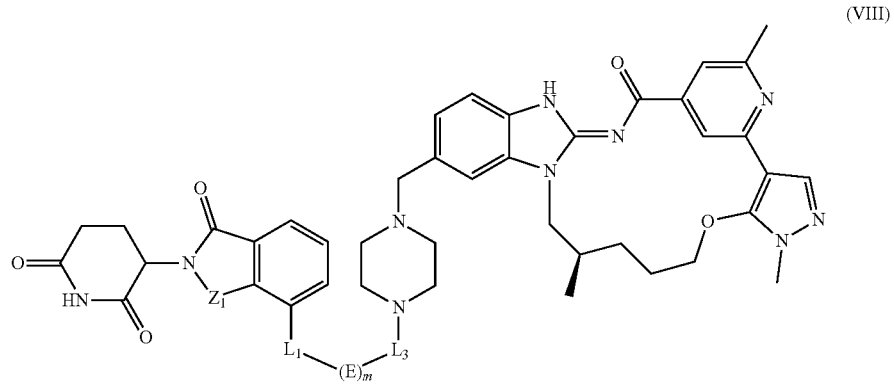

(VIII)

—NHCH$_2$CH$_2$—, —CH$_2$CH$_2$C(O)—, —CH$_2$C(O)CH$_2$—, —C(O)CH$_2$CH$_2$—, —CH$_2$OC(O)—, —CH$_2$C(O)O—, —OC(O)CH$_2$—, —C(O)OCH$_2$—, —CH$_2$NHC(O)—, —CH$_2$C(O)NH—, —NHC(O)CH$_2$—, —C(O)NHCH$_2$—, —OCH$_2$C(O)—, —C(O)CH$_2$O—, —NHCH$_2$C(O)— or —C(O)CH$_2$NH—;

L$_3$ is selected from bond, —O—, —NH—, —CH$_2$—, —C(O)—, —CH$_2$CH$_2$—, —C(O)CH$_2$— or —CH$_2$C(O)—;

m is 1, 2 or 3.

11. The compound of general formula (VIII), or the pharmaceutically acceptable salt, enantiomer, diastereomer, racemate, solvate, hydrate, polymorph, prodrug, or isotopic variant thereof, or the mixture thereof according to claim 9, wherein Z$_1$ is —CH$_2$— or —C(O)—;
L$_1$ is selected from bond, —O—, —NH—, —CH$_2$—, —CH$_2$CH$_2$—, —CH═CH— or —C≡C—;
E is independently —CH$_2$CH$_2$CH$_2$—, —CH$_2$CH═CH—, —CH═CHCH$_2$—, —CH$_2$C═C— or —C≡CCH$_2$—;
L$_3$ is selected from bond, —O—, —NH—, —CH$_2$— or —C(O)—;
m is 1, 2 or 3.

12. The compound of general formula (VIII), or the pharmaceutically acceptable salt, enantiomer, diastereomer, racemate, solvate, hydrate, polymorph, prodrug, or isotopic variant thereof, or the mixture thereof according to claim 9, wherein Z$_1$ is —CH$_2$— or —C(O)—;
L$_1$ is selected from bond, —O—, —NH—, —CH$_2$—, —CH$_2$CH$_2$— or —C≡C—;
E is independently —CH$_2$CH$_2$CH$_2$—;
L$_3$ is selected from bond, —CH$_2$— or —C(O)—;
m is 1 or 2.

13. The compound of general formula (VIII), or the pharmaceutically acceptable salt, enantiomer, diastereomer, racemate, solvate, hydrate, polymorph, prodrug, or isotopic variant thereof, or the mixture thereof according to claim 9, wherein Z$_1$ is —CH$_2$—;
L$_1$ is selected from bond, —CH$_2$—, —CH$_2$CH$_2$— or —C≡C—;
E is independently —CH$_2$CH$_2$CH$_2$—;
L$_3$ is selected from bond or —CH$_2$—;
m is 1 or 2.

14. The compound, or the pharmaceutically acceptable salt, enantiomer, diastereomer, racemate, solvate, hydrate, polymorph, prodrug, or isotopic variant thereof, or the mixture thereof according to claim 1, which is a compound of general formula (VIII) below:

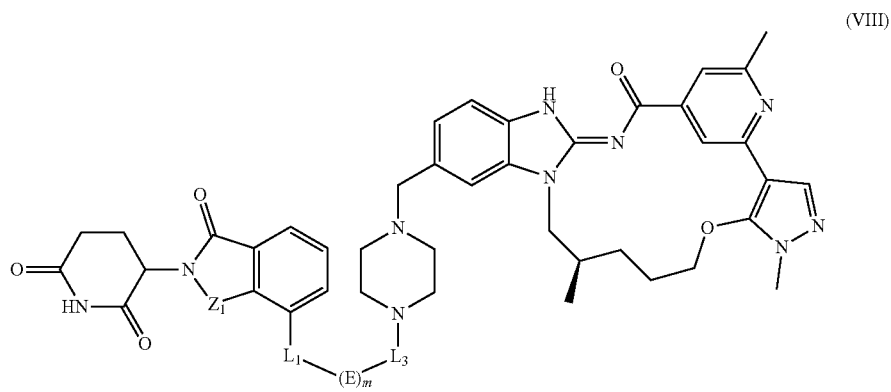

(VIII)

wherein
Z$_1$ is O, S, N or C atom, which is optionally substituted with one or two R$_{Z1}$;
R$_{Z1}$ is H, CN, halogen, C$_{1-6}$ alkyl, or C$_{1-6}$ haloalkyl; or two R$_{Z1}$ are taken together with Z$_1$ to form C—O;
L$_1$ is selected from bond, —O—, —NR$^\#$—, —CR$^\#$R$^{\#'}$— or —C$_a$R$^\#$R$^{\#'}$C$_b$R$^\#$R$^{\#'}$—;
L$_3$ is selected from bond, —O—, —NR$^\#$—, —CR"R"— or —C$_a$R$^\#$R$^{\#'}$C$_b$R$^\#$R$^{\#'}$—;
E is —C$_c$R$^\#$R$^{\#'}$—C$_d$R$^\#$R$^{\#'}$—C$_e$R$^\#$R$^{\#'}$;
wherein any one of C$_c$R$^\#$R$^{\#'}$ or C$_e$R$^\#$R$^{\#'}$ can be replaced by O, S(O)$_p$ or NR$^\#$;
p is 0, 1 or 2;
R$^\#$ is H, halogen, C$_{1-6}$ alkyl, C$_{1-6}$ haloalkyl, C$_{2-6}$ alkenyl or C$_{2-6}$ alkynyl;
R$^{\#'}$ is H, halogen, C$_{1-6}$ alkyl, C$_{1-6}$ haloalkyl, C$_{2-6}$ alkenyl or C$_{2-6}$ alkynyl;
or, R$^\#$ and R$^\#$ on adjacent atoms can be taken together to form bond, and R$^{\#'}$ and R$^{\#'}$ on adjacent atoms can be taken together to form bond;
or, R$^\#$ and R$^{\#'}$ on the same atom can be taken together to form =O;
m is 1;
alternatively, wherein
Z$_1$ is —CH$_2$— or —C(O)—;
L$_1$ is selected from bond, —O—, —NH—, —CH$_2$—, —CH$_2$CH$_2$—, —CH=CH— or —C≡C—;
E is —CH$_2$CH$_2$CH$_2$—, —CH$_2$CH=CH—, —CH—CHCH$_2$—, —CH$_2$C≡C—, —C≡CCH$_2$—, —CH$_2$CH$_2$C(O)—, —CH$_2$C(O)CH$_2$—, —C(O)CH$_2$CH$_2$—, —OCH$_2$C(O)—, —C(O)CH$_2$O—, —NHCH$_2$C(O)— or —C(O)CH$_2$NH—;
L$_3$ is selected from bond, —O—, —NH—, —CH$_2$—, —C(O)—, —CH$_2$CH$_2$—, —C(O)CH$_2$— or —CH$_2$C(O)—;
m is 1;
alternatively, wherein
Z$_1$ is —CH$_2$— or —C(O)—;
L$_1$ is selected from bond, —O—, —NH—, —CH$_2$—, —CH$_2$CH$_2$—, —CH=CH— or —C≡C—;
E is —CH$_2$CH$_2$CH$_2$—, —CH$_2$CH=CH—, —CH—CHCH$_2$—, —CH$_2$C=C— or —C≡CCH$_2$—;
L$_3$ is selected from bond, —O—, —NH—, —CH$_2$— or —C(O)—;
m is 1;
alternatively, wherein
Z$_1$ is —CH$_2$— or —C(O)—;
L$_1$ is selected from bond, —O—, —NH—, —CH$_2$—, —CH$_2$CH$_2$— or —C≡C—;
E is —CH$_2$CH$_2$CH$_2$—;
L$_3$ is selected from bond, —CH$_2$— or —C(O)—;
m is 1;
alternatively, wherein
Z$_1$ is —CH$_2$—;
L$_1$ is selected from bond, —CH$_2$—, —CH$_2$CH$_2$— or —C≡C—;
E is —CH$_2$CH$_2$CH$_2$—;
L$_3$ is selected from bond or —CH$_2$—;
m is 1.

15. The compound, or the pharmaceutically acceptable salt, enantiomer, diastereomer, racemate, solvate, hydrate, polymorph, prodrug, or isotopic variant thereof, or the mixture thereof according to claim 1, wherein the compound is selected from:

-continued
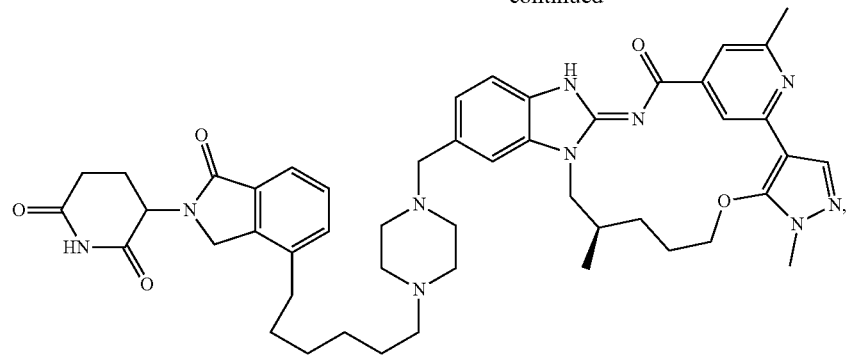
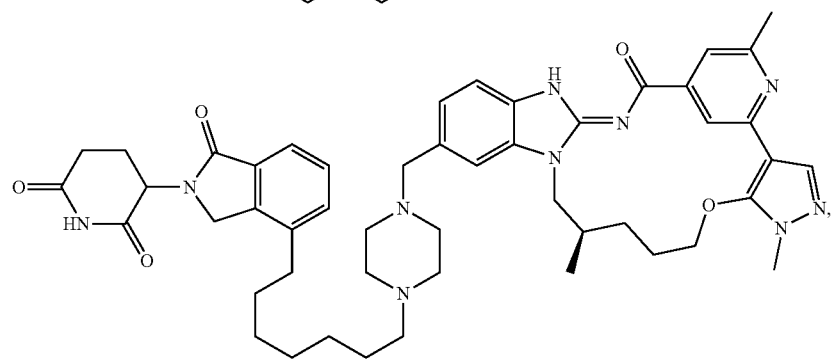
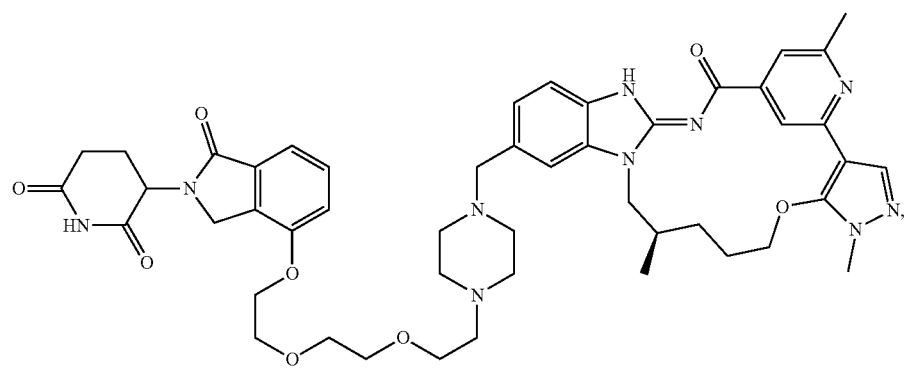
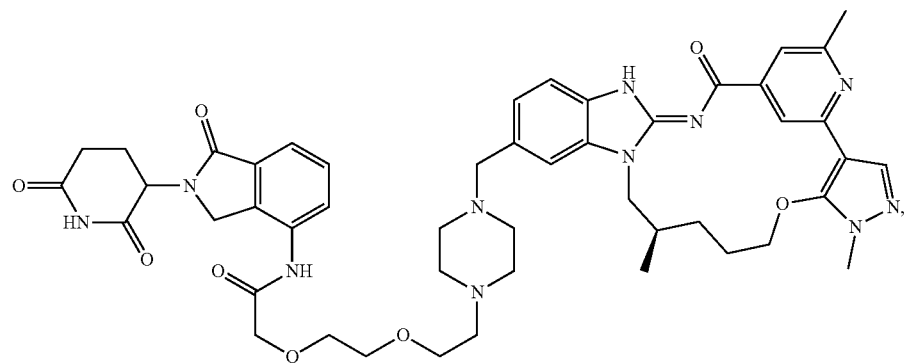

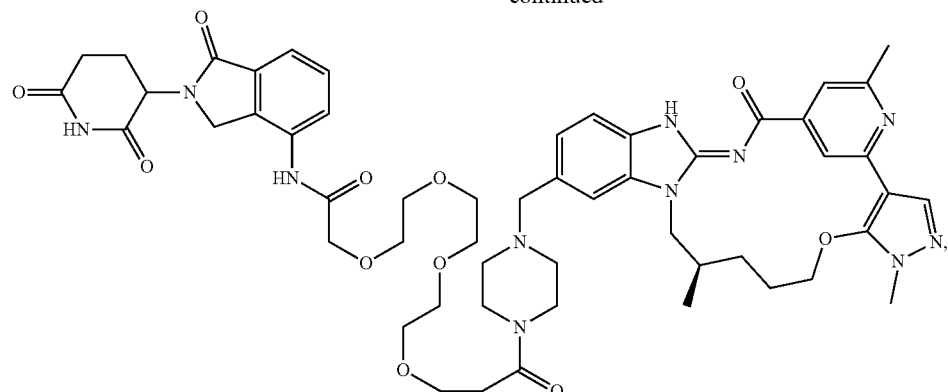
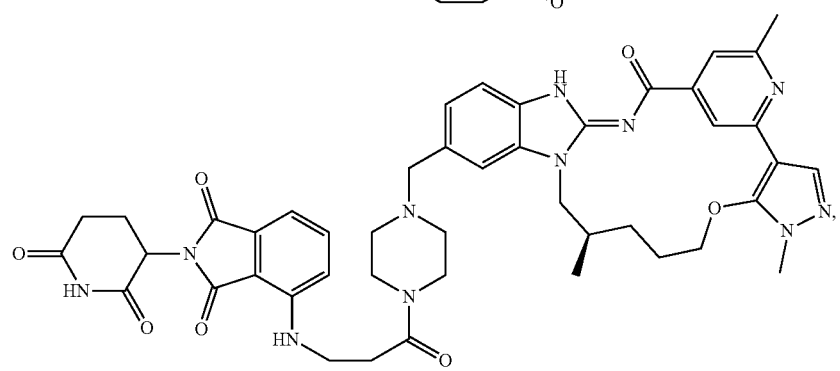
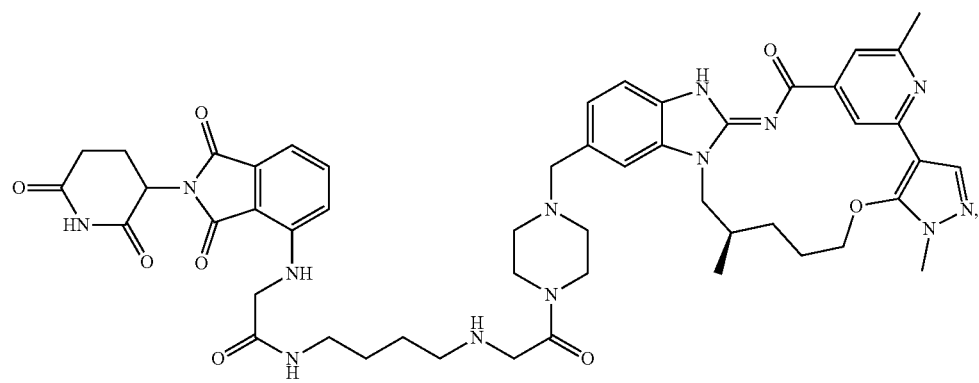
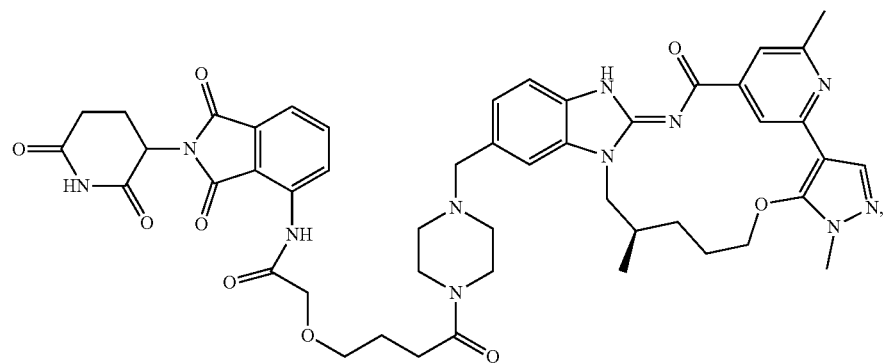

-continued
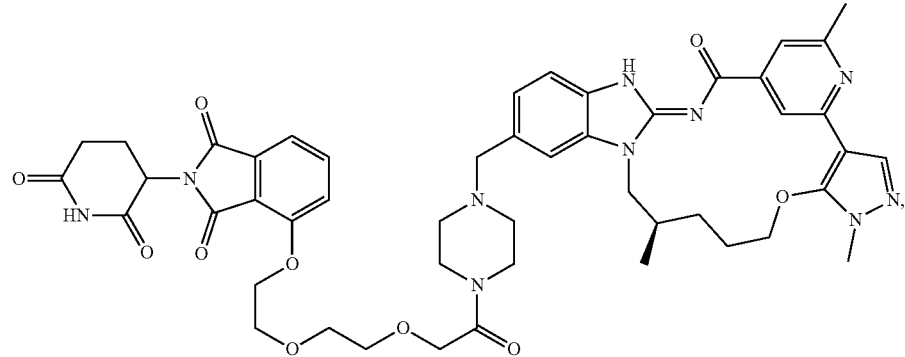
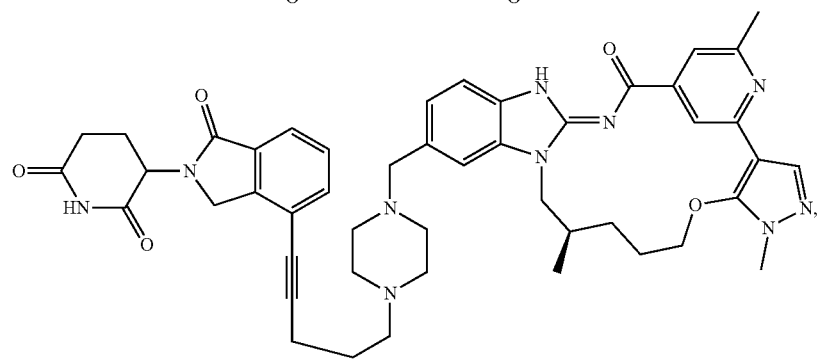
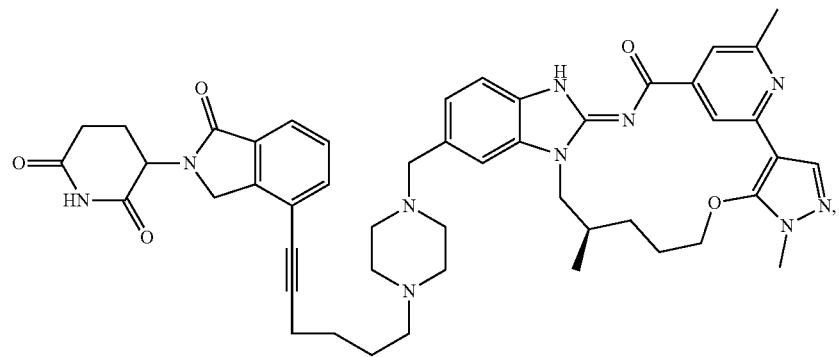
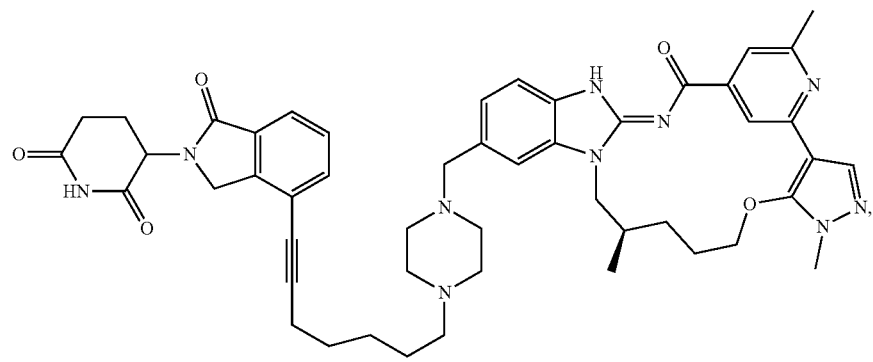

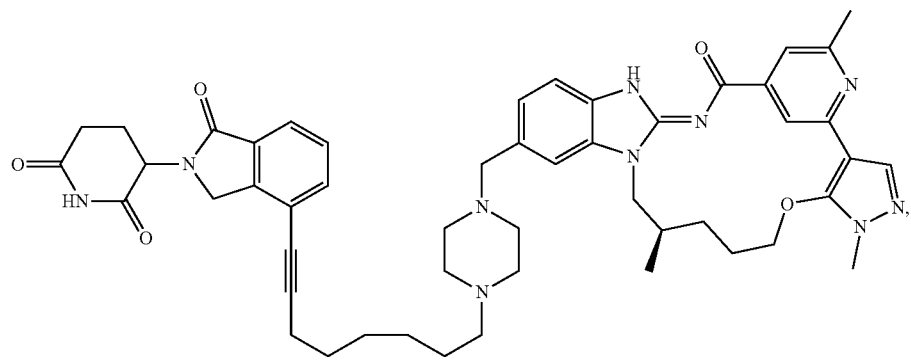
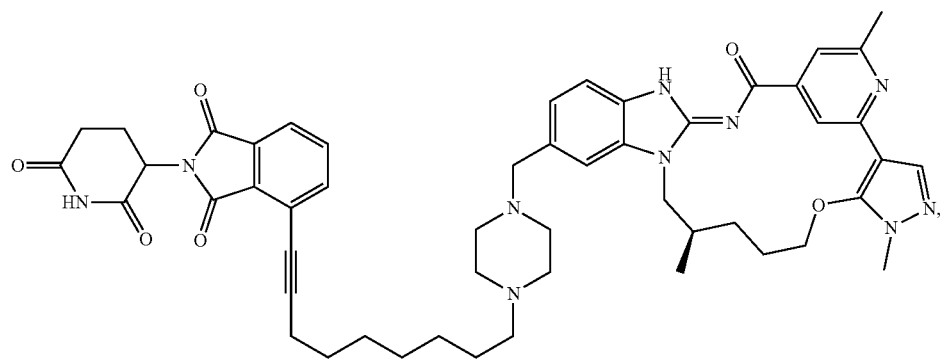
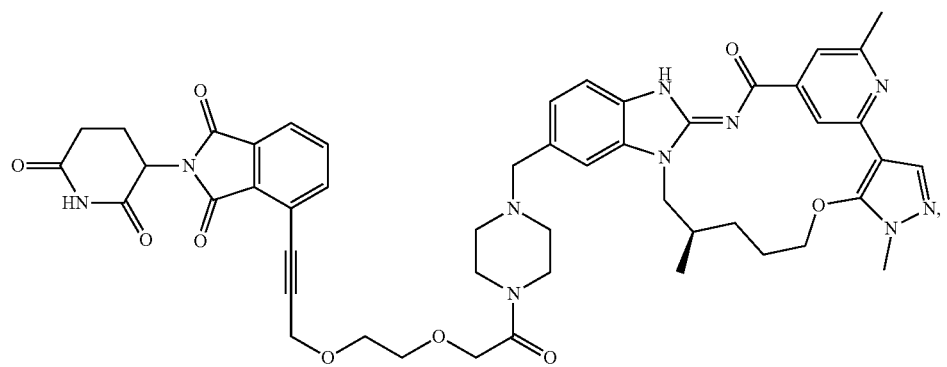
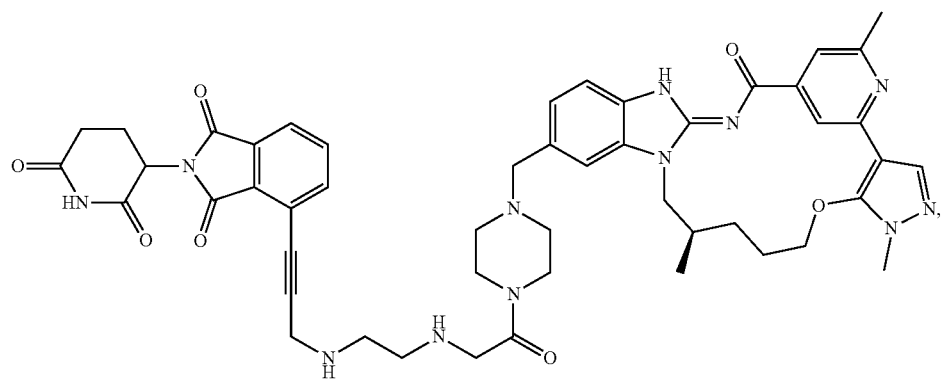

121 122
-continued
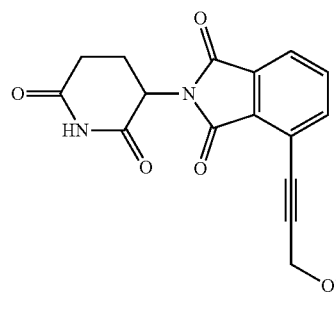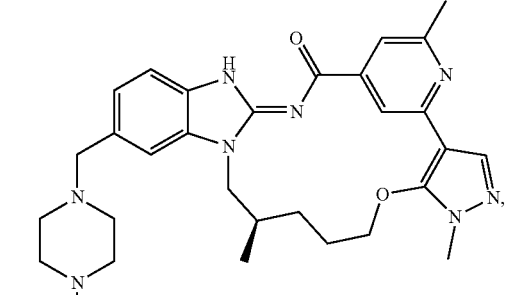
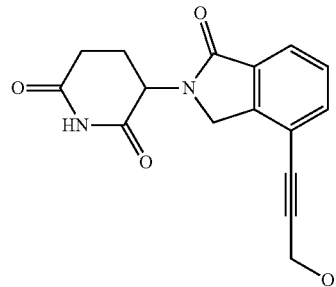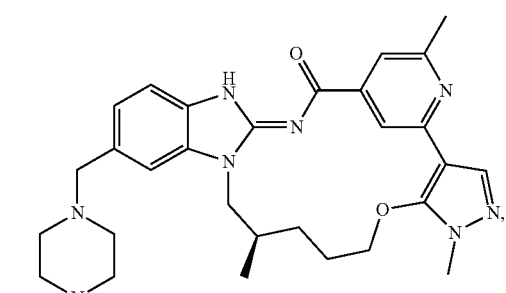
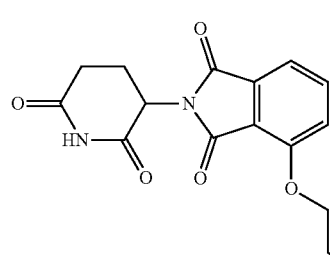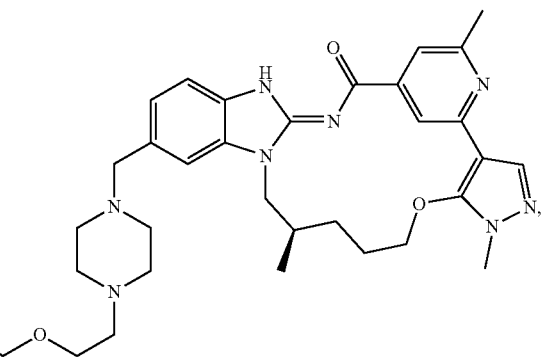
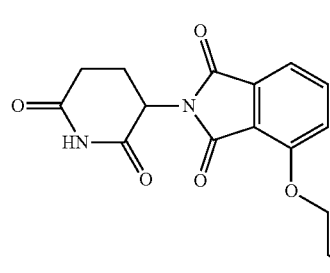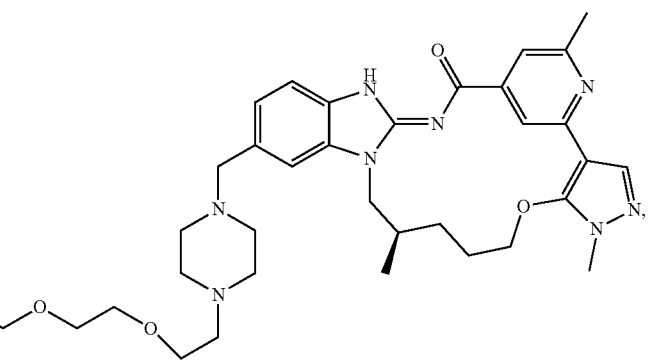

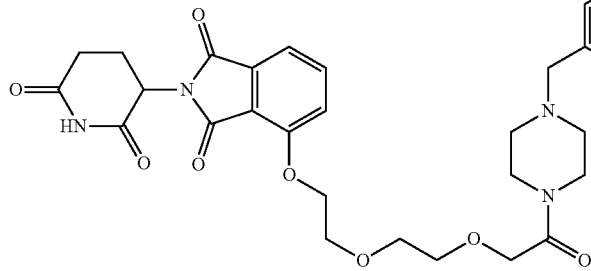
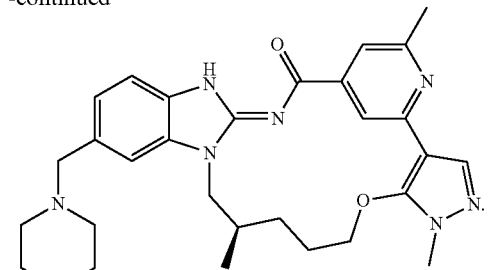

16. A pharmaceutical composition, comprising:
the compound, or the pharmaceutically acceptable salt, enantiomer, diastereomer, racemate, solvate, hydrate, polymorph, prodrug, or isotopic variant thereof, or the mixture thereof according to claim 1; and
pharmaceutically acceptable excipient(s);
alternatively, wherein the pharmaceutical composition further comprises other therapeutic agent(s).

17. A method of treating and/or preventing diseases mediated by EGFR kinase in a subject, comprising administering to the subject the compound, or the pharmaceutically acceptable salt, enantiomer, diastereomer, racemate, solvate, hydrate, polymorph, prodrug, or isotopic variant thereof, or the mixture thereof according to claim 1.

18. The method according to claim 17, wherein the diseases mediated by EGFR kinase include cancer, such as ovarian cancer, cervical cancer, colorectal cancer, breast cancer, pancreatic cancer, glioma, glioblastoma, melanoma, prostate cancer, leukemia, lymphoma, non-Hodgkin's lymphoma, gastric cancer, lung cancer, hepatocellular cancer, stomach cancer, gastrointestinal stromal tumor (GIST), thyroid cancer, cancer of bile duct, endometrial cancer, kidney cancer, anaplastic large cell lymphoma, acute myeloid leukemia (AML), multiple myeloma, melanoma, and mesothelioma.

19. A method of treating and/or preventing diseases mediated by EGFR kinase in a subject, comprising administering to the subject the pharmaceutical composition according to claim 16.

20. The method according to claim 19, wherein the diseases mediated by EGFR kinase include cancer, such as ovarian cancer, cervical cancer, colorectal cancer, breast cancer, pancreatic cancer, glioma, glioblastoma, melanoma, prostate cancer, leukemia, lymphoma, non-Hodgkins lymphoma, gastric cancer, lung cancer, hepatocellular cancer, stomach cancer, gastrointestinal stromal tumor (GIST), thyroid cancer, cancer of bile duct, endometrial cancer, kidney cancer, anaplastic large cell lymphoma, acute myeloid leukemia (AML), multiple myeloma, melanoma, and mesothelioma.

* * * * *